US011306329B2

(12) United States Patent
Chatterjee et al.

(10) Patent No.: US 11,306,329 B2
(45) Date of Patent: Apr. 19, 2022

(54) ADENO-ASSOCIATED VIRUS COMPOSITIONS FOR RESTORING F8 GENE FUNCTION AND METHODS OF USE THEREOF

(71) Applicants: CITY OF HOPE, Duarte, CA (US); HOMOLOGY MEDICINES, INC., Bedford, MA (US)

(72) Inventors: Saswati Chatterjee, Altadena, CA (US); Laura Jane Smith, Westford, MA (US); Jeff Lynn Ellsworth, Lexington, MA (US); Hillard Rubin, Northborough, MA (US); Jason Boke Wright, Concord, MA (US); James Anthony McSwiggen, Arlington, MA (US)

(73) Assignees: CITY OF HOPE, Duarte, CA (US); HOMOLOGY MEDICINES, INC., Bedford, MA (US)

( * ) Notice: Subject to any disclaimer, the term of this patent is extended or adjusted under 35 U.S.C. 154(b) by 293 days.

(21) Appl. No.: 16/279,688

(22) Filed: Feb. 19, 2019

(65) Prior Publication Data

US 2019/0276856 A1 Sep. 12, 2019

Related U.S. Application Data

(60) Provisional application No. 62/632,300, filed on Feb. 19, 2018, provisional application No. 62/632,919, filed on Feb. 20, 2018, provisional application No. 62/672,385, filed on May 16, 2018.

(51) Int. Cl.

| | |
|---|---|
| ***C12N 15/86*** | (2006.01) |
| ***C12N 15/90*** | (2006.01) |
| ***C12N 7/00*** | (2006.01) |

(52) U.S. Cl.

CPC ............. *C12N 15/907* (2013.01); *C12N 7/00* (2013.01); *C12N 15/86* (2013.01); *C12N 2710/10042* (2013.01); *C12N 2710/10043* (2013.01); *C12N 2710/10061* (2013.01)

(58) Field of Classification Search

CPC ...................... C12N 7/00; C12N 15/86; C12N 2710/10042; C12N 2710/10043; C12N 2710/10061; C12N 2750/14143; C12N 15/907; C07K 14/755

See application file for complete search history.

(56) References Cited

U.S. PATENT DOCUMENTS

| | | | |
|---|---|---|---|
| 5,252,479 | A | 10/1993 | Srivastava |
| 5,474,935 | A | 12/1995 | Chatterjee et al. |
| 5,589,377 | A | 12/1996 | Lebkowski et al. |
| 5,622,856 | A | 4/1997 | Natsoulis |
| 5,650,309 | A | 7/1997 | Wong-Staal et al. |
| 5,753,500 | A | 5/1998 | Shenk et al. |
| 5,780,447 | A | 7/1998 | Nienhuis |
| 5,895,759 | A | 4/1999 | Strauss et al. |
| 6,025,195 | A | 2/2000 | Sandig et al. |
| 6,153,436 | A | 11/2000 | Hermonat et al. |
| 6,156,303 | A | 12/2000 | Russell et al. |
| 6,180,613 | B1 | 1/2001 | Kaplitt et al. |
| 6,238,914 | B1 | 5/2001 | Boyce |
| 6,268,212 | B1 | 7/2001 | Simonet |
| 6,329,181 | B1 | 12/2001 | Xiao et al. |
| 6,338,962 | B1 | 1/2002 | Boyce |
| 6,387,670 | B1 | 5/2002 | Leblois-Prehaud et al. |
| 6,610,906 | B1 | 8/2003 | Kurachi et al. |
| 6,759,237 | B1 | 7/2004 | Wilson et al. |
| 6,919,209 | B1 | 7/2005 | Chatterjee et al. |
| 6,924,128 | B2 | 8/2005 | Allen |
| 6,936,243 | B2 | 8/2005 | Snyder et al. |
| 6,936,466 | B2 | 8/2005 | Feldhaus |
| 6,953,690 | B1 | 10/2005 | Gao et al. |
| 6,984,517 | B1 | 1/2006 | Chiorini et al. |
| 7,001,764 | B2 | 2/2006 | Little et al. |
| 7,022,519 | B2 | 4/2006 | Gao et al. |
| 7,056,502 | B2 | 6/2006 | Hildinger et al. |
| 7,091,029 | B2 | 8/2006 | Hwang |
| 7,094,604 | B2 | 8/2006 | Snyder et al. |
| 7,148,341 | B2 | 12/2006 | Kleinschmidt et al. |

(Continued)

FOREIGN PATENT DOCUMENTS

| | | | |
|---|---|---|---|
| EP | 746624 | B1 | 12/1996 |
| WO | WO 1996/008560 | A1 | 3/1996 |

(Continued)

OTHER PUBLICATIONS

Barzel, A., Paulk, N., Shi, Y. et al. Promoterless gene targeting without nucleases ameliorates haemophilia B in mice. Nature 517, 360-364 (2015). (Year: 2015).*

Clark et al. (2016) "GenBank," Nucleic Acids Res. 44(Database issue): D67-D72.

Farré et al. (2003) "Identification of patterns in biological sequences at the ALGGEN server: PROMO and MALGEN," Nucleic Acids Res. 31(13):3651-3653.

(Continued)

*Primary Examiner* — Antonio Galisteo Gonzalez
*Assistant Examiner* — Khaleda B Hasan
(74) *Attorney, Agent, or Firm* — Dechert LLP; Andrew T. Wilkins; Elizabeth A. Browning

(57) ABSTRACT

Provided herein are adeno-associated virus (AAV) compositions that can restore F8 gene function in a cell without co-transducing or co-administering an exogenous nuclease or a nucleotide sequence that encodes an exogenous nuclease. Also provided are methods of using the AAV compositions to correct an F8 gene mutation and/or treat a disease or disorder associated with an F8 gene mutation. Packaging systems for making the adeno-associated virus compositions are also provided.

18 Claims, 27 Drawing Sheets

Specification includes a Sequence Listing.

(56) References Cited

U.S. PATENT DOCUMENTS

| | | | |
|---|---|---|---|
| 7,157,571 | B2 | 1/2007 | Wang et al. |
| 7,172,893 | B2 | 2/2007 | Rabinowitz et al. |
| 7,179,903 | B2 | 2/2007 | McArthur et al. |
| 7,198,951 | B2 | 4/2007 | Gao et al. |
| 7,220,577 | B2 | 5/2007 | Zolotukhin |
| 7,235,393 | B2 | 6/2007 | Gao et al. |
| 7,259,151 | B2 | 8/2007 | Arbetman et al. |
| 7,282,199 | B2 | 10/2007 | Gao et al. |
| 7,351,813 | B2 | 4/2008 | Miao et al. |
| 7,465,583 | B2 | 12/2008 | Samulski et al. |
| 7,482,156 | B2 | 1/2009 | Arroyo et al. |
| 7,588,772 | B2 | 9/2009 | Kay et al. |
| 7,749,492 | B2 | 7/2010 | Bartlett et al. |
| 7,790,154 | B2 | 9/2010 | Samulski et al. |
| 7,906,111 | B2 | 3/2011 | Wilson et al. |
| 8,030,065 | B2 | 10/2011 | Gray |
| 8,067,156 | B2 | 11/2011 | Kaplitt et al. |
| 8,163,543 | B2 | 4/2012 | Urabe et al. |
| 8,168,425 | B2 | 5/2012 | Gray |
| 8,241,622 | B2 | 8/2012 | Englehardt et al. |
| 8,283,151 | B2 | 10/2012 | Schmidt et al. |
| 8,298,818 | B2 | 10/2012 | Boye et al. |
| 8,476,418 | B2 | 7/2013 | Mueller et al. |
| 8,524,446 | B2 | 9/2013 | Gao et al. |
| 8,628,966 | B2 | 1/2014 | Chatterjee et al. |
| 8,632,764 | B2 | 1/2014 | Xiao et al. |
| 8,716,461 | B2 | 5/2014 | Delwart et al. |
| 8,802,620 | B2 * | 8/2014 | Chtourou .................. A61P 7/02 514/1.1 |
| 8,846,387 | B2 | 9/2014 | Russell et al. |
| 8,846,389 | B2 | 9/2014 | Chiorini et al. |
| 8,926,958 | B2 | 1/2015 | Shah et al. |
| 8,999,678 | B2 | 4/2015 | Vandenberghe et al. |
| 8,999,948 | B2 | 4/2015 | Tubert et al. |
| 9,150,882 | B2 | 10/2015 | Kay et al. |
| 9,169,299 | B2 | 10/2015 | Lisowski et al. |
| 9,169,494 | B2 | 10/2015 | Hewitt et al. |
| 9,193,956 | B2 | 11/2015 | Schaffer et al. |
| 9,217,155 | B2 | 12/2015 | Gao et al. |
| 9,222,105 | B2 | 12/2015 | Cost et al. |
| 9,402,919 | B2 | 8/2016 | Roeth et al. |
| 9,408,904 | B2 | 8/2016 | Wright et al. |
| 9,409,953 | B2 | 8/2016 | Asokan et al. |
| 9,441,244 | B2 | 9/2016 | Schaffer et al. |
| 9,617,548 | B2 | 4/2017 | Chuah et al. |
| 9,764,045 | B2 | 9/2017 | Nathwani et al. |
| 9,783,824 | B2 | 10/2017 | Kay et al. |
| 9,840,719 | B2 | 12/2017 | High et al. |
| 9,890,396 | B2 | 2/2018 | Chatterjee et al. |
| 2003/0129203 | A1 | 7/2003 | Vega et al. |
| 2003/0130221 | A1 | 7/2003 | High et al. |
| 2004/0086485 | A1 | 5/2004 | Aguilar-Cordova et al. |
| 2004/0235174 | A1 | 11/2004 | Grimm et al. |
| 2005/0112765 | A1 | 5/2005 | Li et al. |
| 2009/0191597 | A1 | 7/2009 | Sumulski et al. |
| 2009/0215879 | A1 | 8/2009 | Diprimio et al. |
| 2010/0297084 | A1 | 11/2010 | Bennett et al. |
| 2012/0046349 | A1 | 2/2012 | Bell et al. |
| 2012/0093772 | A1 | 4/2012 | Horsager et al. |
| 2012/0244127 | A1 | 9/2012 | Lipschutz et al. |
| 2013/0023033 | A1 | 1/2013 | Wilson et al. |
| 2013/0189225 | A1 | 7/2013 | Voit et al. |
| 2013/0310443 | A1 | 11/2013 | Srivastava et al. |
| 2013/0323226 | A1 | 12/2013 | Wilson et al. |
| 2014/0037585 | A1 | 2/2014 | Wright et al. |
| 2014/0050701 | A1 | 2/2014 | Zhong et al. |
| 2014/0107185 | A1 | 4/2014 | Maclaren et al. |
| 2014/0271550 | A1 | 9/2014 | Rabinowitz et al. |
| 2014/0336245 | A1 | 11/2014 | Mingozzi et al. |
| 2014/0359799 | A1 | 12/2014 | Wang et al. |
| 2015/0023924 | A1 | 1/2015 | High et al. |
| 2015/0024467 | A1 | 1/2015 | Sheldon et al. |
| 2015/0065562 | A1 | 3/2015 | Yazicioglu et al. |
| 2015/0079038 | A1 | 3/2015 | Deverman et al. |
| 2015/0110762 | A1 | 4/2015 | Holmes et al. |
| 2015/0111955 | A1 | 4/2015 | High et al. |
| 2015/0184197 | A1 | 7/2015 | Davidson et al. |
| 2015/0238550 | A1 | 8/2015 | McCown et al. |
| 2015/0306250 | A1 * | 10/2015 | Laterza .............. A61K 48/0066 424/278.1 |
| 2015/0315610 | A1 | 11/2015 | Nishe et al. |
| 2015/0352228 | A1 | 12/2015 | Torbett et al. |
| 2015/0374803 | A1 | 12/2015 | Wolfe |
| 2015/0376240 | A1 | 12/2015 | Cronin et al. |
| 2016/0000887 | A1 | 1/2016 | Wilson et al. |
| 2016/0017295 | A1 | 1/2016 | Schaffer et al. |
| 2016/0032319 | A1 | 2/2016 | Wright et al. |
| 2016/0123990 | A1 | 5/2016 | High et al. |
| 2016/0175365 | A1 | 6/2016 | Golden |
| 2016/0229904 | A1 | 8/2016 | Xiao et al. |
| 2017/0081680 | A1 * | 3/2017 | Chatterjee ............... A61P 43/00 |
| 2017/0119906 | A1 | 5/2017 | Riley |
| 2017/0198265 | A1 | 7/2017 | Chatterjee et al. |
| 2017/0326256 | A1 | 11/2017 | Doering et al. |
| 2018/0163227 | A1 * | 6/2018 | Chatterjee ................ C12N 7/00 |
| 2018/0282765 | A1 * | 10/2018 | Chatterjee ............... A61P 31/00 |

FOREIGN PATENT DOCUMENTS

| | | | |
|---|---|---|---|
| WO | WO 1998/009524 | A1 | 3/1998 |
| WO | WO 1998/021349 | A1 | 5/1998 |
| WO | WO 1998/027207 | A1 | 6/1998 |
| WO | WO 1998/028417 | A1 | 7/1998 |
| WO | WO 1999/003981 | A1 | 1/1999 |
| WO | WO 1999/018227 | A1 | 4/1999 |
| WO | WO 1999/055564 | A1 | 11/1999 |
| WO | WO 1999/064569 | A1 | 12/1999 |
| WO | WO 2001/036620 | A2 | 5/2001 |
| WO | WO 2002/066611 | A2 | 8/2002 |
| WO | WO 2005/111220 | A2 | 11/2005 |
| WO | WO 2006/096815 | A2 | 9/2006 |
| WO | WO 2007/019646 | A1 | 2/2007 |
| WO | WO 2008/021140 | A2 | 2/2008 |
| WO | WO 2009/043936 | A1 | 4/2009 |
| WO | WO 2009/130208 | A1 | 10/2009 |
| WO | WO 2009/134681 | A2 | 11/2009 |
| WO | WO 2011/012724 | A1 | 2/2011 |
| WO | WO 2011038187 | A1 | 3/2011 |
| WO | WO 2014/064277 | A1 | 5/2014 |
| WO | WO 2014/089212 | A1 | 6/2014 |
| WO | WO 2014/193716 | A2 | 12/2014 |
| WO | WO 2015/143177 | A1 | 9/2015 |
| WO | WO 2015/164723 | A1 | 10/2015 |
| WO | WO 2016/049230 | A1 | 3/2016 |
| WO | WO 2016/097218 | A1 | 6/2016 |
| WO | WO 2016/097219 | A1 | 6/2016 |
| WO | WO 2016/100575 | A1 | 6/2016 |
| WO | WO 2016/146757 | A1 | 9/2016 |
| WO | WO 2017/100551 | A1 | 6/2017 |
| WO | WO 2018/126116 | A1 | 7/2018 |
| WO | WO 2018/129586 | A1 | 7/2018 |
| WO | WO 2019/010091 | A1 | 1/2019 |

OTHER PUBLICATIONS

Frock et al. (2015) "Genome-wide detection of DNA double-stranded breaks induced by engineered nucleases," Nat Biotechnol. 33: 179-186.

Griffith et al. (2008) "ORegAnno: an open-access community-driven resource for regulatory annotation," Nucleic Acids Res 36: D107-13.

Hacein-Bey-Abina et al. (2008) "Insertional oncogenesis in 4 patients after retrovirus-mediated gene therapy of SCID-X1," J Clin Invest. 118(9):3132-42.

Khan et al. (2018) "JASPAR 2018: update of the open-access database of transcription factor binding profiles and its web framework," Nucleic Acids Res. 46(D1):D260-D266.

Kramer et al. (2003) "In vitro and in vivo comparative study of chimeric liver-specific promoters," Mol Therapy. 7:375-385.

Landrum et al. (2014) "ClinVar: public archive of relationships among sequence variation and human phenotype," Nucleic Acids Res. 42(Database issue):D980-5.

(56) References Cited

OTHER PUBLICATIONS

Lu et al. (2013) "A mini-intronic plasmid (MIP): a novel robust transgene expression vector in vivo and in vitro," Mol Ther. 21(5):954-63.
Lu et al. (2017) "A 5' Noncoding Exon Containing Engineered Intron Enhances Transgene Expression from Recombinant AAV Vectors in vivo," Hum Gene Ther. 28(1):125-134.
Mauro (2014) "A critical analysis of codon optimization in human therapeutics," Trends Mol Med. 20(11):604-13.
MacDonald et al. (2014) "The Database of Genomic Variants: a curated collection of structural variation in the human genome," Nucleic Acids Res. 42(Database issue):D986-92.
Messeguer et al. (2002) Bioinformatics. "PROMO: detection of known transcription regulatory elements using species-tailored searches," 18(2):333-334.
Nair et al. (2016) "A simple practice guide for dose conversion between animals and human," J. Basic Clin. Pharm. 7(2): 27-31.
Rando et al. (2009) "Genome-wide views of chromatin structure," Annu Rev Biochem 78: 245-71.
Sabo et al. (2006) "Genome-scale mapping of DNase 1 sensitivity in vivo using tiling DNA microarrays," Nat Methods 3: 511-18.
Savy et al. (2017) "Impact of Inverted Terminal Repeat Integrity on rAAV8 Production Using the Baculovirus/Sf9 Cells System," Human Gene Therapy Methods. 28(5):277-289.
Sherry et al. (2001) "dbSNP: the NCBI database of genetic variation," Nucleic Acids Res. 29(1):308-11.
Sibley et al. (2016) "Lessons from non-canonical splicing," Nat Rev Gen. 17:407-21.
International Search Report and Written Opinion from PCT/US2019/18502 dated Jun. 28, 2019.
Vandendreissche et al. (2015) "Hitting the target without pulling the trigger," The American Society of Gene & Cell Therapy. 23(1):4-6.

* cited by examiner

Figure 9C
5' ITR Cam/NC004101/pTZAAV (FLIP)
5' ITR to CBA Promoter (pSal-Luc)
F8 HA-L e22
F8 e22
Kan
pHMI-F8-003-F8
4589 bp
ori
SnaBI to 3'ITR (pSal-Luc)
3' ITR Cam/NC004101/pTZAAV (FLOP)

ADENO-ASSOCIATED VIRUS COMPOSITIONS FOR RESTORING F8 GENE FUNCTION AND METHODS OF USE THEREOF

RELATED APPLICATIONS

This application claims priority to U.S. Provisional Patent Application Serial Nos. 62/632,300, filed Feb. 19, 2018, 62/632,919, filed Feb. 20, 2018, and 62/672,385, filed May 16, 2018, the entire disclosures of which are hereby incorporated herein by reference.

SEQUENCE LISTING

The instant application contains a Sequence Listing which has been submitted electronically in ASCII format and is hereby incorporated by reference in its entirety. Said ASCII copy, created on Feb. 19, 2019, is named 610725_HMT-026_Sequence_Listing.TXT and is 156,990 bytes in size.

STATEMENT OF GOVERNMENT INTEREST

This invention was made with government support under Grant No. P30CA033572 awarded by the National Institutes of Health. The Government has certain rights in the invention.

BACKGROUND

Factor VIII (FVIII), also known as anti-hemophilic factor, is a circulating glycoprotein that is important for normal blood clotting. Factor VIII is produced by liver sinusoidal endothelial cells and endothelial cells outside of the liver. This protein circulates in the bloodstream in an inactive form, bound to another molecule called von Willebrand factor (vWF), until an injury that damages blood vessels occurs. In response to injury, FVIII is activated and separates from vWF. The active protein, FVIIIa, interacts with another coagulation factor called factor IX to initiate a cascade of additional chemical reactions that form a blood clot.

Hemophilia A, also called factor VIII deficiency or classic hemophilia, is an inherited or spontaneous genetic disorder caused by missing or defective factor VIII. In the majority of cases it is inherited as an X-linked recessive trait, while nearly one third of cases arise from spontaneous mutations. Clinically, hemophilia A is characterized by internal or external bleeding episodes. Individuals with more severe hemophilia suffer more severe and more frequent bleeding, while others with mild haemophilia typically suffer more minor symptoms except after surgery or serious trauma; individuals with moderate hemophilia have variable symptoms which manifest along a spectrum between severe and mild forms.

F8, the gene for FVIII is located on the long arm of chromosome X, within the Xq28 region. The gene represents 186 kb of the X chromosome. It comprises a 9 kb coding region that contains 26 exons and 25 introns. Mature FVIII is a single-chain polypeptide containing 2332 amino acids. Approximately 40% of cases of severe FVIII deficiency arise from a large inversion involving intron 22 that disrupts the F8 gene. Deletions, insertions, and point mutations account for the remaining 50-60% of the F8 defects that cause hemophilia A.

Currently there is no cure for hemophilia A. For patients with moderate to severe hemophilia A or acute bleeding episodes, treatment typically involves an infusion of recombinant FVIII or FVIII derived from donated human blood. Patients may also be treated prophylactically with regular infusions of FVIII or desmopressin (DDAVP), the latter directly promoting the release of von Willebrand factor (vWF) and indirectly promoting FVIII half-life.

Gene therapy provides a unique opportunity to cure genetic disorders. Retroviral vectors, including lentiviral vectors, are capable of integrating nucleic acids into host cell genomes. However, these vectors may raise safety concerns due to their non-targeted insertion into the genome. For example, there is a risk of the vector disrupting a tumor suppressor gene or activating an oncogene, thereby causing a malignancy. Indeed, in a clinical trial for treating X-linked severe combined immunodeficiency (X-SCID) by transducing $CD34^+$ bone marrow precursors with a gammaretroviral vector, four out of ten patients developed leukemia (Hacein-Bey-Abina et al., *J. Clin. Invest.* (2008) 118(9):3132-42).

Nuclease-based gene editing technologies, such as meganucleases, zinc finger nucleases (ZFNs), transcription activator-like effector nucleases (TALENs), and clustered, regularly interspaced, short palindromic repeat (CRISPR) technology, may be used to correct defects in genes in patients. However, each of these technologies raises safety concerns due to the potential for off-target mutation of sites in the human genome similar in sequence to the intended target site.

Accordingly, there is a need in the art for improved gene therapy compositions and methods that can efficiently and safely restore F8 gene function in hemophilia A patients.

SUMMARY

Provided herein are adeno-associated virus (AAV) compositions that can restore F8 gene function in cells, and methods for using the same to treat diseases associated with reduction of F8 gene function (e.g., hemophilia A). Also provided are packaging systems for making the adeno-associated virus compositions.

The AAV compositions and methods disclosed herein are particularly advantageous in that they allow for highly efficient correction of mutations in an F8 gene in vivo, without the need for cleavage of genomic DNA using an exogenous nuclease (e.g., a meganuclease, a zinc finger nuclease, a transcriptional activator-like nuclease (TALEN), or an RNA-guided nuclease such as a Cas9).

Accordingly, in one aspect the instant disclosure provides a replication-defective adeno-associated virus (AAV) comprising: an AAV capsid; and a correction genome comprising: (i) an editing element for editing a target locus in the F8 gene; (ii) a 5' homology arm nucleotide sequence 5' to the editing element having homology to a first genomic region 5' to the target locus; and (iii) a 3' homology arm nucleotide sequence 3' to the editing element having homology to a second genomic region 3' to the target locus, wherein the portion of the correction genome comprising the 5' homology arm, editing element, and 3' homology arm can be in the sense or antisense orientation relative to the F8 gene locus.

In another aspect, a method for correcting a mutation in an F8 gene in a cell, the method comprising transducing the cell with a replication-defective adeno-associated virus (AAV) comprising: an AAV capsid; and a correction genome comprising: (i) an editing element for editing a target locus in the F8 gene; (ii) a 5' homology arm nucleotide sequence 5' to the editing element having homology to a first genomic region 5' to the target locus; and (iii) a 3' homology arm nucleotide sequence 3' to the editing element having homology to a second genomic region 3' to the target locus, wherein the portion of the correction genome comprising the 5' homology arm, editing element, and 3' homology arm can be in the sense or antisense orientation relative to the F8 gene locus, wherein the cell is transduced without co-transducing or co-administering an exogenous nuclease or a nucleotide sequence that encodes an exogenous nuclease.

In certain embodiments, the cell is a hepatocyte or an endothelial cell. In certain embodiments, the endothelial cell is a hepatic sinusoidal endothelial cell. In certain embodiments, the cell is in a mammalian subject and the AAV is administered to the subject in an amount effective to transduce the cell in the subject.

In another aspect, the instant disclosure provides a method for treating a subject having a disease or disorder associated with an F8 gene mutation, the method comprising administering to the subject an effective amount of a replication-defective AAV comprising: an AAV capsid comprising an AAV Clade F capsid protein; and a correction genome comprising: (i) an editing element for editing a target locus in the F8 gene; (ii) a 5' homology arm nucleotide sequence 5' to the editing element having homology to a first genomic region 5' to the target locus; and (iii) a 3' homology arm nucleotide sequence 3' to the editing element having homology to a second genomic region 3' to the target locus, wherein an exogenous nuclease or a nucleotide sequence that encodes an exogenous nuclease is not co-administered to the subject.

In certain embodiments, the disease or disorder is hemophilia A. In certain embodiments, the subject is a human subject.

The following embodiments apply to each of the foregoing aspects.

In certain embodiments, the editing element comprises a portion of an F8 coding sequence. In certain embodiments, the portion of the F8 coding sequence encodes an amino acid sequence set forth in SEQ ID NO: 25. In certain embodiments, the portion of the F8 coding sequence comprises or consists of the sequence set forth in SEQ ID NO: 26. In certain embodiments, the portion of the F8 coding sequence is silently altered.

In certain embodiments, the editing element comprises 5' to 3' a portion of an F8 coding sequence and a polyadenylation sequence. In certain embodiments, the portion of the F8 coding sequence consists of the sequence set forth in SEQ ID NO: 26. In certain embodiments, the target locus is the internucleotide bond between nucleotide 126,476 and nucleotide 126,477 of the F8 gene. In certain embodiments, the target locus is a nucleotide sequence adjacently 3' to nucleotide 126,476 of the F8 gene.

In certain embodiments, the editing element comprises 5' to 3' a splice acceptor site, a portion of an F8 coding sequence, and optionally a polyadenylation sequence. In certain embodiments, the nucleotide adjacently 5' to the target locus is in an intron of the F8 gene. In certain embodiments, the portion of the F8 coding sequence consists of the sequence set forth in SEQ ID NO: 26. In certain embodiments, the nucleotide adjacently 5' to the target locus is in intron 22 of the F8 gene.

In certain embodiments, the polyadenylation sequence is an exogenous polyadenylation sequence. In certain embodiments, the exogenous polyadenylation sequence is an SV40 polyadenylation sequence. In certain embodiments, the SV40 polyadenylation sequence has a nucleotide sequence set forth in SEQ ID NO: 23, 35, 36, or 37.

In certain embodiments, the editing element comprises the nucleic acid sequence set forth in SEQ ID NO: 33.

In certain embodiments, the 5' homology arm nucleotide sequence is at least 90%, 95%, 96%, 97%, 98%, or 99% identical to the first genomic region. In certain embodiments, the 3' homology arm nucleotide sequence is at least 90%, 95%, 96%, 97%, 98%, or 99% identical to the second genomic region. In certain embodiments, the first genomic region is located in a first editing window, and the second genomic region is located in a second editing window. In certain embodiments, the first editing window consists of the nucleotide sequence set forth in SEQ ID NO: 31, 32, or 34. In certain embodiments, the second editing window consists of the nucleotide sequence set forth in SEQ ID NO: 31, 32, or 34. In certain embodiments, the first editing window consists of the nucleotide sequence set forth in SEQ ID NO: 31, and the second editing window consists of the nucleotide sequence set forth in SEQ ID NO: 32.

In certain embodiments, the first genomic region consists of the nucleotide sequence set forth in SEQ ID NO: 31. In certain embodiments, the second genomic region consists of the nucleotide sequence set forth in SEQ ID NO: 32.

In certain embodiments, each of the 5' and 3' homology arm nucleotide sequences independently has a length of about 100 to about 4500 nucleotides. In certain embodiments, the correction genome comprises a nucleic acid sequence selected from the group consisting of SEQ ID NOs: 38-41.

In certain embodiments, the correction genome further comprises a 5' inverted terminal repeat (5' ITR) nucleotide sequence 5' to the 5' homology arm nucleotide sequence, and a 3' inverted terminal repeat (3' ITR) nucleotide sequence 3' to the 3' homology arm nucleotide sequence. In certain embodiments, the 5' ITR nucleotide sequence has at least 95% sequence identity to SEQ ID NO: 18, and the 3' ITR nucleotide sequence has at least 95% sequence identity to SEQ ID NO: 19, 61, or 63. In certain embodiments, the 5' ITR nucleotide sequence has at least 95% sequence identity to SEQ ID NO: 20, and the 3' ITR nucleotide sequence has at least 95% sequence identity to SEQ ID NO: 21. In certain embodiments, the 5' ITR nucleotide sequence has at least 95% sequence identity to SEQ ID NO: 46, and the 3' ITR nucleotide sequence has at least 95% sequence identity to SEQ ID NO: 19, 61, or 63.

In certain embodiments, the correction genome comprises a nucleic acid sequence selected from the group consisting of SEQ ID NOs: 42-45. In certain embodiments, the correction genome consists of a nucleic acid sequence selected from the group consisting of SEQ ID NOs: 42-45.

In certain embodiments, the integration efficiency of the editing element into the target locus is at least 2% when the AAV is contacted in vitro in the absence of an exogenous nuclease with a population of B lymphoblastoid cells under standard AAV transduction conditions. In certain embodiments, the allelic frequency of integration of the editing element into the target locus is at least 1% when the AAV is contacted in vitro in the absence of an exogenous nuclease with a population of B lymphoblastoid cells under standard AAV transduction conditions.

In certain embodiments, the AAV capsid comprises an AAV Clade F capsid protein.

In certain embodiments, the AAV Clade F capsid protein comprises an amino acid sequence having at least 95% sequence identity with the amino acid sequence of amino acids 203-736 of SEQ ID NO: 1, 2, 3, 4, 6, 7, 10, 11, 12, 13, 15, 16, or 17. In certain embodiments, the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G.

In certain embodiments, (a) the amino acid in the capsid protein corresponding to amino acid 626 of SEQ ID NO: 2 is G, and the amino acid in the capsid protein corresponding to amino acid 718 of SEQ ID NO: 2 is G;

(b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;

(c) the amino acid in the capsid protein corresponding to amino acid 505 of SEQ ID NO: 2 is R, and the amino acid in the capsid protein corresponding to amino acid 687 of SEQ ID NO: 2 is R;

(d) the amino acid in the capsid protein corresponding to amino acid 346 of SEQ ID NO: 2 is A, and the amino acid in the capsid protein corresponding to amino acid 505 of SEQ ID NO: 2 is R; or (e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 203-736 of SEQ ID NO: 1, 2, 3, 4, 6, 7, 10, 11, 12, 13, 15, 16, or 17.

In certain embodiments, the AAV Clade F capsid protein comprises an amino acid sequence having at least 95% sequence identity with the amino acid sequence of amino acids 138-736 of SEQ ID NO: 1, 2, 3, 4, 5, 6, 7, 9, 10, 11, 12, 13, 15, 16, or 17. In certain embodiments, the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G.

In certain embodiments, (a) the amino acid in the capsid protein corresponding to amino acid 626 of SEQ ID NO: 2 is G, and the amino acid in the capsid protein corresponding to amino acid 718 of SEQ ID NO: 2 is G;

(b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;

(c) the amino acid in the capsid protein corresponding to amino acid 505 of SEQ ID NO: 2 is R, and the amino acid in the capsid protein corresponding to amino acid 687 of SEQ ID NO: 2 is R;

(d) the amino acid in the capsid protein corresponding to amino acid 346 of SEQ ID NO: 2 is A, and the amino acid in the capsid protein corresponding to amino acid 505 of SEQ ID NO: 2 is R; or (e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 138-736 of SEQ ID NO: 1, 2, 3, 4, 5, 6, 7, 9, 10, 11, 12, 13, 15, 16, or 17.

In certain embodiments, the AAV Clade F capsid protein comprises an amino acid sequence having at least 95% sequence identity with the amino acid sequence of amino acids 1-736 of SEQ ID NO: 1, 2, 3, 4, 5, 6, 7, 8, 9, 10, 11, 12, 13, 15, 16, or 17. In certain embodiments, the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G.

In certain embodiments, (a) the amino acid in the capsid protein corresponding to amino acid 2 of SEQ ID NO: 2 is T, and the amino acid in the capsid protein corresponding to amino acid 312 of SEQ ID NO: 2 is Q;

(b) the amino acid in the capsid protein corresponding to amino acid 65 of SEQ ID NO: 2 is I, and the amino acid in the capsid protein corresponding to amino acid 626 of SEQ ID NO: 2 is Y;

(c) the amino acid in the capsid protein corresponding to amino acid 77 of SEQ ID NO: 2 is R, and the amino acid in the capsid protein corresponding to amino acid 690 of SEQ ID NO: 2 is K;

(d) the amino acid in the capsid protein corresponding to amino acid 119 of SEQ ID NO: 2 is L, and the amino acid in the capsid protein corresponding to amino acid 468 of SEQ ID NO: 2 is S;

(e) the amino acid in the capsid protein corresponding to amino acid 626 of SEQ ID NO: 2 is G, and the amino acid in the capsid protein corresponding to amino acid 718 of SEQ ID NO: 2 is G;

(f) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;

(g) the amino acid in the capsid protein corresponding to amino acid 505 of SEQ ID NO: 2 is R, and the amino acid in the capsid protein corresponding to amino acid 687 of SEQ ID NO: 2 is R;

(h) the amino acid in the capsid protein corresponding to amino acid 346 of SEQ ID NO: 2 is A, and the amino acid in the capsid protein corresponding to amino acid 505 of SEQ ID NO: 2 is R; or (i) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 1-736 of SEQ ID NO: 1, 2, 3, 4, 5, 6, 7, 8, 9, 10, 11, 12, 13, 15, 16, or 17.

In another aspect, the instant disclosure provides a pharmaceutical composition comprising an AAV described herein.

In another aspect, the instant disclosure provides a packaging system for recombinant preparation of an AAV, wherein the packaging system comprises: a Rep nucleotide sequence encoding one or more AAV Rep proteins; a Cap nucleotide sequence encoding one or more AAV Clade F capsid proteins described herein; and a correction genome described herein, wherein the packaging system is operative in a cell for enclosing the correction genome in the capsid to form the AAV.

In certain embodiments, the packaging system comprises a first vector comprising the Rep nucleotide sequence and the Cap nucleotide sequence, and a second vector comprising the correction genome. In certain embodiments, the Rep nucleotide sequence encodes an AAV2 Rep protein. In certain embodiments, the AAV2 Rep protein is 78/68 or Rep 68/52. In certain embodiments, the AAV2 Rep protein comprises an amino acid sequence having a minimum percent sequence identity to the AAV2 Rep amino acid sequence of SEQ ID NO: 22, wherein the minimum percent sequence identity is at least 70% across the length of the amino acid sequence encoding the AAV2 Rep protein.

In certain embodiments, the packaging system further comprises a third vector, wherein the third vector is a helper virus vector. In certain embodiments, the helper virus vector is an independent third vector. In certain embodiments, the helper virus vector is integral with the first vector. In certain embodiments, the helper virus vector is integral with the second vector. In certain embodiments, the third vector comprises genes encoding helper virus proteins. In certain embodiments, the helper virus is selected from the group consisting of adenovirus, herpes virus, vaccinia virus, and cytomegalovirus (CMV). In certain embodiments, the helper virus is adenovirus. In certain embodiments, the adenovirus genome comprises one or more adenovirus RNA genes selected from the group consisting of E1, E2, E4 and VA. In certain embodiments, the helper virus is herpes simplex virus (HSV). In certain embodiments, the HSV genome comprises one or more of HSV genes selected from the group consisting of UL5/8/52, ICPO, ICP4, ICP22 and UL30/UL42.

In certain embodiments, the first vector and the third vector are contained within a first transfecting plasmid. In certain embodiments, the nucleotides of the second vector and the third vector are contained within a second transfecting plasmid. In certain embodiments, the nucleotides of the first vector and the third vector are cloned into a recombinant helper virus. In certain embodiments, the nucleotides of the second vector and the third vector are cloned into a recombinant helper virus.

In another aspect, the instant disclosure provides a method for recombinant preparation of an AAV, the method comprising introducing the packaging system described herein into a cell under conditions operative for enclosing the correction genome in the capsid to form the AAV.

DETAILED DESCRIPTION

Figure 1A:
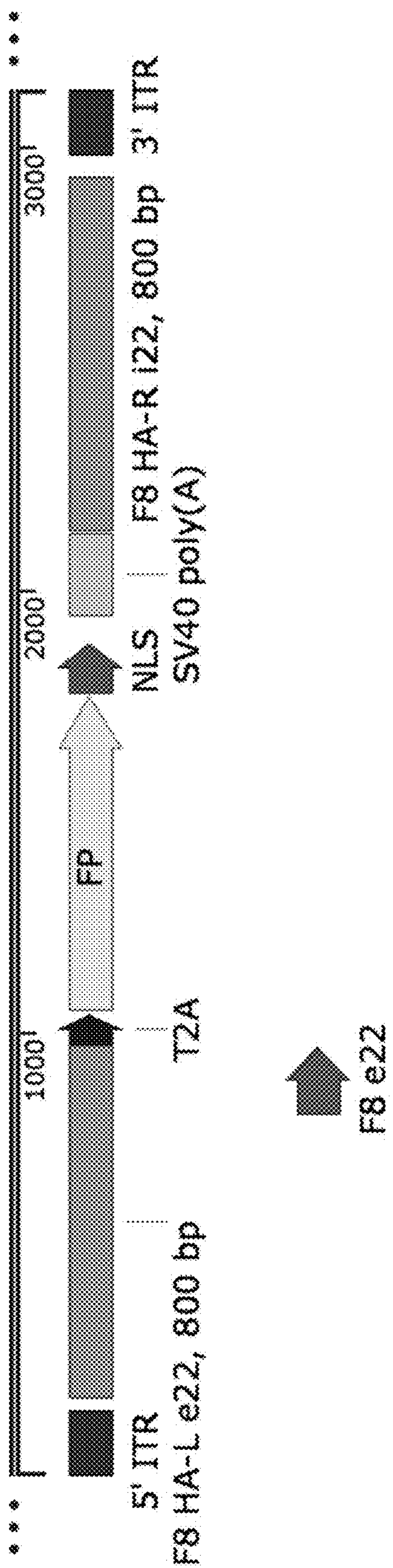
FIGS. 1A and 1B are maps of the VG-F8-002-FP and VG-F8-003-FP vectors, respectively.

The instant disclosure provided adeno-associated virus (AAV) compositions that can restore F8 gene function in a cell. Also provide are packaging systems for making the adeno-associated virus compositions.

I. Definitions

As used herein, the term "replication-defective adeno-associated virus" refers to an AAV comprising a genome lacking Rep and Cap genes.

As used herein, the term "F8 gene" refers to a wild-type or mutant gene encoding the FVIII protein, including but not limited to the coding regions, exons, introns, 5' UTR, 3' UTR, and transcriptional regulatory regions of the F8 gene. The human F8 gene is identified by Entrez Gene ID 2157. Wild-type human F8 gene is identified by nucleotides 5,001 to 191,936 of NCBI Reference Sequence: NG_011403.1. An exemplary nucleotide sequence of a full-length human F8 cDNA is identified by NCBI Reference No.: NM_000132.3. An exemplary amino acid sequence of a full-length human FVIII polypeptide, including its 19-amino acid signal peptide, is identified by NCBI Reference No.: NP_000123.1. Intron 22 of human F8 corresponds to nucleotides 131,648-164,496 (32,849 nt) of NCBI Reference Sequence: NG_011403.1.

As used herein, the term "correcting a mutation in an F8 gene" refers to the insertion, deletion, or substitution of one or more nucleotides at a target locus in a mutant F8 gene to create an F8 gene that is capable of expressing a wild-type FVIII polypeptide or a functional equivalent thereof. In certain embodiments, "correcting a mutation in an F8 gene" involves inserting a nucleotide sequence encoding at least a portion of a wild-type FVIII polypeptide or a functional equivalent thereof into the mutant F8 gene, such that a wild-type FVIII polypeptide or a functional equivalent thereof is expressed from the mutant F8 gene locus (e.g., under the control of an endogenous F8 gene promoter). A skilled person in the art will appreciate that the portion of a correction genome comprising the 5' homology arm, editing element, and 3' homology arm can be in the sense or antisense orientation relative to the target locus (e.g., the human F8 gene).

As used herein, the term "correction genome" refers to a recombinant AAV genome that is capable of integrating an editing element (e.g., one or more nucleotides or an internucleotide bond) via homologous recombination into a target locus to correct a genetic defect in an F8 gene. In certain embodiments, the target locus is in the human F8 gene. The skilled artisan will appreciate that the portion of a correction genome comprising the 5' homology arm, editing element, and 3' homology arm can be in the sense or antisense orientation relative to the target locus (e.g., the human F8 gene).

As used herein, the term "editing element" refers to the portion of a correction genome that when integrated at a target locus modifies the target locus. An editing element can mediate insertion, deletion, or substitution of one or more nucleotides at the target locus.

As used herein, the term "target locus" refers to a region of a chromosome or an internucleotide bond (e.g., a region or an internucleotide bond of the human F8 gene) that is modified by an editing element.

As used herein, the term "homology arm" refers to a portion of a correction genome positioned 5' or 3' to an editing element that is substantially identical to the genome flanking a target locus. In certain embodiments, the target locus is in a human F8 gene, and the homology arm comprises a sequence substantially identical to the genome flanking the target locus.

As used herein, the term "Clade F capsid protein" refers to an AAV VP1, VP2, or VP3 capsid protein that has at least 90% identity with the VP1, VP2, or VP3 amino acid sequences set forth, respectively, in amino acids 1-736, 138-736, and 203-736 of SEQ ID NO: 1 herein. As used herein, the identity between two nucleotide sequences or between two amino acid sequences is determined by the number of identical nucleotides or amino acids in alignment divided by the full length of the longer nucleotide or amino acid sequence.

As used herein, the term "a disease or disorder associated with an F8 gene mutation" refers to any disease or disorder caused by, exacerbated by, or genetically linked with mutation of an F8 gene. In certain embodiments, the disease or disorder associated with an F8 gene mutation is hemophilia A.

As used herein, the term "coding sequence" refers to the portion of a complementary DNA (cDNA) that encodes a polypeptide, starting at the start codon and ending at the stop codon. A gene may have one or more coding sequences due to alternative splicing and/or alternative translation initiation. A coding sequence may either be wild-type or silently altered. An exemplary full-length wild-type F8 coding sequence is identified by nucleotides 172 to 7,227 of NCBI Reference No.: NM_000132.3. An exemplary portion of wild-type F8 coding sequence, corresponding to exons 22-26, is set forth in SEQ ID NO: 26.

As used herein, the term "silently altered" or "silent alteration" refers to alteration of a coding sequence of a gene (e.g., by nucleotide substitution) without changing the amino acid sequence of the polypeptide encoded by the gene. In certain embodiments, silent alteration increases the expression level of a coding sequence. In certain embodiments, silent alteration reduces off-targeting to undesired genomic loci.

As used herein, the term "polyadenylation sequence" refers to a DNA sequence that when transcribed into RNA constitutes a polyadenylation signal sequence. The polyadenylation sequence can be native (e.g., from the F8 gene) or exogenous. The exogenous polyadenylation sequence can be a mammalian or a viral polyadenylation sequence (e.g., an SV40 polyadenylation sequence).

In the instant disclosure, nucleotide positions in an F8 gene are specified relative to the first nucleotide of the start codon. The first nucleotide of a start codon is position 1; the nucleotides 5' to the first nucleotide of the start codon have negative numbers; the nucleotides 3' to the first nucleotide of the start codon have positive numbers. A skilled person will appreciate that a gene may have multiple start codons due to alternative splicing and/or alternative translation initiation. As used herein, nucleotide 1 of the human F8 gene is nucleotide 5172 of the NCBI Reference Sequence: NG_011403.1. The nucleotide adjacently 5' to the start codon is nucleotide −1. Thus, nucleotide −1 of the human F8 gene is nucleotide 5173 of the NCBI Reference Sequence: NG_011403.1. As used herein, nucleotide 1 of the mouse F8 gene is nucleotide 75,383,525 of the NCBI Reference Sequence: NC_000086.7 on the negative strand.

In the instant disclosure, exons and introns in an F8 gene are specified relative to the exon encompassing the first nucleotide of the start codon, which is nucleotide 5,172 of the NCBI Reference Sequence: NG_011403.1. The exon encompassing the first nucleotide of the start codon is exon 1. Exons 3' to exon 1 are from 5' to 3': exon 2, exon 3, etc. Introns 3' to exon 1 are from 5' to 3': intron 1, intron 2, etc. Accordingly, the F8 gene comprises from 5' to 3': exon 1, intron 1, exon 2, intron 2, exon 3, etc. A skilled person will appreciate that a gene may be transcribed into multiple different mRNAs. As such, a gene (e.g., F8) may have multiple different sets of exons and introns. As used herein, exon 1 of the human F8 gene is nucleotides 5,001-5,314 of the NCBI Reference Sequence: NG_011403.1. An exemplary intron 1 of the human F8 gene is nucleotides 5,315-28,123 of the NCBI Reference Sequence: NG_011403.1. An exemplary exon 22 of the human F8 gene is nucleotides 131,492-131,647 (156 nt) of the NCBI Reference Sequence: NG_011403.1. An exemplary intron 22 of the human F8 gene is nucleotides 131,648-164,496 (32,849 nt) of the NCBI Reference Sequence: NG_011403.1. An exemplary exon 23 of the human F8 gene is nucleotides 164,497-164,641 (145 nt) of the NCBI Reference Sequence: NG_011403.1. An exemplary intron 23 of the human F8 gene is nucleotides 164,642-165,857 (1216 nt) of the NCBI Reference Sequence: NG_011403.1. An exemplary exon 24 of the human F8 gene is nucleotides 165,858-166,006 (149 nt) of the NCBI Reference Sequence: NG_011403.1. An exemplary intron 24 of the human F8 gene is nucleotides 166,007-167,115 (1109 nt) of the NCBI Reference Sequence: NG_011403.1. An exemplary exon 25 of the human F8 gene is nucleotides 167,116-167,292 (177 nt) of the NCBI Reference Sequence: NG_011403.1. An exemplary intron 25 of the human F8 gene is nucleotides 167,293-189,971 (22,679 nt) of the NCBI Reference Sequence: NG_011403.1. An exemplary exon 26 of the human F8 gene is nucleotides 189,972-191,936 (1965 nt) of the NCBI Reference Sequence: NG_011403.1.

As used herein, the term "integration" refers to introduction of an editing element into a target locus of a target gene by homologous recombination between a correction genome and the target gene. Integration of an editing element can result in substitution, insertion and/or deletion of one or more nucleotides in a target gene. For example, in certain embodiments, the term "integration" refers to introduction of an editing element into a target locus of an F8 gene by homologous recombination between a correction genome and the F8 gene. Integration of an editing element can result in substitution, insertion and/or deletion of one or more nucleotides in an F8 gene.

As used herein, the term "integration efficiency of the editing element into the target locus" refers to the percentage of cells in a transduced population in which integration of the editing element into the target locus has occurred.

As used herein, the term "allelic frequency of integration of the editing element into the target locus" refers to the percentage of alleles in a population of transduced cells in which integration of the editing element into the target locus has occurred.

As used herein, the term "standard AAV transduction conditions" refers to transduction of B lymphoblastoid cells with an AAV at a multiplicity of infection (MOI) of $1.5\times10^5$, wherein the cells are cultured in RPMI-1640 media supplemented with 15% fetal calf serum (FCS), and 2 mmol/L L-glutamine at 37° C. in an incubator environment of 5% carbon dioxide ($CO_2$), wherein the cells in log phase growth are seeded at approximately 200,000 cells per ml and infected on the same day, wherein the AAV is formulated in phosphate buffered saline (PBS), and wherein the AAV is added to the cell culture medium containing the B lymphoblastoid cells in a volume that is less than or equal to 5% of the volume of the culture medium.

As used herein, "exogenous polyadenylation sequence" refers to a polyadenylation sequence not identical or substantially identical to the endogenous polyadenylation sequence of a gene (e.g., human gene). For example, in certain embodiments, "exogenous polyadenylation sequence" refers to a polyadenylation sequence not identical or substantially identical to the endogenous polyadenylation sequence of an F8 gene (e.g., human F8 gene). In certain embodiments, an exogenous polyadenylation sequence is a polyadenylation sequence of a non-F8 gene in the same species (e.g., human). In certain embodiments, an exogenous polyadenylation sequence is a polyadenylation sequence of a different species (e.g., a virus).

As used herein, the term "effective amount" in the context of the administration of an AAV to a subject refers to the amount of the AAV that achieves a desired prophylactic or therapeutic effect.

II. Adeno-Associated Virus Compositions

In one aspect, provided herein are novel replication-defective AAV compositions useful for restoring F8 expression in cells with reduced or otherwise defective F8 gene function. Such AAV compositions are highly efficient at correcting mutations in the F8 gene or restoring F8 expression, and do not require cleavage of the genome at the target locus by the action of an exogenous nuclease (e.g., a meganuclease, a zinc finger nuclease, a transcriptional activator-like nuclease (TALEN), or an RNA-guided nuclease such as a Cas9) to facilitate such correction. Accordingly, in certain embodiments, the AAV composition disclosed herein does not comprise an exogenous nuclease or a nucleotide sequence that encodes an exogenous nuclease.

In certain embodiments, the AAV disclosed herein comprise: an AAV capsid comprising an AAV capsid protein; and a correction genome for editing a target locus in an F8 gene.

The AAV capsid proteins that can be used in the AAV compositions disclosed herein include without limitation AAV capsid proteins and derivatives thereof of Clade A AAVs, Clade B AAVs, Clade C AAVs, Clade D AAVs, Clade E AAVs, and Clade F AAVs. In certain embodiments, the AAV capsid protein is an AAV capsid protein or a derivative thereof of AAV1, AAV2, AAV3, AAV4, AAV5, AAV6, AAV7, AAV8, AAV9, or AAVrh10.

In certain embodiments, the AAV capsid protein is a Clade F AAV capsid protein. Any AAV Clade F capsid protein or derivative thereof can be used in the AAV compositions disclosed herein. For example, in certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 203-736 of SEQ ID NO: 1, 2, 3, 4, 5, 6, 7, 8, 9, 10, 11, 12, 13, 15, 16, or 17. In certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 203-736 of SEQ ID NO: 1, 2, 3, 4, 5, 6, 7, 8, 9, 10, 11, 12, 13, 15, 16, or 17, wherein: the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 203-736 of SEQ ID NO: 1, 2, 3, 4, 6, 7, 10, 11, 12, 13, 15, 16, or 17.

For example, in certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 138-736 of SEQ ID NO: 1, 2, 3, 4, 5, 6, 7, 8, 9, 10, 11, 12, 13, 15, 16, or 17. In certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 138-736 of SEQ ID NO: 1, 2, 3, 4, 5, 6, 7, 8, 9, 10, 11, 12, 13, 15, 16, or 17, wherein: the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 138-736 of SEQ ID NO: 1, 2, 3, 4, 5, 6, 7, 9, 10, 11, 12, 13, 15, 16, or 17.

For example, in certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 1-736 of SEQ ID NO: 1, 2, 3, 4, 5, 6, 7, 8, 9, 10, 11, 12, 13, 15, 16, or 17. In certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 1-736 of SEQ ID NO: 1, 2, 3, 4, 5, 6, 7, 8, 9, 10, 11, 12, 13, 15, 16, or 17, wherein: the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 2 of SEQ ID NO: 2 is T, and the amino acid in the capsid protein corresponding to amino acid 312 of SEQ ID NO: 2 is Q. In certain embodiments, the amino acid in the capsid protein corresponding to amino acid 65 of SEQ ID NO: 2 is I, and the amino acid in the capsid protein corresponding to amino acid 626 of SEQ ID NO: 2 is Y. In certain embodiments, the amino acid in the capsid protein corresponding to amino acid 77 of SEQ ID NO: 2 is R, and the amino acid in the capsid protein corresponding to amino acid 690 of SEQ ID NO: 2 is K. In certain embodiments, the amino acid in the capsid protein corresponding to amino acid 119 of SEQ ID NO: 2 is L, and the amino acid in the capsid protein corresponding to amino acid 468 of SEQ ID NO: 2 is S. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 1-736 of SEQ ID NO: 1, 2, 3, 4, 5, 6, 7, 8, 9, 10, 11, 12, 13, 15, 16, or 17.

In certain embodiments, the AAV capsid comprises two or more of: a) a Clade F capsid protein comprising the amino acid sequence of amino acids 203-736 of SEQ ID NO: 1, 2, 3, 4, 5, 6, 7, 8, 9, 10, 11, 12, 13, 14, 15, 16, or 17; b) a Clade F capsid protein comprising the amino acid sequence of amino acids 138-736 of SEQ ID NO: 1, 2, 3, 4, 5, 6, 7, 8, 9, 10, 11, 12, 13, 14, 15, 16, or 17; and c) a Clade F capsid protein comprising the amino acid sequence of amino acids 1-736 of SEQ ID NO: 1, 2, 3, 4, 5, 6, 7, 8, 9, 10, 11, 12, 13, 14, 15, 16, or 17. In certain embodiments, the AAV capsid comprises: a) a Clade F capsid protein having an amino acid sequence consisting of amino acids 203-736 of SEQ ID NO: 1, 2, 3, 4, 5, 6, 7, 8, 9, 10, 11, 12, 13, 14, 15, 16, or 17; b) a Clade F capsid protein having an amino acid sequence consisting of amino acids 138-736 of SEQ ID NO: 1, 2, 3, 4, 5, 6, 7, 8, 9, 10, 11, 12, 13, 14, 15, 16, or 17; and c) a Clade F capsid protein having an amino acid sequence consisting of amino acids 1-736 of SEQ ID NO: 1, 2, 3, 4, 5, 6, 7, 8, 9, 10, 11, 12, 13, 14, 15, 16, or 17.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 8; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 8; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 8. In certain embodiments, the AAV capsid comprises one or more of: (a) a Clade F capsid protein comprising the amino acid sequence of amino acids 203-736 of SEQ ID NO: 8; (b) a Clade F capsid protein comprising the amino acid sequence of amino acids 138-736 of SEQ ID NO: 8; and (c) a Clade F capsid protein comprising the amino acid sequence of amino acids 1-736 of SEQ ID NO: 8. In certain embodiments, the AAV capsid comprises two or more of: (a) a Clade F capsid protein comprising the amino acid sequence of amino acids 203-736 of SEQ ID NO: 8; (b) a Clade F capsid protein comprising the amino acid sequence of amino acids 138-736 of SEQ ID NO: 8; and (c) a Clade F capsid protein comprising the amino acid sequence of amino acids 1-736 of SEQ ID NO: 8. In certain embodiments, the AAV capsid comprises: (a) a Clade F capsid protein having an amino acid sequence consisting of amino acids 203-736 of SEQ ID NO: 8; (b) a Clade F capsid protein having an amino acid sequence consisting of amino acids 138-736 of SEQ ID NO: 8; and (c) a Clade F capsid protein having an amino acid sequence consisting of amino acids 1-736 of SEQ ID NO: 8.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 11; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 11; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 11. In certain embodiments, the AAV capsid comprises one or more of: (a) a Clade F capsid protein comprising the amino acid sequence of amino acids 203-736 of SEQ ID NO: 11; (b) a Clade F capsid protein comprising the amino acid sequence of amino acids 138-736 of SEQ ID NO: 11; and (c) a Clade F capsid protein comprising the amino acid sequence of amino acids 1-736 of SEQ ID NO: 11. In certain embodiments, the AAV capsid comprises two or more of: (a) a Clade F capsid protein comprising the amino acid sequence of amino acids 203-736 of SEQ ID NO: 11; (b) a Clade F capsid protein comprising the amino acid sequence of amino acids 138-736 of SEQ ID NO: 11; and (c) a Clade F capsid protein comprising the amino acid sequence of amino acids 1-736 of SEQ ID NO: 11. In certain embodiments, the AAV capsid comprises: (a) a Clade F capsid protein having an amino acid sequence consisting of amino acids 203-736 of SEQ ID NO: 11; (b) a Clade F capsid protein having an amino acid sequence consisting of amino acids 138-736 of SEQ ID NO: 11; and (c) a Clade F capsid protein having an amino acid sequence consisting of amino acids 1-736 of SEQ ID NO: 11.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 13; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 13; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 13. In certain embodiments, the AAV capsid comprises one or more of: (a) a Clade F capsid protein comprising the amino acid sequence of amino acids 203-736 of SEQ ID NO: 13; (b) a Clade F capsid protein comprising the amino acid sequence of amino acids 138-736 of SEQ ID NO: 13; and (c) a Clade F capsid protein comprising the amino acid sequence of amino acids 1-736 of SEQ ID NO: 13. In certain embodiments, the AAV capsid comprises two or more of: (a) a Clade F capsid protein comprising the amino acid sequence of amino acids 203-736 of SEQ ID NO: 13; (b) a Clade F capsid protein comprising the amino acid sequence of amino acids 138-736 of SEQ ID NO: 13; and (c) a Clade F capsid protein comprising the amino acid sequence of amino acids 1-736 of SEQ ID NO: 13. In certain embodiments, the AAV capsid comprises: (a) a Clade F capsid protein having an amino acid sequence consisting of amino acids 203-736 of SEQ ID NO: 13; (b) a Clade F capsid protein having an amino acid sequence consisting of amino acids 138-736 of SEQ ID NO: 13; and (c) a Clade F capsid protein having an amino acid sequence consisting of amino acids 1-736 of SEQ ID NO: 13.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 16; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 16; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 16. In certain embodiments, the AAV capsid comprises one or more of: (a) a Clade F capsid protein comprising the amino acid sequence of amino acids 203-736 of SEQ ID NO: 16; (b) a Clade F capsid protein comprising the amino acid sequence of amino acids 138-736 of SEQ ID NO: 16; and (c) a Clade F capsid protein comprising the amino acid sequence of amino acids 1-736 of SEQ ID NO: 16. In certain embodiments, the AAV capsid comprises two or more of: (a) a Clade F capsid protein comprising the amino acid sequence of amino acids 203-736 of SEQ ID NO: 16; (b) a Clade F capsid protein comprising the amino acid sequence of amino acids 138-736 of SEQ ID NO: 16; and (c) a Clade F capsid protein comprising the amino acid sequence of amino acids 1-736 of SEQ ID NO: 16. In certain embodiments, the AAV capsid comprises: (a) a Clade F capsid protein having an amino acid sequence consisting of amino acids 203-736 of SEQ ID NO: 16; (b) a Clade F capsid protein having an amino acid sequence consisting of amino acids 138-736 of SEQ ID NO: 16; and (c) a Clade F capsid protein having an amino acid sequence consisting of amino acids 1-736 of SEQ ID NO: 16.

Correction genomes useful in the AAV compositions disclosed herein generally comprise: (i) an editing element for editing a target locus in an F8 gene, (ii) a 5' homology arm nucleotide sequence 5' to the editing element having homology to a first genomic region 5' to the target locus, and (iii) a 3' homology arm nucleotide sequence 3' to the editing element having homology to a second genomic region 3' to the target locus, wherein the portion of the correction genome comprising the 5' homology arm, editing element, and 3' homology arm can be in the sense or antisense orientation relative to the F8 gene locus. In certain embodiments, the correction genome further comprises a 5' inverted terminal repeat (5' ITR) nucleotide sequence 5' to the 5' homology arm nucleotide sequence, and a 3' inverted terminal repeat (3' ITR) nucleotide sequence 3' to the 3' homology arm nucleotide sequence.

Editing elements used in the correction genomes disclosed herein can mediate insertion, deletion, or substitution of one or more nucleotides at the target locus.

In certain embodiments, when correctly integrated by homologous recombination at the target locus, the editing element corrects a mutation in an F8 gene back to the wild-type F8 sequence or a functional equivalent thereof. In certain embodiments, the editing element comprises a portion of an F8 coding sequence (e.g., a portion of a wild-type FVIII coding sequence or a portion of a silently altered F8 coding sequence).

In certain embodiments, the editing element comprises a wild-type or silently altered sequence of exons 23-26 of an F8 gene (e.g., the human F8 gene). In certain embodiments, the editing element comprises at least a portion of an F8 coding sequence. For example, in certain embodiments, the editing element comprises a portion of an F8 coding sequence, and may optionally further comprise an exogenous polyadenylation sequence 3' to the coding sequence. In certain embodiments, the portion of the F8 coding sequence comprises the sequences of exons 23-26 of an F8 gene, optionally further comprising the sequences of one or more of exons 15-22 in the same order as in a genome (e.g., human genome). In certain embodiments, the portion of the F8 coding sequence comprises the sequences of exons 15-26, 16-26, 17-26, 18-26, 19-26, 20-26, 21-26, or 22-26 of an F8 gene. In certain embodiments, the portion of the F8 coding sequence comprises the sequences of exons 22-26 (SEQ ID NO: 26). In certain embodiments, the editing element comprises the sequence set forth in SEQ ID NO: 33.

In certain embodiments, the target locus is an internucleotide bond or a nucleotide sequence adjacently 3' to the last nucleotide of any one of exons 15-22. In certain embodiments, integration of the editing element in a genome (e.g., human genome) results in generation of a sequence comprising exons 1 to X and introns 1 to X−1 (X minus 1) of an F8 gene (e.g., the human F8 gene), and a portion of an F8 coding sequence (e.g., a human F8 coding sequence) comprising the sequences of exons X+1 (X plus 1) to 26 or a silently altered variant thereof, wherein X is any number selected from 14, 15, 16, 17, 18, 19, 20, 21, and 22, and wherein the exons and introns in the editing element are positioned in the same order as in the genome. In certain embodiments, X is 22.

In certain embodiments, the portion of the F8 coding sequence encodes an amino acid sequence comprising or consisting of the sequence set forth in SEQ ID NO: 25. In certain embodiments, the nucleic acid sequence encoding SEQ ID NO: 25 is wild-type (e.g., having the sequence set forth in SEQ ID NO: 26). In certain embodiments, the nucleic acid sequence encoding SEQ ID NO: 25 is silently altered. In certain embodiments, the target locus is an internucleotide bond or a nucleotide sequence adjacently 3' to the last nucleotide of exon 22 of an F8 gene (e.g., the internucleotide bond between nucleotides 126,476 and 126, 477 of the human F8 gene, or a sequence starting at nucleotide 126,477 of the human F8 gene), wherein integration of the editing element results in generation of a sequence comprising 5' to 3': exon 1, intron 1, exon 2, intron 2, exon 3, intron 3, exon 4, intron 4, exon 5, intron 5, exon 6, intron 6, exon 7, intron 7, exon 8, intron 8, exon 9, intron 9, exon 10, intron 10, exon 11, intron 11, exon 12, intron 12, exon 13, intron 13, exon 14, intron 14, exon 15, intron 15, exon 16, intron 16, exon 17, intron 17, exon 18, intron 18, exon 19, intron 19, exon 20, intron 20, exon 21, intron 21, exon 22, exon 23, exon 24, exon 25, and exon 26 of an F8 gene at the F8 gene locus, wherein the sequence of each of exon 23, exon 24, exon 25, and exon 26 may be independently wild-type or silently altered.

In certain embodiments, the editing element comprises a portion of an F8 coding sequence (e.g., a portion of a wild-type F8 coding sequence, or a portion of a silently altered F8 coding sequence). Such editing elements can further comprise a splice acceptor site and/or an exogenous polyadenylation sequence. In certain embodiments, the editing element comprises 5' to 3': a splice acceptor site; a portion of an F8 coding sequence (e.g., a portion of a wild-type F8 coding sequence, or a portion of a silently altered F8 coding sequence); and an exogenous polyadenylation sequence. In certain embodiments, the portion of the F8 coding sequence comprises the sequences of exons 23-26 of an F8 gene, optionally further comprising the sequences of one or more of exons 15-22 in the same order as in a genome (e.g., human genome). In certain embodiments, the portion of the F8 coding sequence comprises the sequences of exons 15-26, 16-26, 17-26, 18-26, 19-26, 20-26, 21-26, or 22-26 of an F8 gene.

In certain embodiments, the aforementioned editing element can be integrated into an intron of the F8 gene (e.g., the nucleotide 5' to the target locus is in an intron of the F8 gene, or the 5'-most nucleotide of the target locus is in an intron of the F8 gene) by homologous recombination to produce a recombinant sequence comprising 5' to 3': a portion of the F8 gene 5' to the target locus including the endogenous splice donor site but not the endogenous splice acceptor site of the intron; a splice acceptor site; a portion of an F8 coding sequence (e.g., a portion of a wild-type F8 coding sequence, or a portion of a silently altered F8 coding sequence); and an exogenous polyadenylation sequence. Expression of this recombinant sequence produces a polypeptide comprising the amino acid sequence encoded by the portion of the F8 gene 5' to the target locus fused to a polypeptide comprising the partial amino acid sequence of the FVIII polypeptide encoded by the portion of F8 coding sequence.

In certain embodiments, the nucleotide adjacently 5' to the target locus is in an intron of the F8 gene. In certain embodiments, the target locus is an internucleotide bond in any one of introns 15-22. In certain embodiments, the target locus is a nucleotide sequence adjacently 3' to a nucleotide in any one of introns 15-22. In certain embodiments, integration of the editing element in a genome (e.g., human genome) results in generation of a sequence comprising exons 1 to X, introns 1 to X−1 (X minus 1) and a portion of intron X, a splice acceptor, and a portion of an F8 coding sequence (e.g., a human F8 coding sequence) comprising the sequences of exons X+1 (X plus 1) to 26 or a silently altered variant thereof, wherein X is any number selected from 14, 15, 16, 17, 18, 19, 20, 21, and 22, wherein the exons and introns in the editing element are positioned in the same order as in the genome, and wherein the splice acceptor is between the portion of intron X and the portion of F8 coding sequence. In certain embodiments, X is 22.

In certain embodiments, the nucleotide adjacently 5' to the target locus is in intron 22 of the F8 gene. In certain embodiments, the target locus is an internucleotide bond in intron 22 of the F8 gene. In certain embodiments, the target locus is a sequence in the F8 gene wherein the nucleotide adjacently 5' to this sequence is in intron 22 of the F8 gene, wherein the 3' end of this sequence can be any downstream nucleotide in the F8 gene.

In certain embodiments, one or more portions of an F8 coding sequence within an editing element can be silently altered to be non-identical to the corresponding sequences of the wild-type F8 gene. Silent alteration can be conducted by any method known in the art (e.g., as described in Mauro & Chappell (2014) *Trends Mol Med.* 20(11):604-13, which is incorporated by reference herein in its entirety). An exemplary partial silently altered F8 coding sequence is set forth in SEQ ID NO: 33.

Accordingly, in certain embodiments, the editing element comprises an F8 coding sequence that has been silently altered to be less than 100% (e.g., less than 95%, 90%, 85%, 80%, 75%, 70%, 65%, 60%, 55%, or 50%) identical to the corresponding exons of the wild-type F8 gene. In certain embodiments, the editing element comprises a nucleotide sequence that has been silently altered to be less than 100% (e.g., less than 95%, 90%, 85%, 80%, 75%, 70%, 65%, 60%, 55%, or 50%) identical to the sequence set forth in SEQ ID NO: 26. Such editing elements can further comprise an exogenous polyadenylation sequence 3' to the F8 gene coding sequence.

In certain embodiments, the editing element further comprises a polyadenylation sequence 3' to the portion of F8 coding sequence. In certain embodiments, the polyadenylation sequence is an exogenous polyadenylation sequence. In certain embodiments, the exogenous polyadenylation sequence is an SV40 polyadenylation sequence. In certain embodiments, the SV40 polyadenylation sequence has a nucleotide sequence set forth in SEQ ID NO: 23, 35, 36, or 37.

Any and all of the editing elements disclosed herein can further include a restriction endonuclease site not present in the wild-type F8 gene. Such restriction endonuclease sites allow for identification of cells that have integration of the editing element at the target locus based upon restriction fragment length polymorphism analysis or by nucleic sequencing analysis of the target locus and its flanking regions, or a nucleic acid amplified therefrom.

Any and all of the editing elements disclosed herein can comprise one or more nucleotide alterations that cause one or more amino acid mutations in FVIII polypeptide when integrated into the target locus. In certain embodiments, the mutant FVIII polypeptide is a functional equivalent of the wild-type FVIII polypeptide, i.e., can function as a wild-type FVIII polypeptide. In certain embodiments, the functionally equivalent FVIII polypeptide further comprises at least one characteristic not found in the wild-type FVIII polypeptide, e.g., the ability to resist protein degradation.

In certain embodiments, an editing element as described herein comprises at least 0, 1, 2, 10, 100, 200, 500, 1000, 1500, 2000, 3000, 4000, or 5000 nucleotides. In certain embodiments, the editing element comprises or consists of 1 to 5000, 1 to 4500, 1 to 4000, 1 to 3000, 1 to 2000, 1 to 1000, 1 to 500, 1 to 200, 1 to 100, 1 to 50, or 1 to 10 nucleotides.

In certain embodiments, an editing element as described herein comprises or consists of a partial F8 coding sequence (e.g., exons 22-26 of human F8 coding sequence, or nucleotides 4 to 783 of SEQ ID NO: 31), a 5' untranslated region (UTR), a 3' UTR, a promoter, a splice donor, a splice acceptor, a sequence encoding a non-coding RNA, an insulator, a gene, or a combination thereof.

In certain embodiments, the editing element comprises a nucleic acid sequence at least 70%, 75%, 80%, 85%, 90%, 91%, 92%, 93%, 94%, 95%, 96%, 97%, 98%, 99%, or 99.5% identical to the sequence set forth in SEQ ID NO: 33. In certain embodiments, the editing element comprises the nucleic acid sequence set forth in SEQ ID NO: 33.

Homology arms used in the correction genomes disclosed herein can be directed to any region of the F8 gene or a gene nearby on the genome. The precise identity and positioning of the homology arms are determined by the identity of the editing element and/or the target locus.

Homology arms employed in the correction genomes disclosed herein are substantially identical to the genome flanking a target locus (e.g., a target locus in the F8 gene). In certain embodiments, the 5' homology arm has at least about 90% (e.g., at least about 95%, 96%, 97%, 98%, 99%, or 99.5%) nucleotide sequence identity to a first region 5' to the target locus. In certain embodiments, the 5' homology arm has 100% nucleotide sequence identity to the first region. In certain embodiments, the 3' homology arm has at least about 90% (e.g., at least about 95%, 96%, 97%, 98%, 99%, or 99.5%) nucleotide sequence identity to a second region 3' to the target locus. In certain embodiments, the 3' homology arm has 100% nucleotide sequence identity to the second region. In certain embodiments, the 5' and 3' homology arms are each at least about 90% (e.g., at least about 95%, 96%, 97%, 98%, 99%, or 99.5%) identical to the first and second regions flanking the target locus (e.g., a target locus in the F8 gene), respectively. In certain embodiments, the 5' and 3' homology arms are each 100% identical to the first and second regions flanking the target locus (e.g., a target locus in the F8 gene), respectively. In certain embodiments, differences in nucleotide sequences of the 5' homology arm and/or the 3' homology arm and the corresponding regions the genome flanking a target locus comprise, consist essentially of, or consist of non-coding differences in nucleotide sequences.

The skilled worker will appreciate that homology arms do not need to be 100% identical to the genomic sequence flanking the target locus to be able to mediate integration of an editing element into that target locus by homologous recombination. For example, the homology arms can comprise one or more genetic variations in the human population, and/or one or more modifications (e.g., nucleotide substitutions, insertions, or deletions) designed to improve expression level or specificity. Human genetic variations include both inherited variations and de novo variations that are private to the target genome, and encompass simple nucleotide polymorphisms, insertions, deletions, rearrangements, inversions, duplications, micro-repeats, and combinations thereof. Such variations are known in the art, and can be found, for example, in the databases of dnSNP (see Sherry et al. Nucleic Acids Res. 2001; 29(1):308-11), the Database of Genomic Variants (see Nucleic Acids Res. 2014; 42(Database issue):D986-92), ClinVar (see Nucleic Acids Res. 2014; 42(Database issue): D980-D985), Genbank (see Nucleic Acids Res. 2016; 44(Database issue): D67-D72), ENCODE (genome.ucsc.edu/encode/terms.html), JASPAR (see Nucleic Acids Res. 2018; 46(D1): D260-D266), and PROMO (see Messeguer et al. Bioinformatics 2002; 18(2):333-334; Farré et al. Nucleic Acids Res. 2003; 31(13):3651-3653), each of which is incorporated herein by reference. The skilled worker will further appreciate that in situations where a homology arm is not 100% identical to the genomic sequence flanking the target locus, homologous recombination between the homology arm and the genome may alter the genomic sequence flanking the target locus such that it becomes identical to the sequence of the homology arm used.

In certain embodiments, the first genomic region 5' to the target locus is located in a first editing window, wherein the first editing window consists of the nucleotide sequence set forth in SEQ ID NO: 31, 32, or 34. In certain embodiments, the second genomic region 3' to the target locus is located in a second editing window, wherein the second editing window consists of the nucleotide sequence set forth in SEQ ID NO: 31, 32, or 34.

In certain embodiments, the first and second editing windows are different. In certain embodiments, the first editing window is located 5' to the second editing window. In certain embodiments, the first genomic region consists of a portion of the sequence of the first editing window in which the first genomic region is located. In certain embodiments, the first genomic region consists of the sequence of the first editing window in which the first genomic region is located. In certain embodiments, the second genomic region consists of a portion of the sequence of the second editing window in which the second genomic region is located. In certain embodiments, the second genomic region consists of the sequence of the second editing window in which the second genomic region is located. In certain embodiments, the first editing window consists of the nucleotide sequence set forth in SEQ ID NO: 31; and the second editing window consists of the nucleotide sequence set forth in SEQ ID NO: 32. In certain embodiments, the first genomic region 5' to the target locus consists of the sequence set forth in SEQ ID NO: 31. In certain embodiments, the second genomic region 3' to the target locus consists of the sequence set forth in SEQ ID NO: 32. In certain embodiments, the first genomic region 5' to the target locus and the second genomic region 3' to the target locus consist of the sequences set forth in SEQ ID NOs: 31 and 32, respectively.

In certain embodiments, the 5' homology arm consists of a nucleotide sequence at least about 90% (e.g., at least about 95%, 96%, 97%, 98%, 99%, or 99.5%) identical to the nucleotide sequence of SEQ ID NO: 31. In certain embodiments, the 5' homology arm consists of the nucleotide sequence set forth in SEQ ID NO: 31. In certain embodiments, the 3' homology arm consists of a nucleotide sequence at least about 90% (e.g., at least about 95%, 96%, 97%, 98%, 99%, or 99.5%) identical to the nucleotide sequence of SEQ ID NO: 32. In certain embodiments, the 3' homology arm consists of the nucleotide sequence set forth in SEQ ID NO: 32. In certain embodiments, the 5' and 3' homology arms consist of nucleotide sequences at least about 90% (e.g., at least about 95%, 96%, 97%, 98%, 99%, or 99.5%) identical to the nucleotide sequences of SEQ ID NOs: 31 and 32, respectively. In certain embodiments, the 5' and 3' homology arms consist of nucleotide sequences set forth in SEQ ID NOs: 31 and 32, respectively.

In certain embodiments, the first and second editing windows are the same. In certain embodiments, the target locus is an internucleotide bond or a nucleotide sequence in the editing window, wherein the first genomic region consists of a first portion of the editing window 5' to the target locus, and the second genomic region consists of a second portion of the editing window 3' to the target locus. In certain embodiments, the first portion of the editing window consists of the sequence from the 5' end of the editing window to the nucleotide adjacently 5' to the target locus. In certain embodiments, the second portion of the editing window consists of the sequence from the nucleotide adjacently 3' to the target locus to the 3' end of the editing window. In certain embodiments, the first portion of the editing window consists of the sequence from the 5' end of the editing window to the nucleotide adjacently 5' to the target locus, and the second portion of the editing window consists of the sequence from the nucleotide adjacently 3' to the target locus to the 3' end of the editing window. In certain embodiments, the editing window consists of the nucleotide sequence set forth in SEQ ID NO: 34. In certain embodiments, the first and second portions of the editing windows have substantially equal lengths (e.g., the ratio of the length of the shorter portion to the length of the longer portion is greater than 0.5, 0.55, 0.6, 0.65, 0.7, 0.75, 0.8, 0.85, 0.9, 0.95, 0.96, 0.97, 0.98, or 0.99).

In certain embodiments, the 5' homology arm consists of a nucleotide sequence at least about 90% (e.g., at least about 95%, 96%, 97%, 98%, 99%, or 99.5%) identical to a first portion of the nucleotide sequence of SEQ ID NO: 34. In certain embodiments, the 5' homology arm consists of a first portion of the nucleotide sequence of SEQ ID NO: 34. In certain embodiments, the 3' homology arm consists of a nucleotide sequence at least about 90% (e.g., at least about 95%, 96%, 97%, 98%, 99%, or 99.5%) identical to a second portion of the nucleotide sequence of SEQ ID NO: 34. In certain embodiments, the 3' homology arm consists of a second portion of the nucleotide sequence of SEQ ID NO: 34. In certain embodiments, the first portion is 5' to the second portion in SEQ ID NO: 34. In certain embodiments, the 5' and 3' homology arms consist of nucleotide sequences at least about 90% (e.g., at least about 95%, 96%, 97%, 98%, 99%, or 99.5%) identical to a first portion and a second portion, respectively, of the nucleotide sequences of SEQ ID NO: 34, wherein the first portion is 5' to the second portion in SEQ ID NO: 34. In certain embodiments, the 5' and 3' homology arms consist of a first portion and a second portion, respectively, of the nucleotide sequences of SEQ ID NO: 34, wherein the first portion is 5' to the second portion in SEQ ID NO: 34.

In certain embodiments, the first genomic region 5' to the target locus is located in a first editing window, wherein the first editing window consists of the nucleotide sequence set forth in SEQ ID NO: 34. In certain embodiments, the second genomic region 3' to the target locus is located in a second F8 targeting locus consisting of the nucleotide sequence set forth in SEQ ID NO: 34. In certain embodiments, the first genomic region 5' to the target locus is located in a first F8 targeting locus consisting of the nucleotide sequence set forth in SEQ ID NOs: 34; and the second genomic region 3' to the target locus is located in a second F8 targeting locus consisting of the nucleotide sequence set forth in SEQ ID NOs: 34.

In certain embodiments, the first genomic region 5' to the target locus comprises or consists of the sequence set forth in SEQ ID NO: 31. In certain embodiments, the second genomic region 3' to the target locus comprises or consists of the sequence set forth in SEQ ID NO: 32. In certain embodiments, the first genomic region 5' to the target locus and the second genomic region 3' to the target locus comprise or consist of the sequences set forth in SEQ ID NOs: 31 and 32, respectively.

In certain embodiments, the 5' homology arm has a length of about 50 to about 4500 nucleotides (e.g., about 100 to about 3000, about 200 to about 2500, about 300 to about 2000, about 400 to about 1500, about 500 to about 1000 nucleotides). In certain embodiments, the 5' homology arm has a length of about 800 nucleotides. In certain embodiments, the 5' homology arm has a length of about 100 nucleotides. In certain embodiments, the 3' homology arm has a length of about 50 to about 4500 nucleotides (e.g., about 100 to about 3000, about 200 to about 2500, about 300 to about 2000, about 400 to about 1500, about 500 to about 1000 nucleotides). In certain embodiments, the 3' homology arm has a length of about 800 nucleotides. In certain embodiments, the 3' homology arm has a length of about 100 nucleotides. In certain embodiments, each of the 5' and 3' homology arms independently has a length of about 50 to about 4500 nucleotides (e.g., about 100 to about 3000, about 200 to about 2500, about 300 to about 2000, about 400 to about 1500, about 500 to about 1000 nucleotides). In certain embodiments, each of the 5' and 3' homology arms has a length of about 800 nucleotides.

In certain embodiments, the 5' and 3' homology arms have substantially equal nucleotide lengths. In certain embodiments, the 5' and 3' homology arms have asymmetrical nucleotide lengths. In certain embodiments, the asymmetry in nucleotide length is defined by a difference between the 5' and 3' homology arms of up to 90% in the length, such as up to an 80%, 70%, 60%, 50%, 40%, 30%, 20%, or 10% difference in the length.

In certain embodiments, the correction genome comprises a nucleic acid sequence selected from the group consisting of SEQ ID NOs: 38-41.

In certain embodiments, the correction genomes disclosed herein further comprise a 5' inverted terminal repeat (5' ITR) nucleotide sequence 5' to the 5' homology arm nucleotide sequence, and a 3' inverted terminal repeat (3' ITR) nucleotide sequence 3' to the 3' homology arm nucleotide sequence. ITR sequences from any AAV serotype or variant thereof can be used in the correction genomes disclosed herein. The 5' and 3' ITR can be from an AAV of the same serotype or from AAVs of different serotypes. Exemplary ITRs for use in the correction genomes disclosed herein are set forth in SEQ ID NOs: 18-21, 46, 61, and 63 herein.

In certain embodiments, the 5' ITR or 3' ITR is from AAV2. In certain embodiments, both the 5' ITR and the 3' ITR are from AAV2. In certain embodiments, the 5' ITR nucleotide sequence has at least 95% (e.g., at least 96%, at least 97%, at least 98%, at least 99%, or 100%) sequence identity to SEQ ID NO: 18, or the 3' ITR nucleotide sequence has at least 95% (e.g., at least 96%, at least 97%, at least 98%, at least 99%, or 100%) sequence identity to SEQ ID NO: 19, 61, or 63. In certain embodiments, the 5' ITR nucleotide sequence has at least 95% (e.g., at least 96%, at least 97%, at least 98%, at least 99%, or 100%) sequence identity to SEQ ID NO: 18, and the 3' ITR nucleotide sequence has at least 95% (e.g., at least 96%, at least 97%, at least 98%, at least 99%, or 100%) sequence identity to SEQ ID NO: 19, 61, or 63. In certain embodiments, the correction genome comprises an editing element having the nucleic acid sequence set forth in SEQ ID NO: 34, a 5' ITR nucleotide sequence having the sequence of SEQ ID NO: 18, and a 3' ITR nucleotide sequence having the sequence of SEQ ID NO: 19, 61, or 63. In certain embodiments, the correction genome comprises the nucleic acid sequence set forth in SEQ ID NO: 34, a 5' ITR nucleotide sequence having the sequence of SEQ ID NO: 18, and a 3' ITR nucleotide sequence having the sequence of SEQ ID NO: 19, 61, or 63.

In certain embodiments, the 5' ITR or 3' ITR are from AAV5. In certain embodiments, both the 5' ITR and 3' ITR are from AAV5. In certain embodiments, the 5' ITR nucleotide sequence has at least 95% (e.g., at least 96%, at least 97%, at least 98%, at least 99%, or 100%) sequence identity to SEQ ID NO: 20, or the 3' ITR nucleotide sequence has at least 95% sequence identity to SEQ ID NO: 21. In certain embodiments, the 5' ITR nucleotide sequence has at least 95% (e.g., at least 96%, at least 97%, at least 98%, at least 99%, or 100%) sequence identity to SEQ ID NO: 20, and the 3' ITR nucleotide sequence has at least 95% (e.g., at least 96%, at least 97%, at least 98%, at least 99%, or 100%) sequence identity to SEQ ID NO: 21. In certain embodiments, the correction genome comprises an editing element having the nucleic acid sequence set forth in SEQ ID NO: 34, a 5' ITR nucleotide sequence having the sequence of SEQ ID NO: 20, and a 3' ITR nucleotide sequence having the sequence of SEQ ID NO: 21. In certain embodiments, the correction genome comprises the nucleic acid sequence set forth in SEQ ID NO: 34, a 5' ITR nucleotide sequence having the sequence of SEQ ID NO: 20, and a 3' ITR nucleotide sequence having the sequence of SEQ ID NO: 21.

In certain embodiments, the 5' ITR nucleotide sequence and the 3' ITR nucleotide sequence are substantially complementary to each other (e.g., are complementary to each other except for mismatch at 1, 2, 3, 4, or 5 nucleotide positions in the 5' or 3' ITR).

In certain embodiments, the 5' ITR or the 3' ITR is modified to reduce or abolish resolution by Rep protein ("non-resolvable ITR"). In certain embodiments, the non-resolvable ITR comprises an insertion, deletion, or substitution in the nucleotide sequence of the terminal resolution site. Such modification allows formation of a self-complementary, double-stranded DNA genome of the AAV after the transfer genome is replicated in an infected cell. Exemplary non-resolvable ITR sequences are known in the art (see e.g., those provided in U.S. Pat. Nos. 7,790,154 and 9,783,824, which are incorporated by reference herein in their entirety). In certain embodiments, the 5' ITR comprises a nucleotide sequence at least 95%, 96%, 97%, 98%, or 99% identical to SEQ ID NO: 46. In certain embodiments, the 5' ITR consists of a nucleotide sequence at least 95%, 96%, 97%, 98%, or 99% identical to SEQ ID NO: 46. In certain embodiments, the 5' ITR consists of the nucleotide sequence set forth in SEQ ID NO: 46. In certain embodiments, the 5' ITR and 3' ITR consist of the nucleotide sequences set forth in SEQ ID NOs: 46 and 19, respectively. In certain embodiments, the 5' ITR and 3' ITR consist of the nucleotide sequences set forth in SEQ ID NOs: 46 and 61, respectively.

In certain embodiments, the 5' ITR comprises a nucleotide sequence at least 95%, 96%, 97%, 98%, or 99% identical to the nucleotide sequence set forth in any one of SEQ ID NOs: 18, 20, 46. In certain embodiments, the 5' ITR consists of a nucleotide sequence at least 95%, 96%, 97%, 98%, or 99% identical to the nucleotide sequence set forth in any one of SEQ ID NOs: 18, 20, 46.

In certain embodiments, the 3' ITR comprises a nucleotide sequence at least 95%, 96%, 97%, 98%, or 99% identical to the nucleotide sequence set forth in any one of SEQ ID NOs: 19, 21, 61, 63. In certain embodiments, the 3' ITR consists of a nucleotide sequence at least 95%, 96%, 97%, 98%, or 99% identical to the nucleotide sequence set forth in any one of SEQ ID NOs: 19, 21, 61, 63.

In certain embodiments, the 3' ITR is flanked by an additional nucleotide sequence derived from a wild-type AAV2 genomic sequence. In certain embodiments, the 3' ITR is flanked by an additional 37 bp sequence derived from a wild-type AAV2 sequence that is adjacent to a wild-type AAV2 ITR. See, e.g., Savy et al., *Human Gene Therapy Methods* (2017) 28(5): 277-289 (which is hereby incorporated by reference herein in its entirety). In certain embodiments, the additional 37 bp sequence is internal to the 3' ITR. In certain embodiments, the 37 bp sequence consists of the sequence set forth in SEQ ID NO: 62 In certain embodiments, the 3' ITR comprises a nucleotide sequence at least 95%, 96%, 97%, 98%, or 99% identical to SEQ ID NO: 63. In certain embodiments, the 3' ITR comprises the nucleotide sequence set forth in SEQ ID NO: 63. In certain embodiments, the nucleotide sequence of the 3' ITR consists of a nucleotide sequence at least 95%, 96%, 97%, 98%, or 99% identical to SEQ ID NO: 63. In certain embodiments, the nucleotide sequence of the 3' ITR consists of the nucleotide sequence set forth in SEQ ID NO: 63.

In certain embodiments, the correction genome comprises a nucleic acid sequence selected from the group consisting of SEQ ID NOs: 42-45.

In certain embodiments, the correction genome consists of a nucleic acid sequence selected from the group consisting of SEQ ID NOs: 42-45.

In certain embodiments, the replication-defective AAV comprises: (a) an AAV capsid protein comprising the amino acid sequence of amino acids 203-736 of SEQ ID NO: 16, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); (b) an AAV capsid protein comprising the amino acid sequence of amino acids 138-736 of SEQ ID NO: 16, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); and/or (c) an AAV capsid protein comprising the amino acid sequence of SEQ ID NO: 16, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63).

In certain embodiments, the replication-defective AAV comprises: (a) an AAV capsid protein comprising the amino acid sequence of amino acids 203-736 of SEQ ID NO: 16, and a correction genome comprising the nucleotide sequence set forth in SEQ ID NO: 26; (b) an AAV capsid protein comprising the amino acid sequence of amino acids 138-736 of SEQ ID NO: 16, and a correction genome comprising the nucleotide sequence set forth in SEQ ID NO: 26; and/or (c) an AAV capsid protein comprising the amino acid sequence of SEQ ID NO: 16, and a correction genome comprising the nucleotide sequence set forth in SEQ ID NO: 26.

In certain embodiments, the replication-defective AAV comprises: (a) an AAV capsid protein comprising the amino acid sequence of amino acids 203-736 of SEQ ID NO: 13, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); (b) an AAV capsid protein comprising the amino acid sequence of amino acids 138-736 of SEQ ID NO: 13, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); and/or (c) an AAV capsid protein comprising the amino acid sequence of SEQ ID NO: 13, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63).

In certain embodiments, the replication-defective AAV comprises: (a) an AAV capsid protein comprising the amino acid sequence of amino acids 203-736 of SEQ ID NO: 13, and a correction genome comprising the nucleotide sequence set forth in SEQ ID NO: 26; (b) an AAV capsid protein comprising the amino acid sequence of amino acids 138-736 of SEQ ID NO: 13, and a correction genome comprising the nucleotide sequence set forth in SEQ ID NO: 26; and/or (c) an AAV capsid protein comprising the amino acid sequence of SEQ ID NO: 13, and a correction genome comprising the nucleotide sequence set forth in SEQ ID NO: 26.

The AAV compositions disclosed herein are particularly advantageous in that they are capable of correcting an F8 gene in a cell with high efficiency both in vivo and in vitro. In certain embodiments, the integration efficiency of the editing element into the target locus is at least 2% (e.g., at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is contacted in vitro in the absence of an exogenous nuclease with a population of B lymphoblastoid cells under standard AAV transduction conditions for B lymphoblastoid cells. In certain embodiments, the allelic frequency of integration of the editing element into the target locus is at least 1% (e.g., at least 1%, 1.5%, 2%, 2.5%, 3%, 3.5%, 4%, 4.5%, 5%, 7.5%, 10%, 15%, 20%, 25%, 30%, 35%, 40%, 45%, 50%, 55%, 60%, 65%, 70%, 75%, 80%, 85%, 90%, or 95%) when the AAV is contacted in vitro in the absence of a exogenous nuclease with a population of B lymphoblastoid cells under standard AAV transduction conditions for B lymphoblastoid cells. In certain embodiments, the integration efficiency of the editing element into the target locus in the liver is at least 2% (e.g., at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is administered to a subject in the absence of an exogenous nuclease or a nuclease sequence that encodes an exogenous nuclease under standard AAV administration conditions. In certain embodiments, the allelic frequency of integration of the editing element into the target locus in the liver is at least 1% (e.g., at least 1%, 1.5%, 2%, 2.5%, 3%, 3.5%, 4%, 4.5%, 5%, 7.5%, 10%, 15%, 20%, 25%, 30%, 35%, 40%, 45%, 50%, 55%, 60%, 65%, 70%, 75%, 80%, 85%, 90%, or 95%) when the AAV is administered to a subject in the absence of a exogenous nuclease or a nuclease sequence that encodes an exogenous nuclease under standard AAV administration conditions. As used herein, the term "standard AAV administration conditions" refers to administration of an AAV intravenously at a dose of $1.5\times10^5$ vector genomes per kilogram of body weight for a subject having the size and body shape of a mouse. A skilled worker will appreciate that the dose should be adjusted according to the size and body shape of the subject to achieve similar predicted efficacy. An exemplary dose conversion between species is provided by Nair et al. (2016) J. Basic Clin. Pharm. 7(2): 27-31, which is incorporated by reference herein in its entirety.

Any methods of determining the efficiency of editing of the F8 gene can be employed. In certain embodiments, individual cells are separated from the population of transduced cells and subject to single-cell PCR using PCR primers that can identify the presence of an editing element correctly integrated into the target locus of the F8 gene. Such method can further comprise single-cell PCR of the same cells using PCR primers that selectively amplify an unmodified target locus. In this way, the genotype of the cells can be determined. For example, if the single-cell PCR showed that a cell has both an edited target locus and an unmodified target locus, then the cell would be considered heterozygous for the edited F8 gene.

Additionally or alternatively, in certain embodiments, linear amplification mediated PCR (LAM-PCR), quantitative PCR (qPCR), or digital droplet PCR (ddPCR) can be performed on DNA extracted from the population of transduced cells using primers and probes that only detect edited F8 alleles. Such method can further comprise an additional qPCR or ddPCR (either in the same reaction or a separate reaction) to determine the number of total genomes in the sample and the number of unedited F8 alleles. These numbers can be used to determine the allelic frequency of integration of the editing element into the target locus.

Additionally or alternatively, in certain embodiments, the F8 locus can be amplified from DNA extracted from the population of transduced cells either by PCR using primers that bind to regions of the F8 gene flanking the genomic region encompassed by the correction genome, or by linear amplification mediated PCR (LAM-PCR) using a primer that binds a region within the correction genome (e.g., a region comprising an exogenous sequence non-native to the locus. The resultant PCR amplicons can be individually sequenced using single molecule next generation sequencing (NGS) techniques to determine the relative number of edited and unedited F8 alleles present in the population of transduced cells. These numbers can be used to determine the allelic frequency of integration of the editing element into the target locus.

In another aspect, the instant disclosure provides pharmaceutical compositions comprising an AAV as disclosed herein together with a pharmaceutically acceptable excipient, adjuvant, diluent, vehicle or carrier, or a combination thereof. A "pharmaceutically acceptable carrier" includes any material which, when combined with an active ingredient of a composition, allows the ingredient to retain biological activity and without causing disruptive physiological reactions, such as an unintended immune reaction. Pharmaceutically acceptable carriers include water, phosphate buffered saline, emulsions such as oil/water emulsion, and wetting agents. Compositions comprising such carriers are formulated by well-known conventional methods such as those set forth in Remington's Pharmaceutical Sciences, current ed., Mack Publishing Co., Easton Pa. 18042, USA; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., 7th ed., Lippincott, Williams, & Wilkins; and Handbook of Pharmaceutical Excipients (2000) A. H. Kibbe et al., 3rd ed. Amer. Pharmaceutical Assoc.

III. Methods of Use

In another aspect, the instant disclosure provides methods for correcting a mutation in the F8 gene or expressing a FVIII polypeptide in a cell. The methods generally comprise transducing the cell with a replication-defective AAV as disclosed herein. Such methods are highly efficient at correcting mutations in the F8 gene or restoring F8 expression, and do not require cleavage of the genome at the target locus by the action of an exogenous nuclease (e.g., a meganuclease, a zinc finger nuclease, a transcriptional activator-like nuclease (TALEN), or an RNA-guided nuclease such as a Cas9) to facilitate such correction. Accordingly, in certain embodiments, the methods disclosed herein involve transducing the cell with a replication-defective AAV as disclosed herein without co-transducing or co-administering an exogenous nuclease or a nucleotide sequence that encodes an exogenous nuclease.

The methods disclosed herein can be applied to any cell harboring a mutation in any or all of exons 23-26 or any or all of introns 22-25 of the F8 gene. The skilled worker will appreciate that cells that are active in F8 expression are of particular interest. Accordingly, in certain embodiments, the method is applied to hepatocytes, liver sinusoidal endothelial cells and/or other endothelial cells. In certain embodiments, the method is applied to a liver. The cells or liver can be in a subject (e.g., a human subject).

The methods disclosed herein can be performed in vitro for research purposes or can be performed ex vivo or in vivo for therapeutic purposes.

In certain embodiments, the cell to be transduced is in a mammalian subject and the AAV is administered to the subject in an amount effective to transduce the cell in the subject. Accordingly, in certain embodiments, the instant disclosure provides a method for treating a subject having a disease or disorder associated with an F8 gene mutation, the method generally comprising administering to the subject an effective amount of a replication-defective AAV as disclosed herein. The subject can be a human subject or a rodent subject (e.g., a mouse) containing human liver cells. Suitable mouse subjects include without limitation, mice into which human liver cells (e.g., human hepatocytes and human hepatic sinusoidal endothelial cell) have been engrafted. Hemophilia A or any other disorder associated with an F8 gene mutation in any or all of exons 23-26 or any or all of introns 22-25 can be treated using the methods disclosed herein. In certain embodiments, the cell is transduced without co-transducing or co-administering an exogenous nuclease or a nucleotide sequence that encodes an exogenous nuclease.

In certain embodiments, the foregoing methods emply a replication-defective AAV comprises: (a) an AAV capsid protein comprising the amino acid sequence of amino acids 203-736 of SEQ ID NO: 16, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); (b) an AAV capsid protein comprising the amino acid sequence of amino acids 138-736 of SEQ ID NO: 16, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); and/or (c) an AAV capsid protein comprising the amino acid sequence of SEQ ID NO: 16, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63).

In certain embodiments, the foregoing methods employ a replication-defective AAV comprises: (a) an AAV capsid protein comprising the amino acid sequence of amino acids 203-736 of SEQ ID NO: 16, and a correction genome comprising the nucleotide sequence set forth in SEQ ID NO: 26; (b) an AAV capsid protein comprising the amino acid sequence of amino acids 138-736 of SEQ ID NO: 16, and a correction genome comprising the nucleotide sequence set forth in SEQ ID NO: 26; and/or (c) an AAV capsid protein comprising the amino acid sequence of SEQ ID NO: 16, and a correction genome comprising the nucleotide sequence set forth in SEQ ID NO: 26.

In certain embodiments, the foregoing methods employ a replication-defective AAV comprises: (a) an AAV capsid protein comprising the amino acid sequence of amino acids 203-736 of SEQ ID NO: 13, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); (b) an AAV capsid protein comprising the amino acid sequence of amino acids 138-736 of SEQ ID NO: 13, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); and/or (c) an AAV capsid protein comprising the amino acid sequence of SEQ ID NO: 13, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63).

In certain embodiments, the foregoing methods employ a replication-defective AAV comprises: (a) an AAV capsid protein comprising the amino acid sequence of amino acids 203-736 of SEQ ID NO: 13, and a correction genome comprising the nucleotide sequence set forth in SEQ ID NO: 26; (b) an AAV capsid protein comprising the amino acid sequence of amino acids 138-736 of SEQ ID NO: 13, and a correction genome comprising the nucleotide sequence set forth in SEQ ID NO: 26; and/or (c) an AAV capsid protein comprising the amino acid sequence of SEQ ID NO: 13, and a correction genome comprising the nucleotide sequence set forth in SEQ ID NO: 26.

The methods disclosed herein are particularly advantageous in that they are capable of correcting an F8 gene in a cell with high efficiency both in vivo and in vitro. In certain embodiments, the integration efficiency of the editing element into the target locus is at least 2% (e.g. at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is contacted in vitro in the absence of an exogenous nuclease with a population of B lymphoblastoid cells under standard AAV transduction conditions for B lymphoblastoid cells. In certain embodiments, the allelic frequency of integration of the editing element into the target locus is at least 1% (e.g. at least 1%, 1.5%, 2%, 2.5%, 3%, 3.5%, 4%, 4.5%, 5%, 7.5%, 10%, 15%, 20%, 25%, 30%, 35%, 40%, 45%, 50%, 55%, 60%, 65%, 70%, 75%, 80%, 85%, 90%, or 95%) when the AAV is contacted in vitro in the absence of a exogenous nuclease with a population of B lymphoblastoid cells under standard AAV transduction conditions for B lymphoblastoid cells. In certain embodiments, the integration efficiency of the editing element into the target locus in the liver is at least 2% (e.g., at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is administered to a subject in the absence of an exogenous nuclease or a nuclease sequence that encodes an exogenous nuclease under standard AAV administration conditions. In certain embodiments, the allelic frequency of integration of the editing element into the target locus in the liver is at least 1% (e.g., at least 1%, 1.5%, 2%, 2.5%, 3%, 3.5%, 4%, 4.5%, 5%, 7.5%, 10%, 15%, 20%, 25%, 30%, 35%, 40%, 45%, 50%, 55%, 60%, 65%, 70%, 75%, 80%, 85%, 90%, or 95%) when the AAV is administered to a subject in the absence of a exogenous nuclease or a nuclease sequence that encodes an exogenous nuclease under standard AAV administration conditions. As used herein, the term "standard AAV administration conditions" refers to administration of an AAV intravenously at a dose of $1.5\times10^5$ vector genomes per kilogram of body weight for a subject having the size and body shape of a mouse. A skilled worker will appreciate that the dose should be adjusted according to the size and body shape of the subject to achieve similar predicted efficacy. An exemplary dose conversion between species is provided by Nair et al. (2016) J. Basic Clin. Pharm. 7(2): 27-31, which is incorporated by reference herein in its entirety. Any methods of determining the efficiency of editing of the F8 gene can be employed including, without limitation, those described herein.

The methods disclosed herein are also advantageous in that they are capable of expressing a FVIII protein in a cell with high efficiency both in vivo and in vitro. In certain embodiments, the expression level of the FVIII protein is at least 10%, 20%, 30%, 40%, 50%, 60%, 70%, 80%, 90%, or 100% of the expression level of the endogenous FVIII protein in a cell of the same type that does not have a mutation in the F8 gene. In certain embodiments, the expression level of the FVIII protein is at least 1.1, 1.2, 1.3, 1.4, 1.5, 1.6, 1.7, 1.8, 1.9, 2, 3, 4, 5, 6, 7, 8, 9, or 10 fold higher than the expression level of the endogenous FVIII protein in a cell of the same type that does not have a mutation in the F8 gene. Any methods of determining the expression level of the FVIII protein can be employed including, without limitation, ELISA, Western blotting, immunostaining, and mass spectrometry.

In certain embodiments, transduction of a cell with an AAV composition disclosed herein can be performed as provided herein or by any method of transduction known to one of ordinary skill in the art. In certain embodiments, the cell may be contacted with the AAV at a multiplicity of infection (MOI) of 50,000; 100,000; 150,000; 200,000; 250,000; 300,000; 350,000; 400,000; 450,000; or 500,000, or at any MOI that provides for optimal transduction of the cell.

An AAV composition disclosed herein can be administered to a subject by any appropriate route including, without limitation, intravenous, intraperitoneal, subcutaneous, intramuscular, intranasal, topical or intradermal routes. In certain embodiments, the composition is formulated for administration via intravenous injection or subcutaneous injection.

IV. AAV Packaging Systems

In another aspect, the instant disclosure provides packaging systems for recombinant preparation of a replication-defective AAV disclosed herein. Such packaging systems generally comprise: a Rep nucleotide sequence encoding one or more AAV Rep proteins; a Cap nucleotide sequence encoding one or more AAV Clade F capsid proteins as disclosed herein; and a correction genome for correction of the F8 gene as disclosed herein, wherein the packaging system is operative in a cell for enclosing the correction genome in the capsid to form the AAV.

In certain embodiments, the packaging system comprises a first vector comprising the Rep nucleotide sequence and the Cap nucleotide sequence, and a second vector comprising the correction genome. As used in the context of a packaging system as described herein, a "vector" refers to a nucleic acid molecule that is a vehicle for introducing nucleic acids into a cell (e.g., a plasmid, a virus, a cosmid, an artificial chromosome, etc.).

Any AAV Rep protein can be employed in the packaging systems disclosed herein. In certain embodiments of the packaging system, the Rep nucleotide sequence encodes an AAV2 Rep protein. Suitable AAV2 Rep proteins include, without limitation, Rep 78/68 or Rep 68/52. In certain embodiments of the packaging system, the AAV2 Rep protein comprises an amino acid sequence having a minimum percent sequence identity to the AAV2 Rep amino acid sequence of SEQ ID NO: 22, wherein the minimum percent sequence identity is at least 70% (e.g., at least 75%, at least 80%, at least 85%, at least 90%, at least 95%, at least 98%, at least 99%, or 100%) across the length of the amino acid sequence of the AAV2 Rep protein. In certain embodiments of the packaging system, the AAV2 Rep protein has the amino acid sequence set forth in SEQ ID NO: 22.

In certain embodiments of the packaging system, the packaging system further comprises a third vector, e.g., a helper virus vector. The third vector may be an independent third vector, integral with the first vector, or integral with the second vector. In certain embodiments, the third vector comprises genes encoding helper virus proteins.

In certain embodiments of the packaging system, the helper virus is selected from the group consisting of adenovirus, herpes virus (including herpes simplex virus (HSV)), poxvirus (such as vaccinia virus), cytomegalovirus (CMV), and baculovirus. In certain embodiments of the packaging system, where the helper virus is adenovirus, the adenovirus genome comprises one or more adenovirus RNA genes selected from the group consisting of E1, E2, E4 and VA. In certain embodiments of the packaging system, where the helper virus is HSV, the HSV genome comprises one or more of HSV genes selected from the group consisting of UL5/8/52, ICPO, ICP4, ICP22 and UL30/UL42.

In certain embodiments of the packaging system, the first, second, and/or third vector are contained within one or more transfecting plasmids. In certain embodiments, the first vector and the third vector are contained within a first transfecting plasmid. In certain embodiments the second vector and the third vector are contained within a second transfecting plasmid.

In certain embodiments of the packaging system, the first, second, and/or third vector are contained within one or more recombinant helper viruses. In certain embodiments, the first vector and the third vector are contained within a recombinant helper virus. In certain embodiments, the second vector and the third vector are contained within a recombinant helper virus.

In a further aspect, the disclosure provides a method for recombinant preparation of an AAV as described herein, wherein the method comprises transfecting or transducing a cell with a packaging system as described under conditions operative for enclosing the correction genome in the capsid to form the AAV as described herein. Exemplary methods for recombinant preparation of an AAV include transient transfection (e.g., with one or more transfection plasmids containing a first, and a second, and optionally a third vector as described herein), viral infection (e.g. with one or more recombinant helper viruses, such as a adenovirus, poxvirus (such as vaccinia virus), herpes virus (including HSV, cytomegalovirus, or baculovirus, containing a first, and a second, and optionally a third vector as described herein), and stable producer cell line transfection or infection (e.g., with a stable producer cell, such as a mammalian or insect cell, containing a Rep nucleotide sequence encoding one or more AAV Rep proteins and/or a Cap nucleotide sequence encoding one or more AAV Clade F capsid proteins as described herein, and with a correction genome as described herein being delivered in the form of a transfecting plasmid or a recombinant helper virus).

V. Examples

The recombinant AAV vectors disclosed herein mediate highly efficient gene editing or gene transfer in vitro and in vivo. The following examples demonstrate the efficient restoration of the expression of the F8 gene which is mutated in certain human diseases, such as hemophilia A, using an AAV-based vector as disclosed herein. These examples are offered by way of illustration, and not by way of limitation.

Example 1: Editing of the Human F8 Gene Locus Using AAV Vectors

This example provides F8 correction vectors VG-F8-002-FP and VG-F8-003-FP, each containing an editing element for insertion of a reporter (a fluorescent protein (FP)) coding sequence after exon 22 or into intron 22, respectively, of the human F8 gene.

VG-F8-002-FP

The VG-F8-002-FP vector, as shown in FIG. 1A, encompasses 5' to 3': a 5' ITR; a 5' homology arm consisting of the sequence of nucleotides 125,677-126,476 of human F8 gene; a T2A element; a FP coding sequence; a nuclear localization signal (NLS) encoding sequence; an SV40 polyadenylation sequence; a 3' homology arm consisting of the sequence of nucleotides 126,477-127,276 of human F8 gene; and a 3' ITR.

Integration of the F8 specific correction vector VG-F8-002-FP into the human genome inserts the T2A element, the FP coding sequence, the NLS, and the SV40 polyadenylation sequence after the last codon of the exon 22 of the human F8 gene. The T2A peptide leads to generation of two polypeptides: a truncated F8 peptide terminated at the end of exon 22 fused with an N-terminal part of the T2A peptide, and a full-length FP polypeptide with a proline from the T2A peptide remaining at the N-terminus. Integration of this vector thereby directs the expression of the fluorescent protein under the control of the F8 promoter which is present in the human genome but not provided in the VG-F8-002-FP vector.

VG-F8-003-FP

Figure 1B:
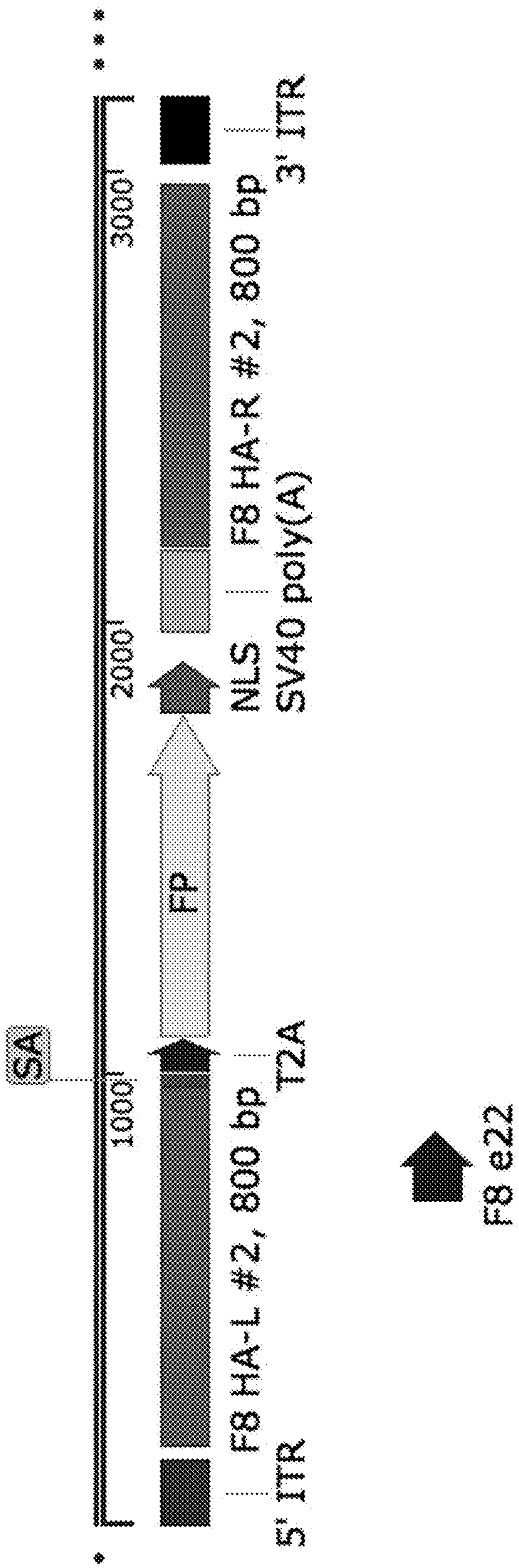

The VG-F8-003-FP vector, as shown in FIG. 1B, encompasses 5' to 3': a 5' ITR; a 5' homology arm consisting of the sequence of nucleotides 125,777-126,576 of human F8 gene; a splice acceptor element; a T2A element; coding sequence for FP; an NLS encoding sequence; an SV40 polyadenylation sequence; a 3' homology arm consisting of the sequence of nucleotides 126,577-127,376 of human F8 gene, and a 3' ITR.

Integration of the F8 specific correction vector VG-F8-003-FP into the human genome inserts the splice acceptor, T2A element, the FP coding sequence, the NLS encoding sequence, and the SV40 polyadenylation sequence after nucleotide 126,576 of the human F8 gene in intron 22. The mRNA transcribed from the edited F8 locus comprises exons 1-22 of the human F8 gene, the T2A element, the FP coding sequence, and the NLS encoding sequence. The 2A peptide leads to generation of two polypeptides: a truncated FVIII peptide terminated at the end of exon 22 fused with an N-terminal part of the 2A peptide, and a full-length FP polypeptide with a proline from the 2A peptide remaining at the N-terminus. Integration of this vector thereby directs the expression of the fluorescent protein under the control of the F8 promoter which is present in the human genome but not provided in the VG-F8-003-FP vector.

VG-F8-002-FP and VG-F8-003-FP were examined in vitro for assessment of targeted integration. B lymphoblastoid cell lines 16756, 14623, and 13023 were cultured in RPMI supplemented with 15% fetal calf serum (FCS) and 2 mM L-glutamine. Cells were seeded at approximately 200, 000 cells per mL and split when cells reached between 500,000 to 1,000,000 cells per mL.

Vectors were packaged with AAVHSC17, and the viral particles were tested for their ability to edit the human F8 gene in B lymphoblastoid cells. AAVHSC-AAVS1-FP, an AAV vector comprising AAV2 ITRs, homology arms for genome integration into the AAVS1 locus, and a promoter-less fluorescent protein, serves as a control for gene integration (see e.g., WO 2016/049230 A1, which is incorporated by reference herein in its entirety).

Cells were in log phase growth on the day of transduction. Cells were counted and an appropriate number of cells were plated. Typically, 10,000 cells were plated for flow cytometry analysis. Vector did not exceed 10% of the culture volume. Vector was calculated based on the titer and MOI and was calculated before plating to ensure proper plates were used.

Vectors were thawed on ice and sonicated on ice if necessary prior to transductions. Virus was added to each well individually and media was pipetted up and down to evenly distribute virus. 48 hours after transduction, cells transduced with AAVF F8 FP vectors were harvested using FACS Buffer (1×PBS, 2% FCS, 0.1% sodium azide). Cells were spun down at 1200 RPM for 10 minutes. FACS buffer was removed so that approximately 200 μL remained. DAPI (100 μM working stock) was added immediately before flow cytometry analysis to a final concentration of 3 μM.

Figure 2:
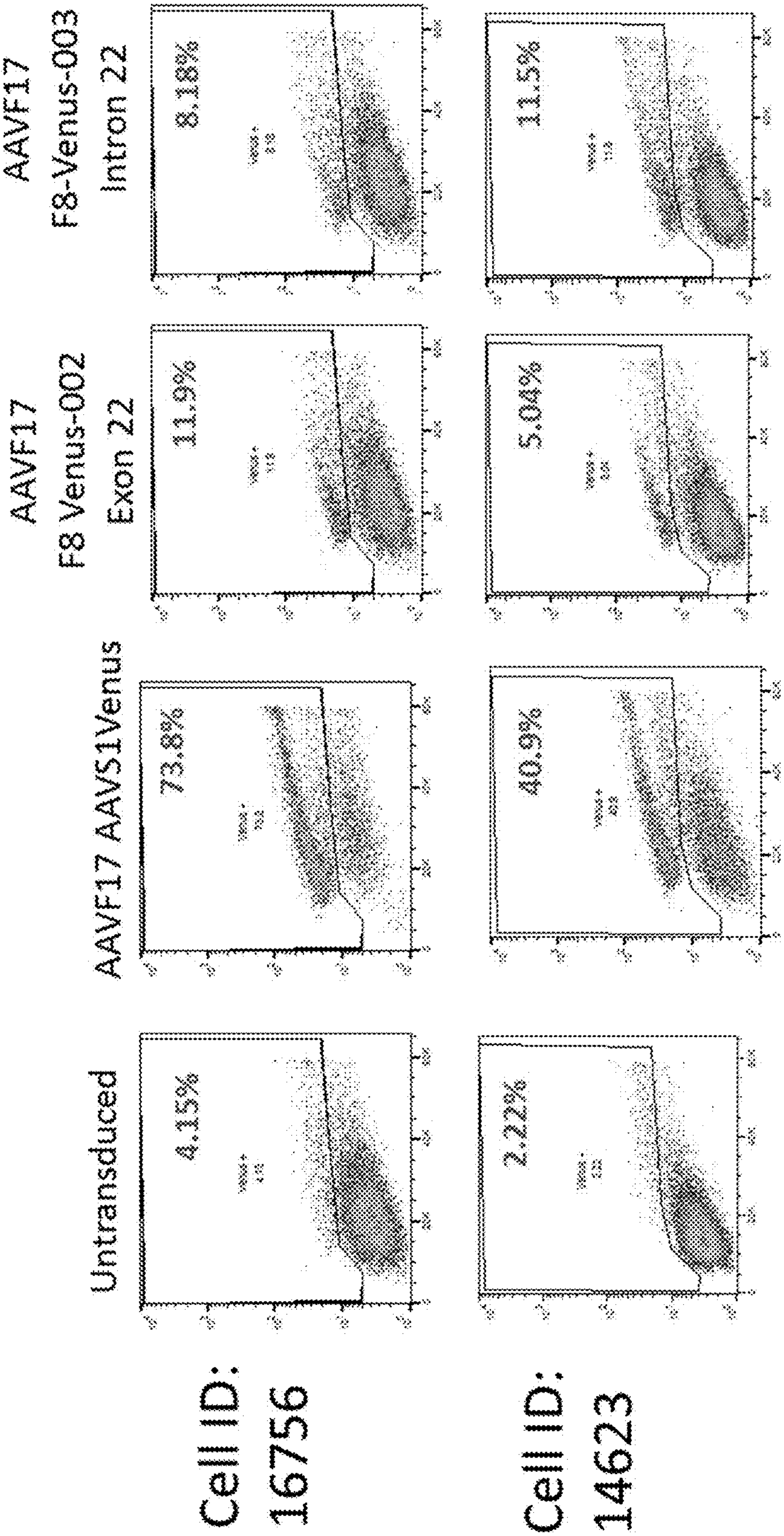
FIG. 2 is a series of graphs depicting editing of the human F8 locus as measured by flow cytometry with three B lymphoblastoid transduced with reporter vectors.
Figure 2:
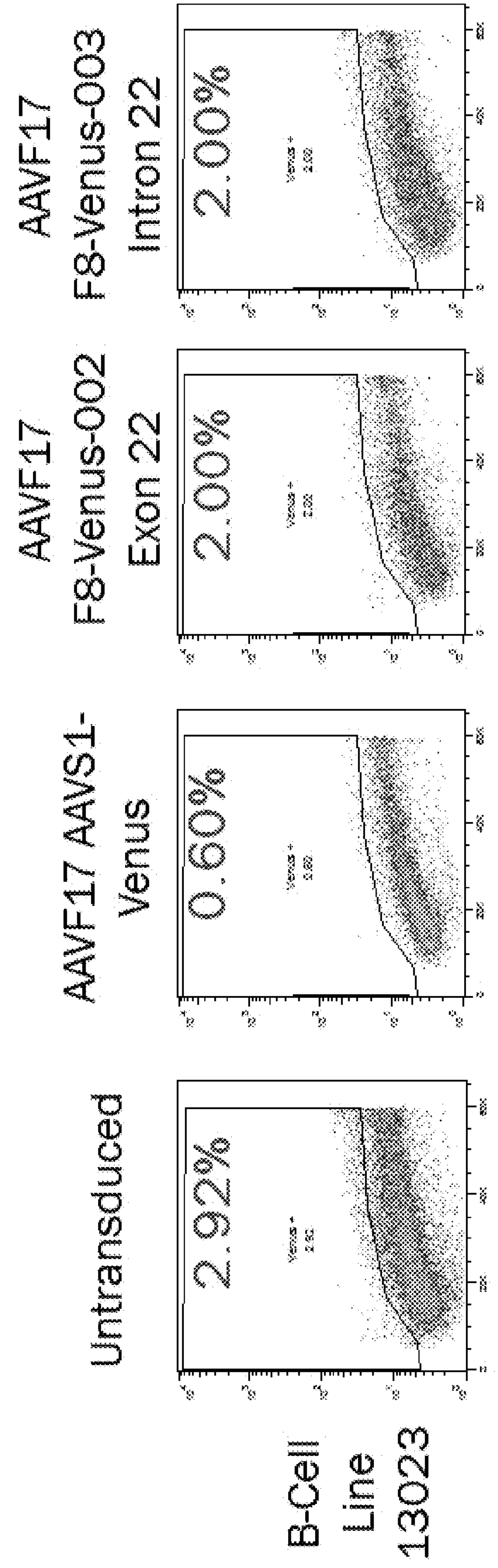

The rate of gene editing was calculated by subtracting the percentage of FP-positive cells in an untransduced sample from the percentage of FP-positive cells in the corresponding transduced sample. As shown in FIG. 2, about 3-8% of FANCD2 heterozygous B lymphoblastoid cells (Cell ID: 16756) were edited by the VG-F8-002-FP vector packaged in AAVHSC17 capsid in the human F8 locus, and about 4-9% of and FANCD1 heterozygous B lymphoblastoid cells (Cell ID: 14623) were edited by the VG-F8-003-FP packaged in AAVHSC17 capsid in the human F8 locus. In contrast, the rate of gene editing in FANCD1 (an essential mediator of homologous recombination also named BRCA2)-deficient B lymphoblastoid cells (Cell ID: 13023) was not detectable. In sum, these data show editing of the F8 gene locus using AAV vectors, and further, that the observed editing is mediated by homologous recombination.

Example 2: Human Tissues Capable of Expressing F8

Figure 3:
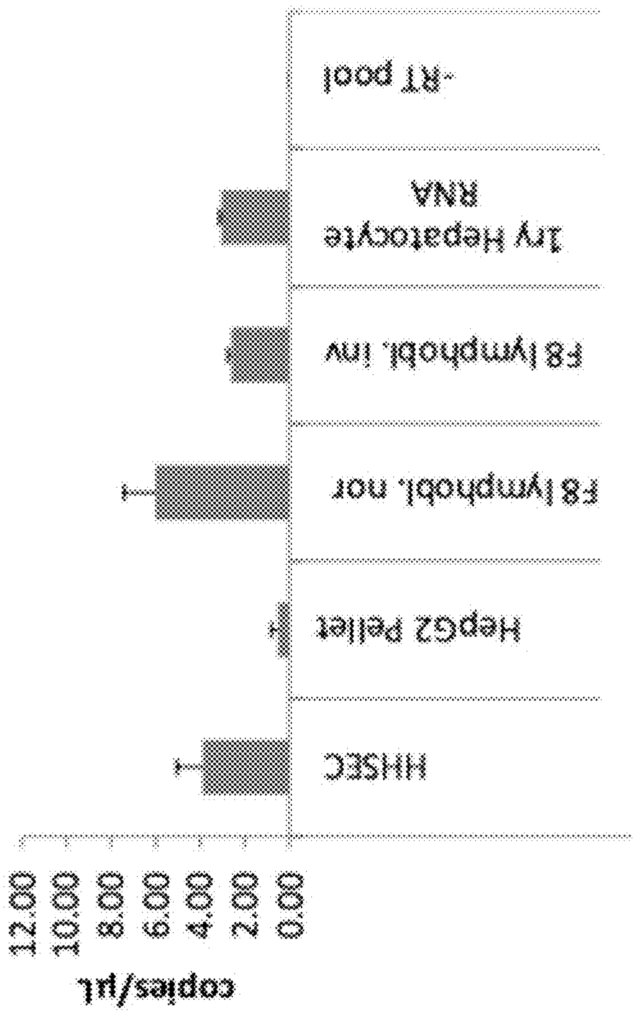
FIG. 3 is a graph showing the mRNA expression of F8 in mammalian cells.

The expression of F8 may be restored in one or more cell types that are capable of expressing F8. FIG. 3 shows the levels of F8 mRNA in primary human hepatic sinusoidal endothelial cells ("HHSEC"), human hepatoma HepG2 cells ("HepG2"), B lymphoblasts from a normal individual ("F8 lymphobl.nor"), B lymphoblasts from a patient harboring the F8 intron 22 inversion ("F8 lymphobl.inv"), and primary human hepatocytes ("1ry Hepatocyte RNA"). These levels were measured by digit droplet PCR (ddPCR) following the protocol described below.

Frozen cell pellets were used for RNA isolation. Cells were thawed and washed with PBS to remove the DMSO. Total RNA was isolated from cell pellets using the RNeasy mini kit (Qiagen), and concentration was measured with SimpliNano (GE healthcare). 900 ng of RNA per cell type was used for a RT reaction to create cDNA, with the exception of the B lymphoblasts from a patient harboring the F8 intron 22 inversion, wherein 450 ng of RNA was used for the RT reaction. This was corrected in the final data analysis.

TaqMan® Reverse Transcription Reagents (Applied Bioscience, Cat. N8080234) were used for generating cDNA. The TaqMan® primers and probes used are shown in Table 1 below. Complementary DNA samples were diluted 1:3 in distilled water and a mixture was made of 10 μl Master mix, 1 μl of FAM probe (F8), 1 μl of VIC probe (GAPDH) and 8 μl of diluted cDNA. Droplets were generated using the DG8 cartridge, according to the QX200 Droplet generator Manual (Bio-Rad #10031907). The cycle parameters for the ddPCR are described in Table 2. After the PCR, the droplets were read on the QX200 droplet reader and analyzed using the Quantasoft Software.

TABLE 1

TaqMan ® primers and probes used for quantifying F8 mRNA

| Assay ID | Assay name | Cat # | Lot# |
|---|---|---|---|
| Hs00252034_m1 | F8 | 4331182 | 1276586 |
| Hs00240767_m1 | F8 | 4331182 | 1418037 |
| Hs02758991_g1 | GAPDH | 4448490 | P150630-001 H10 |

TABLE 2

Cycle parameters for ddPCR

| Cycling step | Temp, ° C. | Time | ramp rate | # of cycles |
|---|---|---|---|---|
| Enzyme activation | 95 | 10 min | 2 C./sec | 1 |
| Denaturation | 94 | 30 sec | | 40 |
| Annealing/extension | 60 | 1 min | | 40 |
| Enzyme deactivation | 98 | 10 min | | 1 |
| Hold(optional) | 12 | infinite | | 1 |

Example 3: In Vivo Editing of the Murine F8 Gene Locus Using AAV Vectors

Figure 4A:
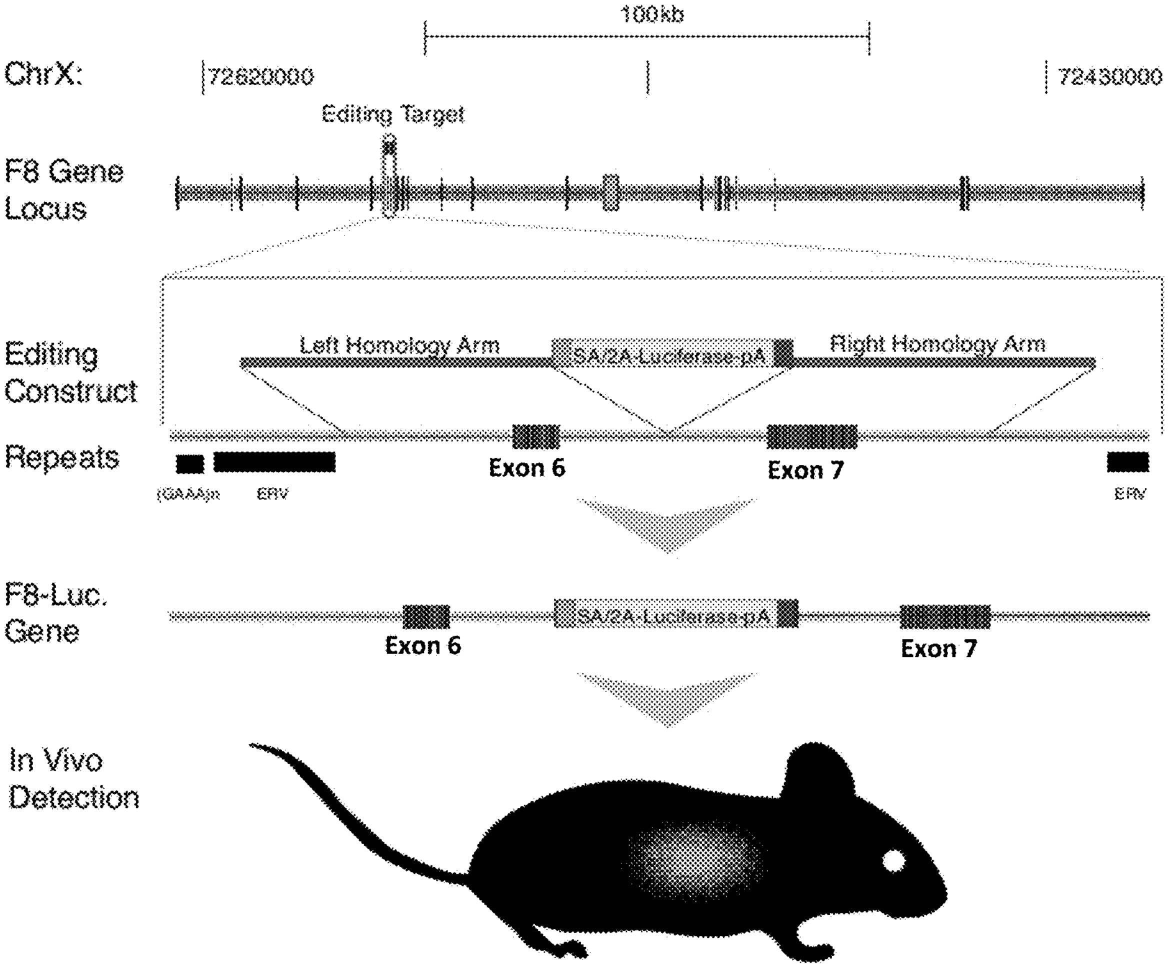
FIG. 4A is a map of the VG-mF8-001-Luc vector and its expected integration into a mouse genome.

This example provides in vivo editing of the F8 locus after administration of VG-mF8-001-Luc vector. A map of the VG-mF8-001-Luc vector is shown in FIG. 4A. This vector comprises 5' to 3' a 5' ITR (not shown), a left homology arm having homology to a first sequence from intron 5 to intron 6 of mouse F8 ("HAL," having the sequence of nucleotides 48,303-49,102 of mouse F8), a splice acceptor ("SA"), a T2A element ("2A"), a promoter-less nucleotide sequence encoding luciferase ("Luc ORF"), an SV40 polyadenylation sequence ("pA"), a right homology arm having homology to a second sequence from intron 6 to intron 7 of mouse F8 ("HAR," having the sequence of nucleotides 49,103-49,902 of mouse F8), and a 3' ITR (not shown).

Integration of the VG-mF8-001-Luc vector into the mouse genome inserts the splice acceptor, T2A element, the luciferase coding sequence, and the SV40 polyadenylation sequence in intron 6 of the mouse F8 gene. The mRNA transcribed from the edited F8 locus comprises exons 1-6 of the mouse F8 gene, the T2A element, and the luciferase coding sequence. The T2A peptide leads to generation of two polypeptides: a truncated FVIII peptide terminated at the end of exon 6 fused with an N-terminal part of the T2A peptide, and a full-length luciferase polypeptide with a proline from the 2A peptide remaining at the N-terminus. Integration of this vector thereby directs the expression of the luciferase protein under the control of the F8 promoter which is present in the mouse genome but not provided in the VG-mF8-001-Luc vector.

Figure 4B:
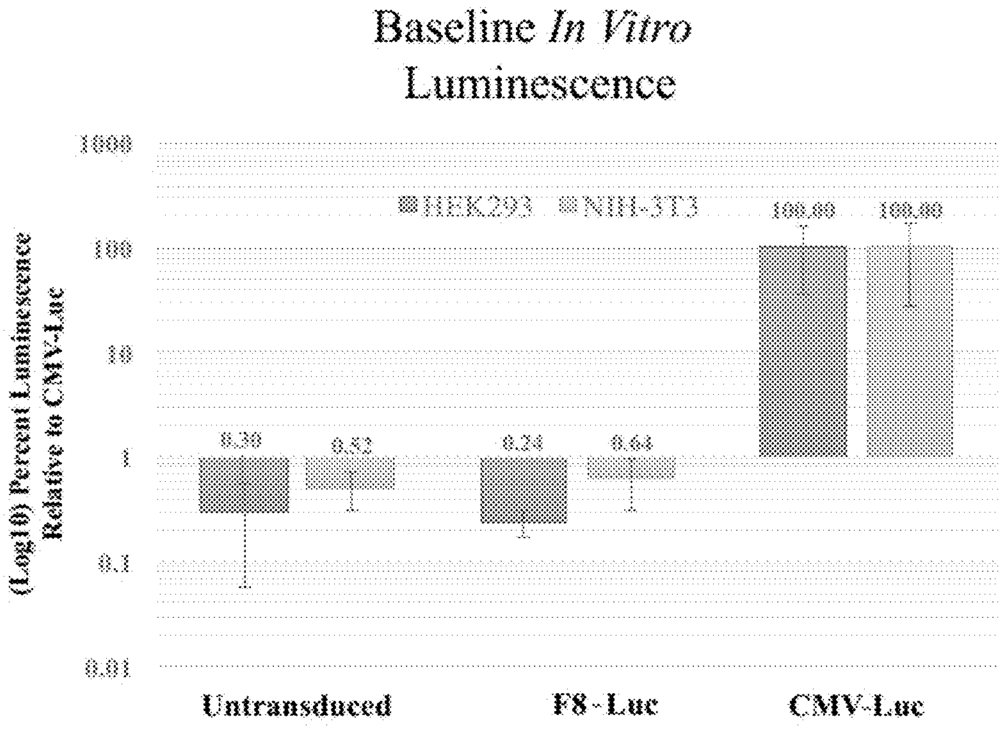
FIG. 4B is a graph showing bioluminescence from HEK293 and NIH3T3 cells transfected with the VG-mF8-001-Luc vector.

The homology arm sequences did not include predicted hallmarks of transcriptional regulatory elements that might act to drive episomal luciferase expression (see transcriptional regulatory elements predicted in Sabo et al. (2006) *Nat Methods* 3: 511-18; Griffith et al. (2008) *Nucleic Acids Res* 36: D107-13; and Rando et al. (2009) *Annu Rev Biochem* 78: 245-71). To ensure that a luciferase protein did not express from the editing vector without genome integration, the VG-mF8-001-Luc vector was transfected into human HEK293 and mouse NIH3T3 cells. As shown in FIG. 4B, no bioluminescence was detected from the transfected cells 24 hours after transfection. By contrast, bioluminescence was detected from the cells transfected with a positive control vector comprising a luciferase encoding sequence driven by a CMV promoter. While not wishing to be bound by theory, it is hypothesized that the vector did not substantially integrate into the genome of NIH3T3 cells because the rate of homologous recombination was low by transfection, i.e., in the absence of the AAVHSC delivery apparatus.

Figure 4C:
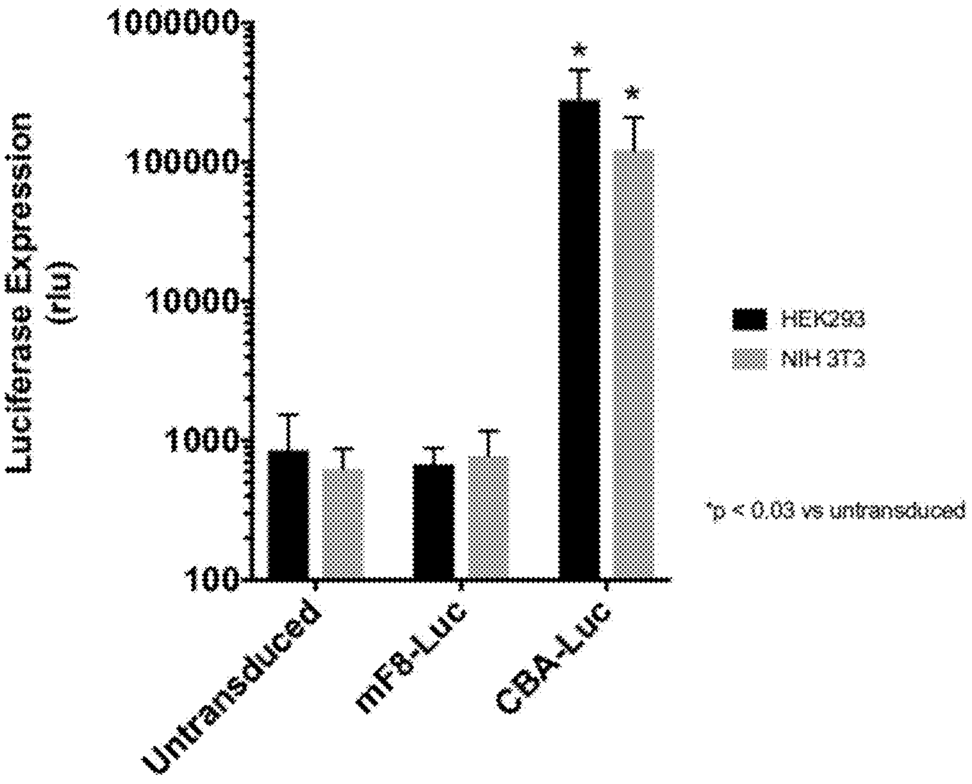
FIG. 4C is a graph showing luciferase expression in relative luminometer units (RLU) from HEK293 and NIH3T3 cells transfected with the VG-mF8-001-Luc vector.

FIG. 4C is a graph showing luciferase expression in relative luminometer units (RLU) from HEK293 and NIH3T3 cells transfected with the VG-mF8-001-Luc vector. As shown in FIG. 4C, luciferase expression was measured to be the same between HEK293 and NIH3T3 cells transfected with the VG-mF8-001-Luc vector, and HEK293 and NIH3T3 cells that were untransduced. In contrast, luciferase expression was detected from cells transfected with a positive control vector comprising a luciferase encoding sequence driven by a chicken β-actin (CBA) promoter.

The VG-mF8-001-Luc vector was packaged in AAVHSC15 or AAVHSC17 (see WO 2016/049230 A1, which is incorporated by reference herein in its entirety). A control vector named VG-ASA-mF8-001-Luc, which was different from VG-mF8-001-Luc in the absence of the splice acceptor, was also packaged in AAVHSC15. To ensure consistent AAV virus quality, each vector was analyzed across a panel of characteristics; DNA and capsid titer, vector protein purity by silver stain, capsid protein western-blot and endotoxin burden. There were no significant differences in vector purity, quality or titer between each vector preparation. Female C57BL/6 mice 6-8-week old obtained from Charles River Laboratories received either a low dose of $1\times10^{10}$ vector genomes (approximately $5\times10^{11}$ vector genomes per kilogram of body weight) or a high dose of $3\times10^{12}$ vector genomes (approximately $1.5\times10^{14}$ vector genomes per kilogram of body weight) that was injected intravenously via tail vein at a maximum of 10 ml/kg to each mouse. Serial bioluminescent imaging was performed on anesthetized mice that were injected intraperitoneally with 0.15 mg/g of luciferin (Caliper Life Sciences). Images were taken 10 minutes after luciferin injection using a SPECTRAL LagoX imaging system (Spectral Instruments Imaging, LLC). Mice were imaged for 5 minutes with large binning ventrally. Organs were then harvested and imaged. Images were analyzed using AMIView software version 1.7.06.

To detect editing of the F8 gene, liver samples were collected from mice after administration of the AAV vectors, total DNA was isolated from the samples using the QIAamp DNA mini kit (Qiagen), and DNA concentrations were measured with NanoDrop (ThermoFisher). The DNA samples was analyzed by the following methods:

End-Point PCR

Figure 5A:
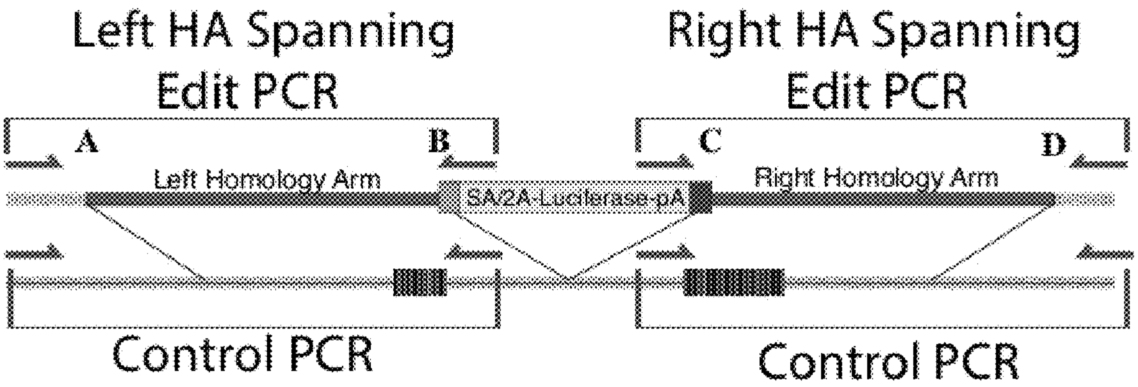
FIG. 5A illustrates two PCR designs for detecting homologous recombination of the VG-mF8-001-Luc vector into the mouse genome.

Liver genomic DNA was analyzed by end-point PCR using primers specific for integration of the luciferase cassette into the target site. The primer sequences are provided in Table 3 below, and their targeting regions are shown in FIG. 5A. The PCR conditions are provided in Table 4. As genomic PCR controls, comparably sized PCRs were run spanning each homology arm. The specificity of each amplicon was confirmed by Sanger sequencing.

TABLE 3

Primers for quantifying F8 edited DNA by end-point PCR

| Assay name | Primer name | Target region | Sequences | SEQ ID NO |
|---|---|---|---|---|
| Left HA Edit PCR | F8_LeftA_F | 5' homology arm | GGAAGAGCTGGCACTCAGAA | 53 |
| | F8_LeftA_R | editing element | CTTAATATTCTTGGCATCCTCCATG | 54 |
| Left HA Control PCR | F8_LeftB_F | genomic sequence | GCTCCAGAATACACGGTTGTG | 55 |
| | F8_LeftB_R | 5' homology arm | CCATTGACTGTGTGCATTTTAGG | 56 |
| Right HA Edit PCR | F8_RightA_F | editing element | ATGAAGCTTGACGGTGGTTC | 57 |
| | F8_RightA_R | 3' homology arm | TACGTAGATAAGTAGCATGGCG | 58 |
| Right HA Control PCR | F8_RightB_F | 3' homology arm | ATGATACCCATTTCCCTAGATTCC | 59 |
| | F8_RightB_R | genomic sequence | GGCACCACTCCTGAAATACAC | 60 |

TABLE 4

Cycle parameters for ddPCR

| Cycling step | Temp, ° C. | Time (sec) | # of cycles |
|---|---|---|---|
| Enzyme activation | 94 | 60 | 1 |
| Denaturation | 94 | 15 | 25 |
| Annealing | 60 | 15 | |
| Extension | 72 | 60 | |
| Enzyme deactivation | 72 | 60 | 1 |
| Hold(optional) | 4 | infinite | 1 |

Droplet Digital PCR (ddPCR)

Figure 5B:
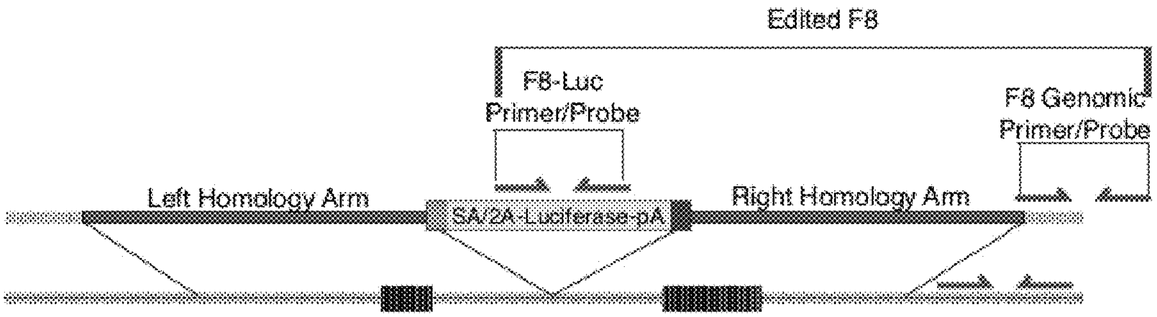
FIG. 5B illustrates the design of a droplet digital PCR (ddPCR) for detecting homologous recombination of the VG-mF8-001-Luc vector into the mouse genome.

Droplet digital PCR partitioned DNA samples into an oil emulsion in which end-point PCR reactions were run and quantified as a binary measurement of molecule density. This method allowed individual analysis of each genomic fragment and quantitation of edited and unedited DNA strands. The TaqMan® primers and probes used are shown in Table 5 below, and their targeting regions are shown in FIG. 5B. Briefly, the DNA samples were diluted in nuclease-free water to 10 ng/μl, and a mixture was made of 12 μl SuperMix no dUTP (BioRad), 0.6 μl of FAM probe (F8), 0.6 μl of VIC probe (SA2A), 4.8 μl of nuclease free water and 6 μl of diluted DNA (60 ng total). Droplets containing the sample mixture were generated using the QX200™ AutoDG™ Automated Droplet generator (BioRad), then transferred to a thermal cycler for PCR. The cycle parameters for the ddPCR are described in Table 6. After the PCR, the droplets were read on the QX200 droplet reader (Bio-Rad) and analyzed using the Quantasoft Software (BioRad). Edited DNA was recognized as a single DNA molecule that carried a payload (as detected by the SA2A assay) and a genomic DNA sequence outside of the homology arms (as detected by the F8 assay). Thus, editing frequencies were calculated based on the detected co-partitioning of the payload and the genomic DNA in a single droplet, in excess of the expected probability of co-partitioning of the payload and the genomic DNA from separate nucleic acid molecules.

TABLE 5

TaqMan ® primers and probes used for quantifying F8 edited DNA

| Assay ID | Assay name | Sequences | SEQ ID NO |
|---|---|---|---|
| mF8_gDNA2_Set1 | F8 | Probe: 5'-/56-FAM/AGTCCATCC/ZEN/ ATGAGATGGAAACAAA/3IABkFQ/-3' | 47 |
| | | Primer 1: 5'-ACAAGCCAATTCTTGAAGTAACAG-3' | 48 |
| | | Primer 2: 5'-TCCTCTATATGATTTGAACTGTCTCC-3' | 49 |
| SA2A_Vector_Set2 | SA2A | Probe: 5'-/5HEX/TTCTAACAT/ZEN/ GCGGTGACGTGGAGG/3IABkFQ/-3' | 50 |
| | | Primer 1: 5'-CCTAGGGCCGGGATTCT-3' | 51 |
| | | Primer 2: 5'-CCTCTTCTCTTCCTCCCACA-3' | 52 |

TABLE 6

Cycle parameters for ddPCR

| Cycling step | Temp, ° C. | Time | ramp rate | # of cycles |
|---|---|---|---|---|
| Enzyme activation | 95 | 10 min | 2.5 C./sec | 1 |
| Denaturation | 95 | 30 sec | | 40 |
| Annealing/extension | 60 | 1 min | | 40 |
| Enzyme deactivation | 98 | 10 min | | 1 |
| Hold(optional) | 4 | infinite | | 1 |

Figure 5C:
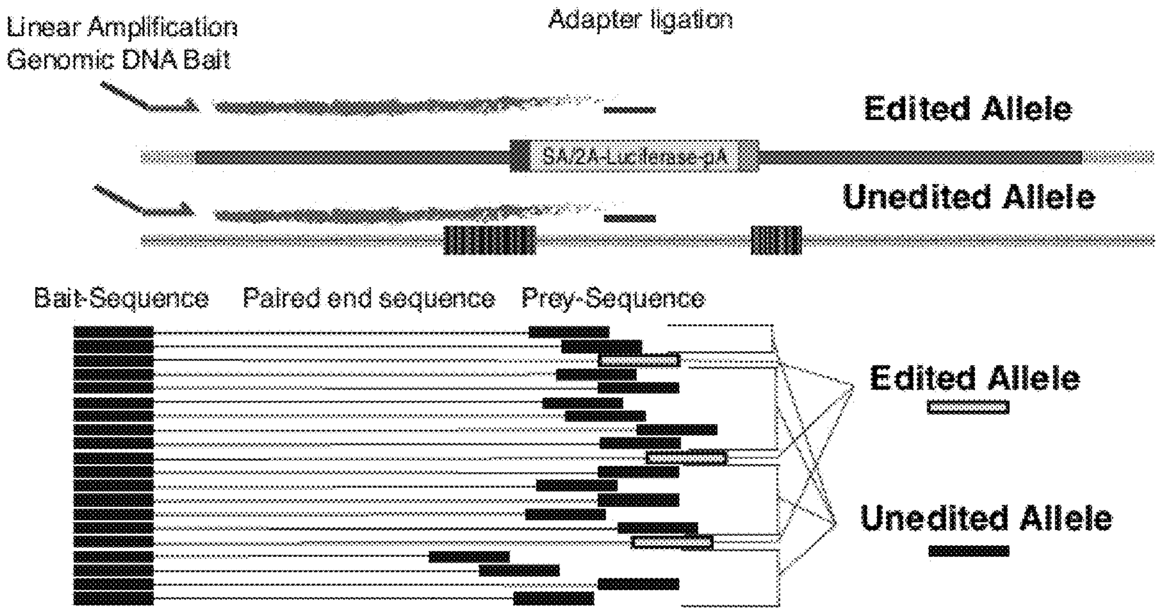
FIG. 5C illustrates the design of a quantitative next-generation sequencing method following linear amplification of the target locus.
Figure 5D:
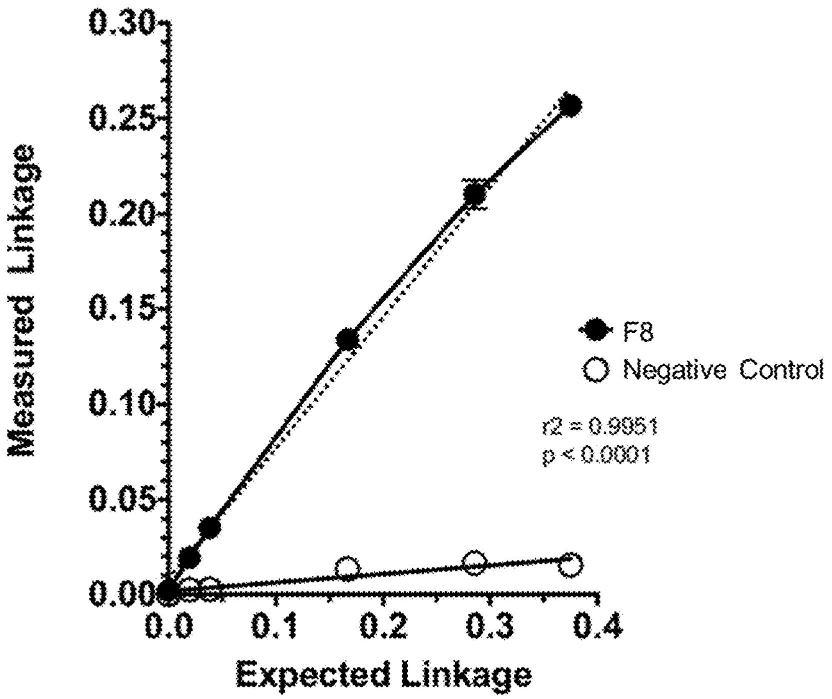
FIG. 5D is a plot showing the measured linkage against the expected linkage in cells transfected with the VG-mF8-001-Luc vector.

To determine if integration occurred at the expected location, genetic linkage was measured between the integrated sequence and the chromosome in which the sequence was integrated into. ddPCR was performed with probes targeting regions as shown in FIG. 5B. As shown in FIG. 5D, the measured linkage correlated well with expected linkage, indicating that integration occurred at the expected location.

Next Generation Sequencing (NGS)

Editing frequencies were also measured by a next generation sequencing assay. An exemplary method was described in Frock et al. (2015) *Nat Biotechnol* 33: 179-186. As shown in FIG. 5C, linear amplification using biotinylated bait primers targeting genomic regions outside of the homology arms were elongated toward the editing insertion site. The single stranded DNA products were purified by streptavidin isolation. Following ligation of NGS adapters and paired end sequencing, editing efficiency was determined as the ratio of reads that extend into the luciferase transgene relative to the unedited insertion site. To ensure accurate quantitation, these genotyping assays were tested against a standard control of artificially constructed editing control samples.

Results

Figure 6A:
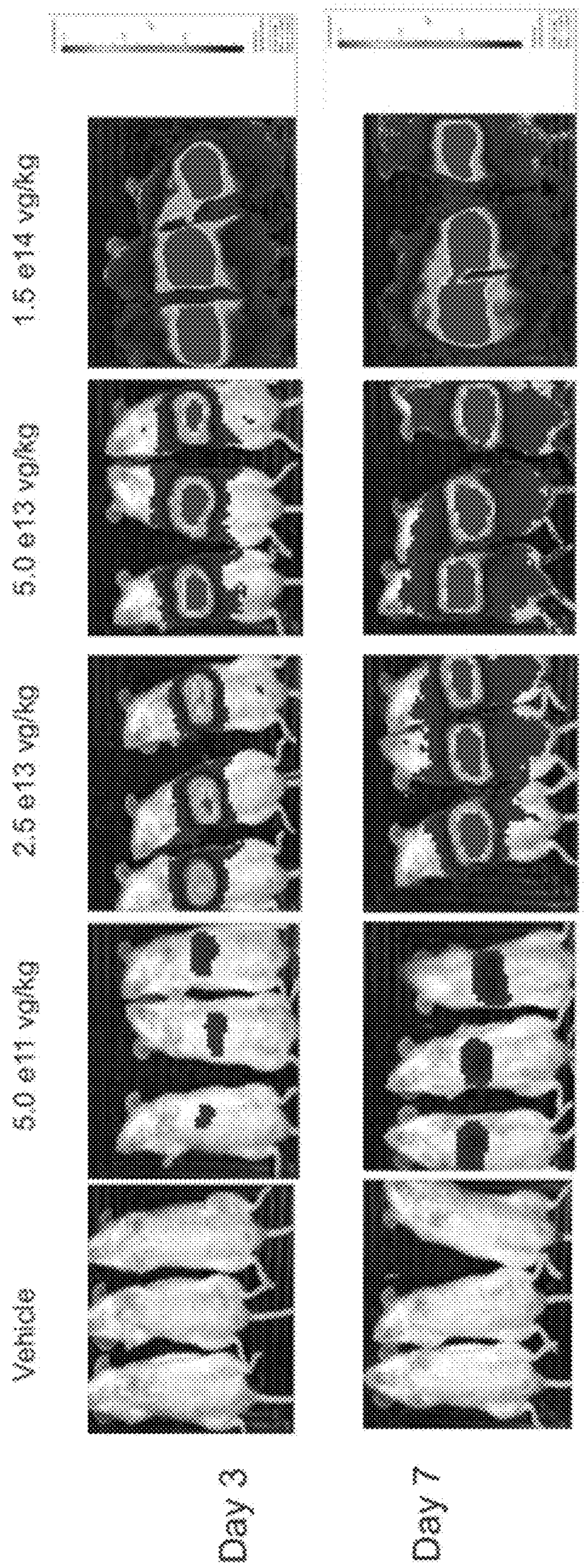
FIG. 6A is a set of photographs showing bioluminescence from mice after administration of the VG-mF8-001-Luc vector at the indicated doses.
Figure 6B:
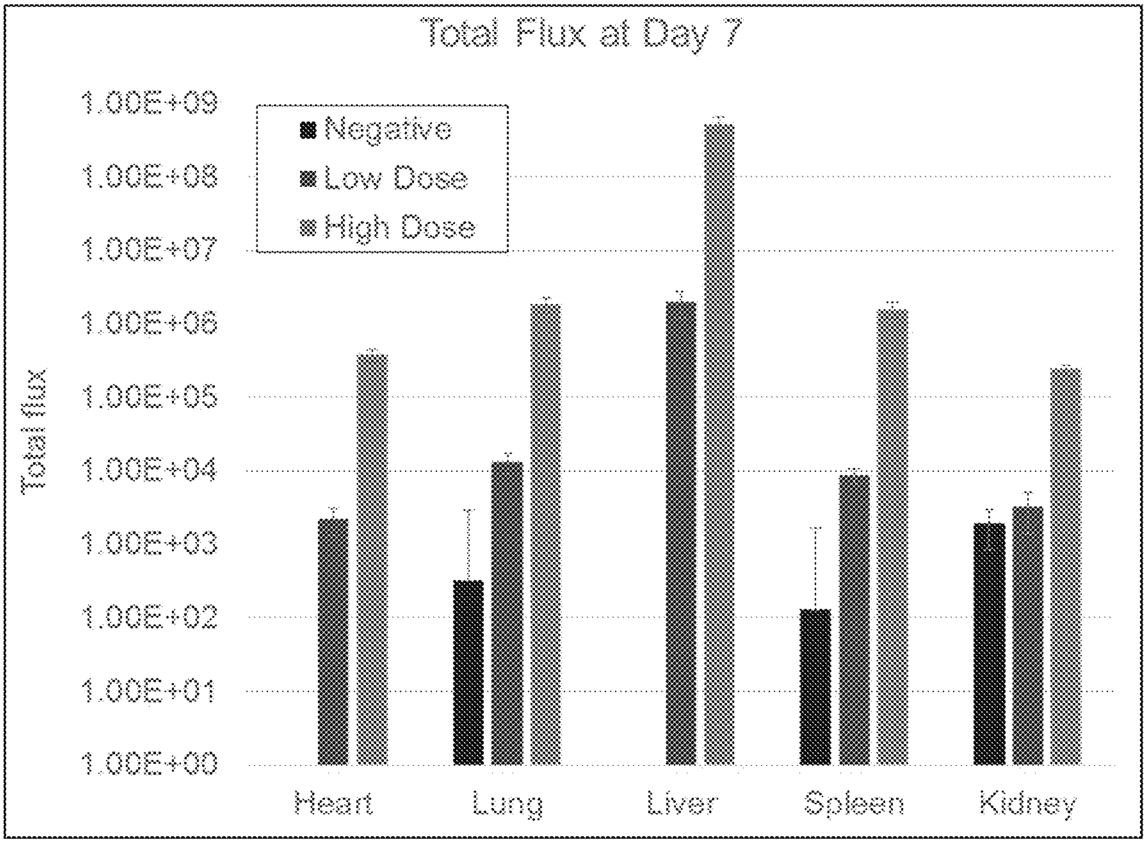
FIG. 6B is a graph showing the total flux of bioluminescence from the indicated organs obtained at day 7 from mice administered a low dose of $1\times10^{11}$ vector genomes or a high dose of $3\times10^{12}$ vector genomes of the VG-mF8-001-Luc vector.
Figure 6C:
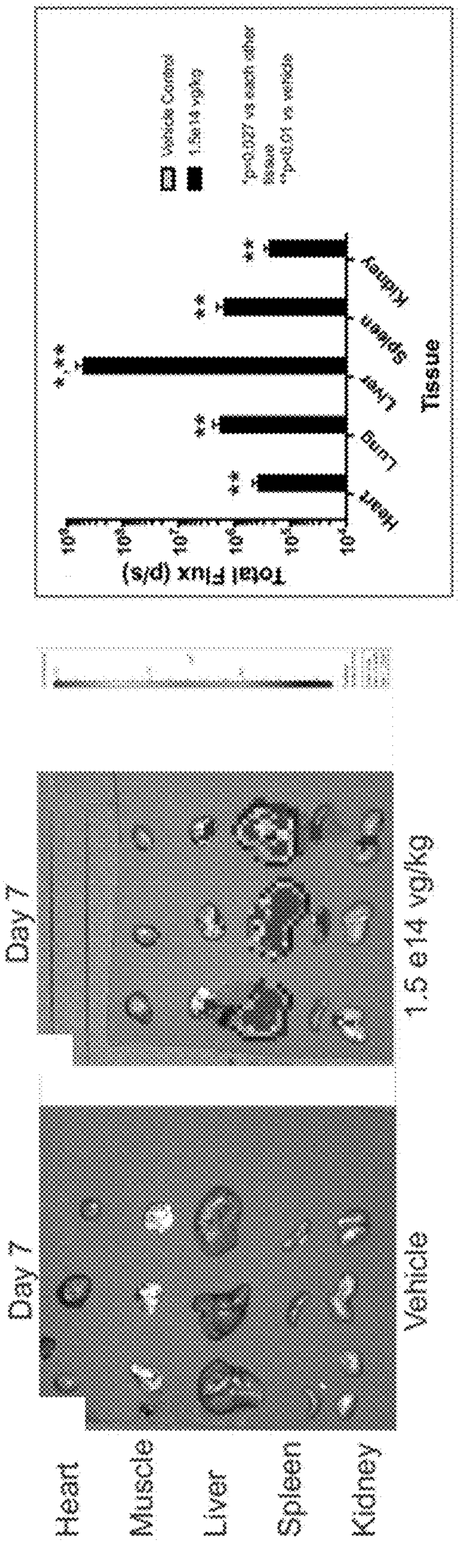
FIG. 6C is a set of photographs showing bioluminescence of the indicated organs obtained at day 7 from mice administered with the indicated dose of the VG-mF8-001-Luc vector. This figure also shows a graph of the total flux of luminiscence from the indicated organs. * indicates a significance level of $p=0.27$ as compared to each other organ; ** indicates a significance level of $p<0.01$ compared to vehicle control.
Figure 6D:
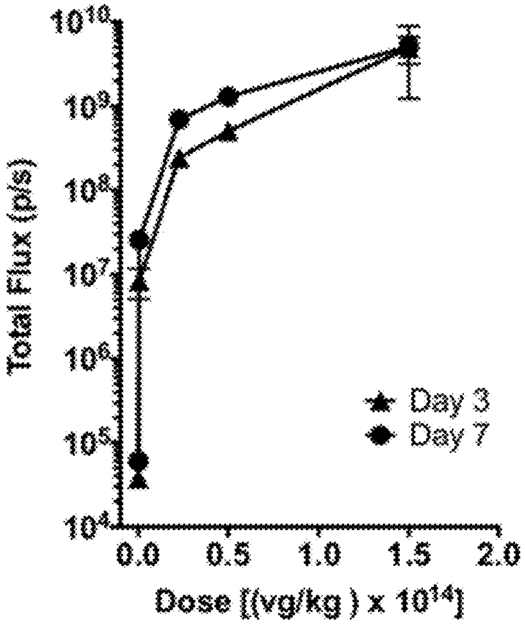
FIG. 6D is a graph showing the total flux of bioluminescence of day 3 and day 7 livers of mice administered the VG-mF8-001-Luc vector across the indicated doses.
Figure 6E:
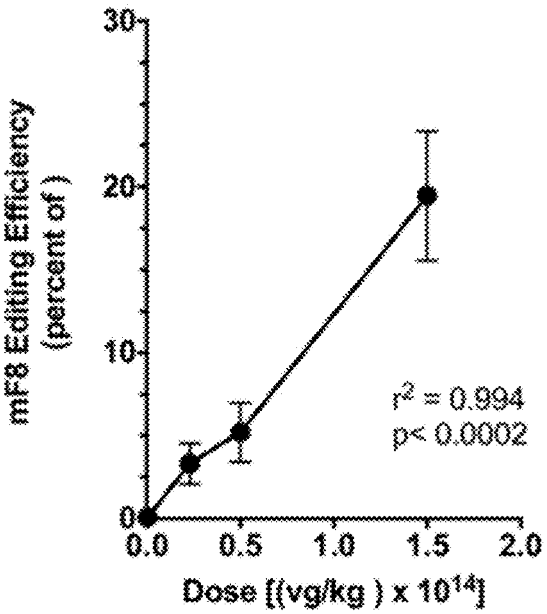
FIG. 6E is a graph showing editing efficiency of the VG-mF8-001-Luc vector in the liver across the indicated doses.
Figure 6F:
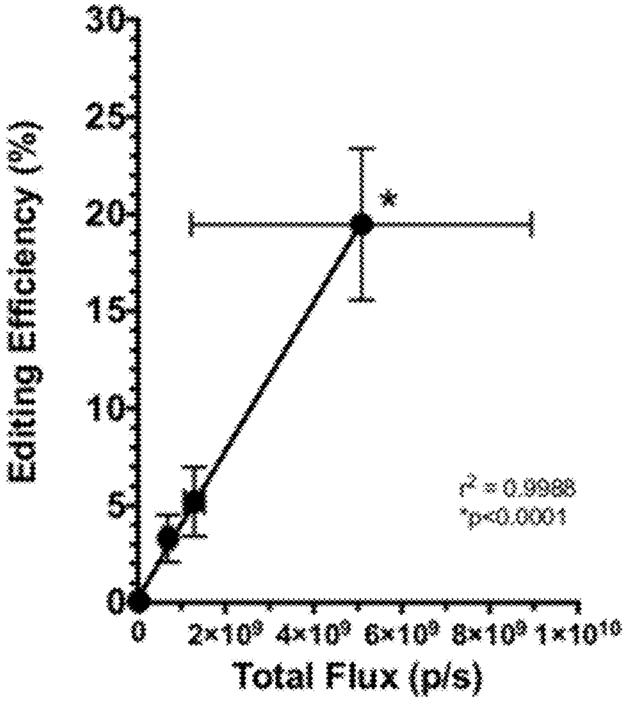
FIG. 6F is a graph showing the editing efficiency of the VG-mF8-001-Luc vector in mouse liver plotted against the total flux of bioluminescence in the liver. * indicates a significance level of $p<0.0001$.

As shown in FIGS. 6A, 6B, and 6C, 7 days after administration of the VG-mF8-001-Luc vector packaged in AAVHSC15, bioluminescence from integrated VG-mF8-001-Luc vector was detected primarily in the liver, but low levels were also observed in heart, lung, spleen, and kidney, in a dose-dependent manner. This result indicated that the editing of the F8 gene by intravenous administration of this vector occurred predominantly in the liver, but also could be detected at lower levels in other major organs. FIG. 6D shows the total flux of bioluminescence in livers of mice administered the VG-mF8-001-Luc vector packaged in AAVHSC15 at various doses, and indicates a dose-dependent response. FIG. 6D shows the editing efficiencies in the liver, as measured by ddPCR, after administration of various doses of the vector. FIG. 6F is a graph showing the editing efficiency of the VG-mF8-001-Luc vector in mouse liver plotted against the total flux of bioluminescence in the liver, and shows a string positive correlation between these two parameters. These data demonstrate that in vivo editing efficiency is dependent on dose of AAVHSC15-VG-mF8-001-Luc administered.

The ability of the AAV vector to edit F8 in vivo was also assessed in a long-term study. Briefly, the VG-mF8-001-Luc vector genome was packaged in AAVHSC15 or AAVHSC17 (see WO 2016/049230 A1). A dose of $5.8\times10^{12}$ vector genomes per kilogram of body weight was injected intravenously via tail vein to each NOD.CB17-Prkdc$^{scid}$/NCrCrl (NOD/SCID) 6-8-week old male mouse. The mice were sacrificed 63 days after the vector injection, and liver samples were collected. Serial bioluminescent imaging of whole mice over time and editing efficiency measurement in the liver samples were performed using the same methods as described above.

Figure 7A:
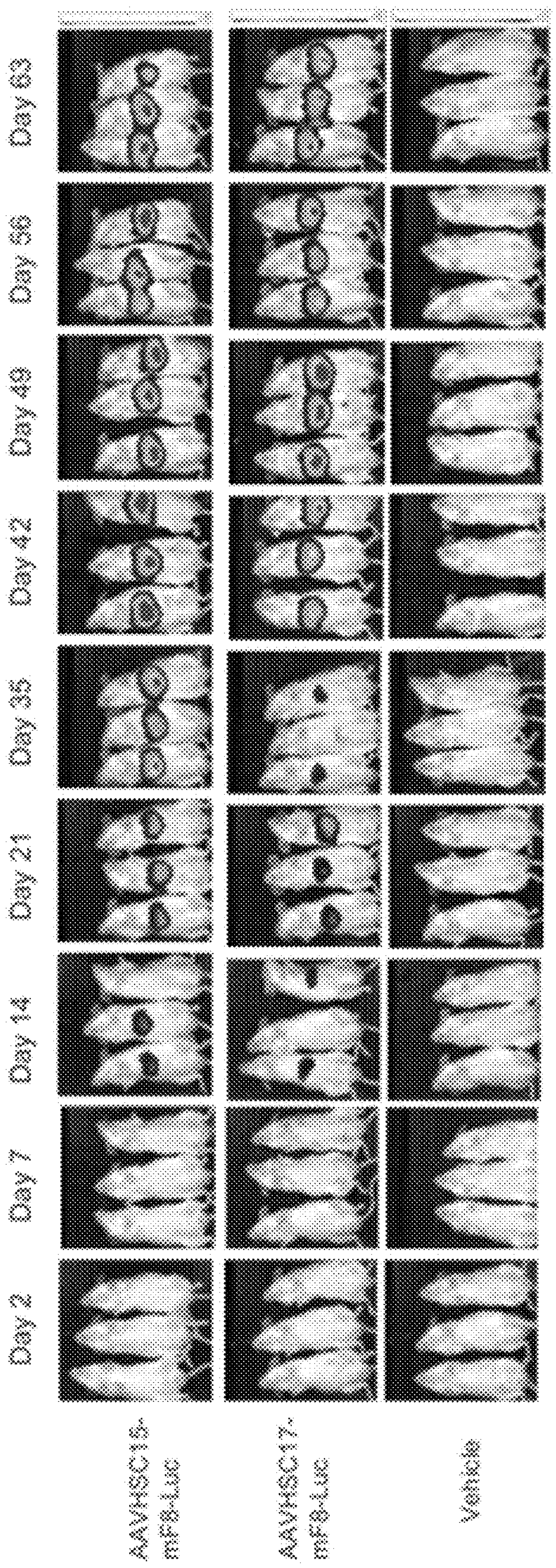
FIG. 7A is a set of photographs showing bioluminescence images from mice up to 63 days after administration of the VG-mF8-001-Luc vector packaged in AAVHSC15 or AAVHSC17 capsid.
Figure 7B:
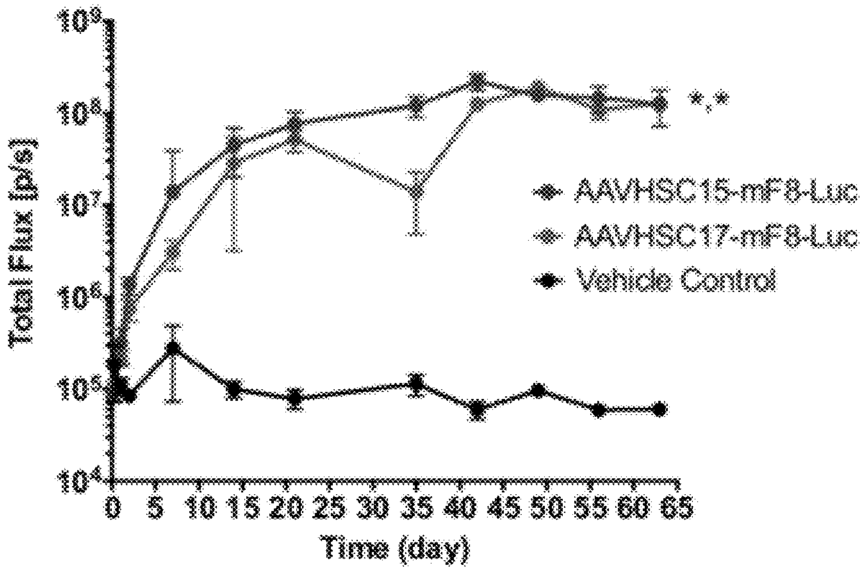
FIG. 7B is a graph showing the total flux of bioluminescence from these mice plotted against days post administration of vector (n=3 per treatment group). * indicates a significance level of $p<0.004$ compared to vehicle control.

Luminescence from integrated VG-mF8-001-Luc vector was initially detectable within 24 hours after the administration of the vector packaged in either AAVHSC15 or AAVHSC17, and reached a plateau approximately 40 days after the administration (FIG. 7B). The bioluminescence levels remained high 63 days after the administration (FIG.

Figure 7C:
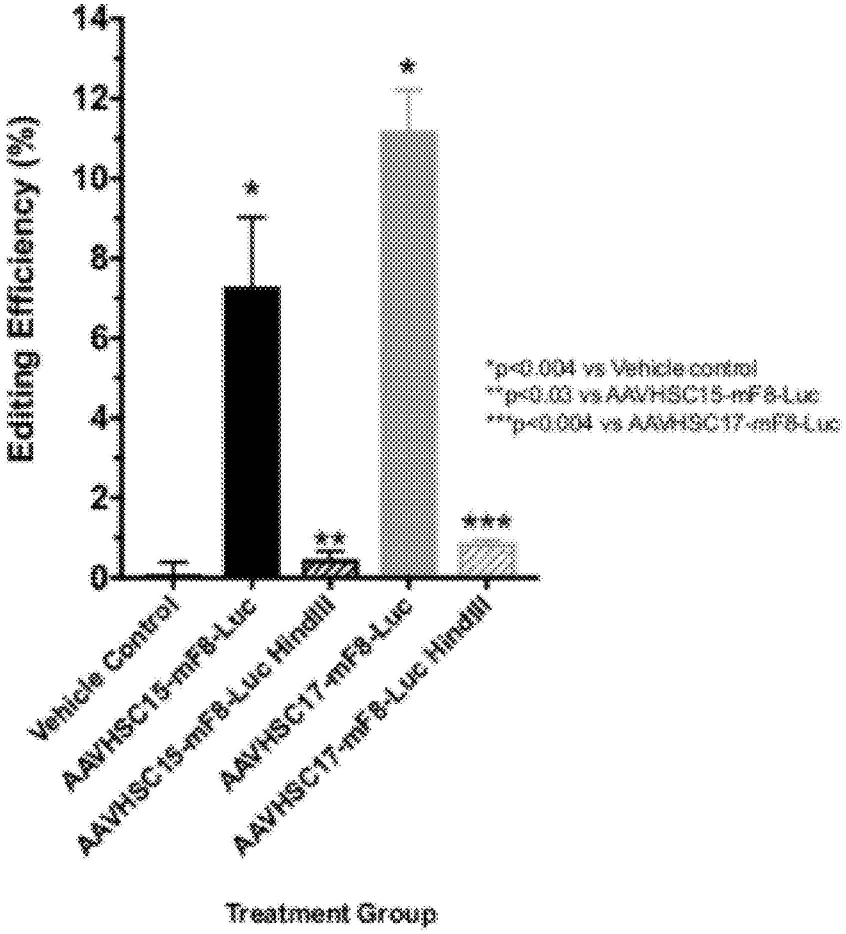
FIG. 7C is a graph showing the editing efficiency in cells obtained from mice administered the VG-mF8-001-Luc vector packaged in AAVHSC15 or AAVHSC17 capsids. Vectors indicated with "HindIII" refer to vectors that have been treated with the HindIII restriction enzyme; these vectors act as a negative control by artificially separating the inserted payload from the target genomic DNA. * indicates a significance level of $p<0.004$ compared to vehicle control;  indicates a significance level of $p<0.03$ compared to the VG-mF8-001-Luc vector packaged in AAVHSC15 capsids (AAVHSC15-mF8-Luc); * indicates a significance level of $p<0.004$ compared to the VG-mF8-001-Luc vector packaged in AAVHSC17 capsids (AAVHSC17-mF8-Luc).
Figure 7D:
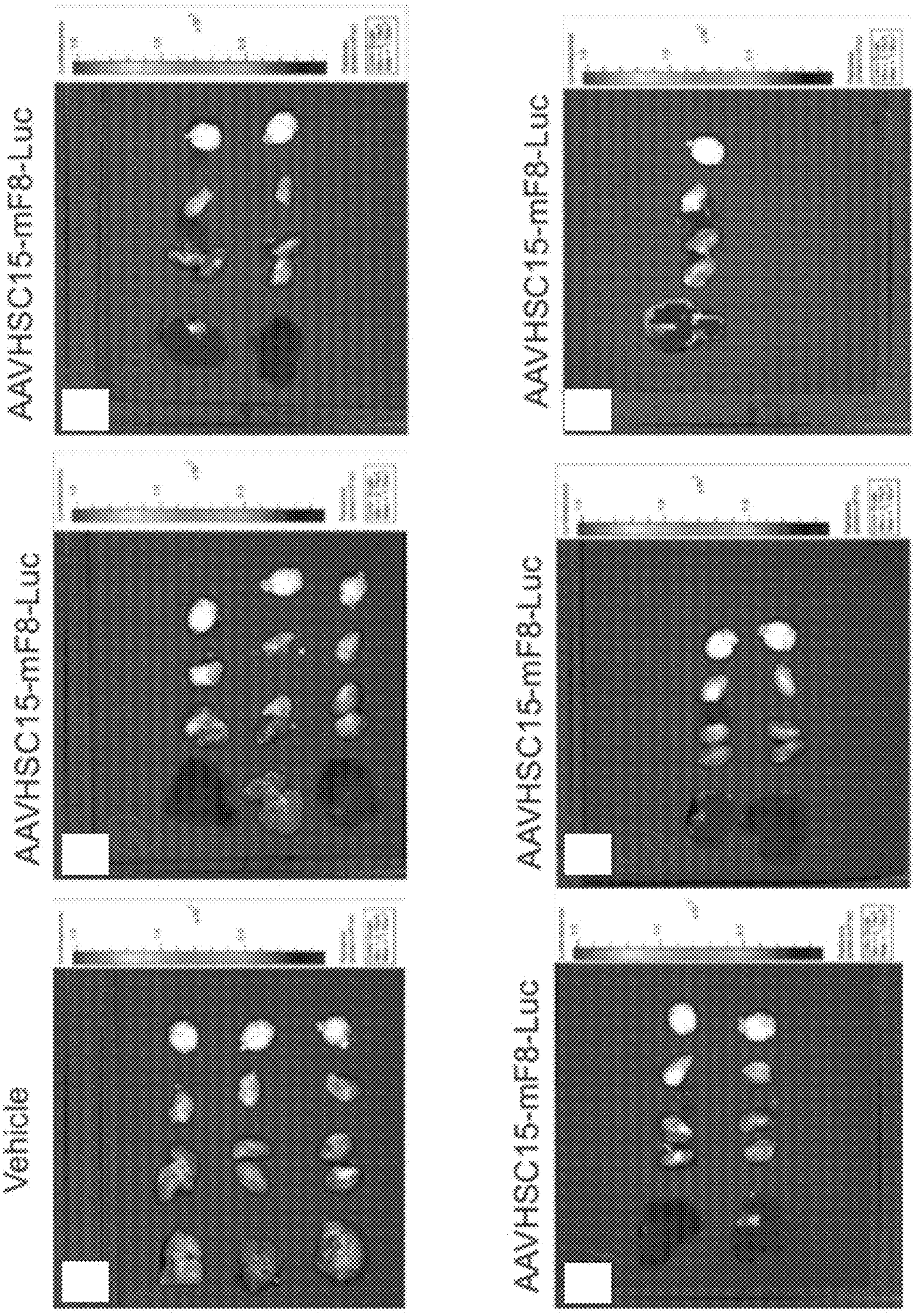
FIG. 7D is a set of photographs showing bioluminescence images of the liver, kidney, muscle, and brain tissues (from left to right in each photograph) of mice at various time points post administration of the VG-mF8-001-Luc vector packaged in AAVHSC15 capsid (AAVHSC15-mF8-Luc). The various time points increase from left to right in the top row and continue from left to right in the bottom row of photographs.
Figure 7E:
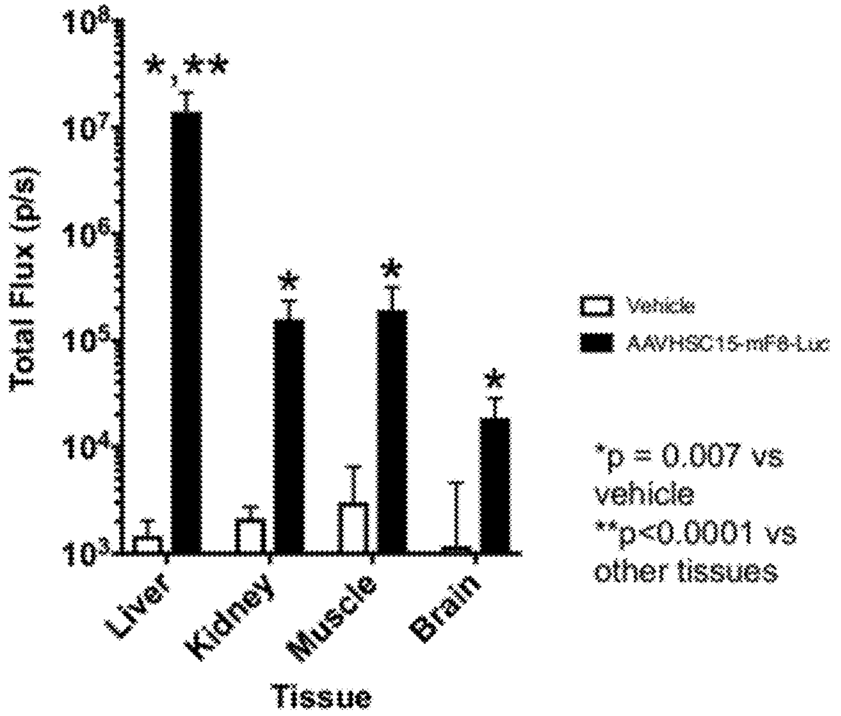
FIG. 7E is a graph showing the total flux of bioluminescence of the liver, kidney, muscle, and brain tissues of mice administered the VG-mF8-001-Luc vector packaged in AAVHSC15 capsids. * indicates a significance level of $p=0.007$ compared to vehicle control; ** indicates a significance level of $p<0.0001$ compared to other tissues.
Figure 7F:
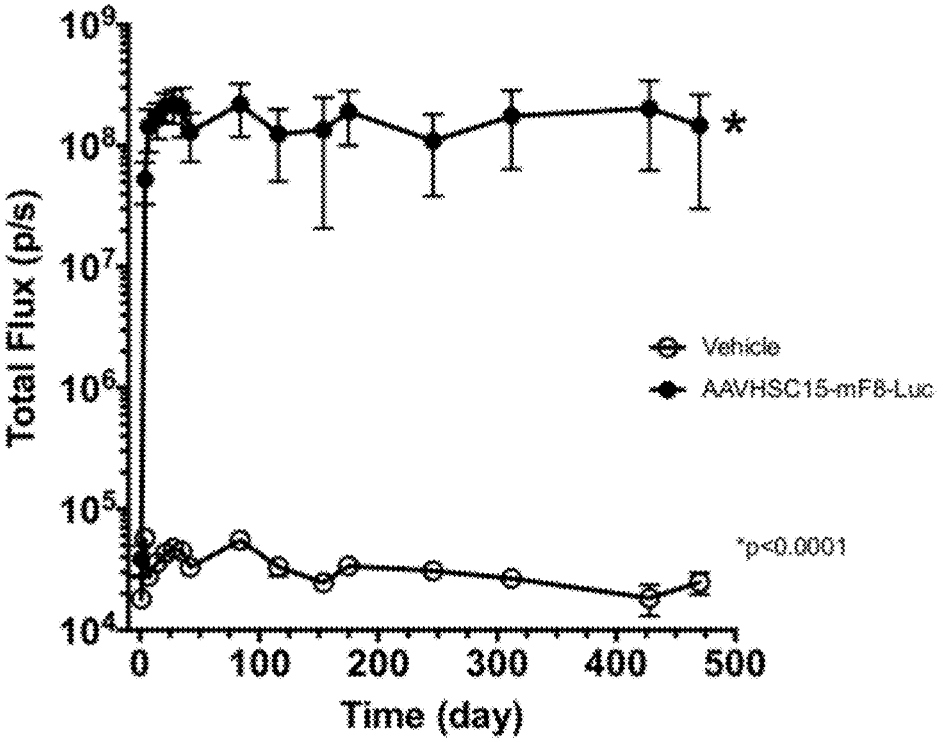
FIG. 7F is a graph showing the total flux of bioluminescence in mice administered the VG-mF8-001-Luc vector packaged in AAVHSC15 capsids up to 470 days after administration. * indicates a significance level of $p<0.0001$ compared to vehicle control.

7A). FIG. 7C shows the editing efficiency measured in cells obtained from mice administered the VG-mF8-001-Luc vector packaged in AAVHSC15 or AAVHSC17 capsids. Vectors indicated with "HindIII" refer to vectors that have been treated with the HindIII restriction enzyme; these vectors act as a negative control by artificially separating the inserted payload from the target genomic DNA. Bioluminescence was observed in the liver samples of the mice 7 days post injection of the vector packaged in the AAVHSC15 vector (FIG. 7D). As shown in FIG. 7E, bioluminescence was detected at significantly higher levels in the liver as compared to tissues of other major organs. FIG. 7F shows that the bioluminescence in normal mice administered the VG-mF8-001-Luc vector packaged in AAVHSC15 capsids is detected for at least 470 days. Taken together, these data indicate that intravenous delivery of the VG-mF8-001-Luc vector packaged in AAVHSC15 or AAVHSC17 capsids result in durable editing of the F8 locus in mice.

Figure 10A:
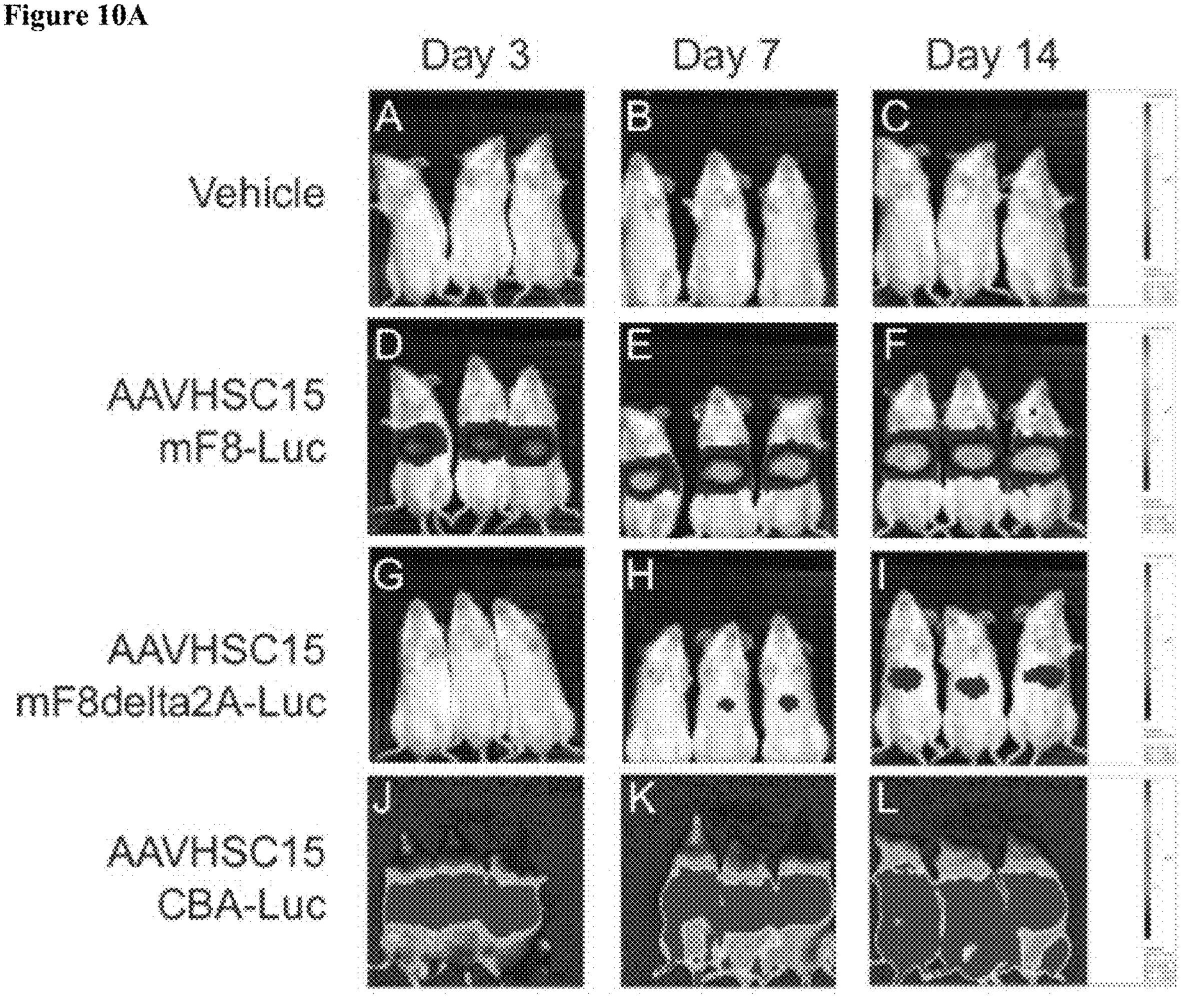
FIG. 10A is a set of photographs of day 3, day 7, and day 14 mice administered the indicated vectors. As positive control, a vector comprising a luciferase encoding sequence driven by a chicken β-actin (CBA) promoter was used.
Figure 10B:
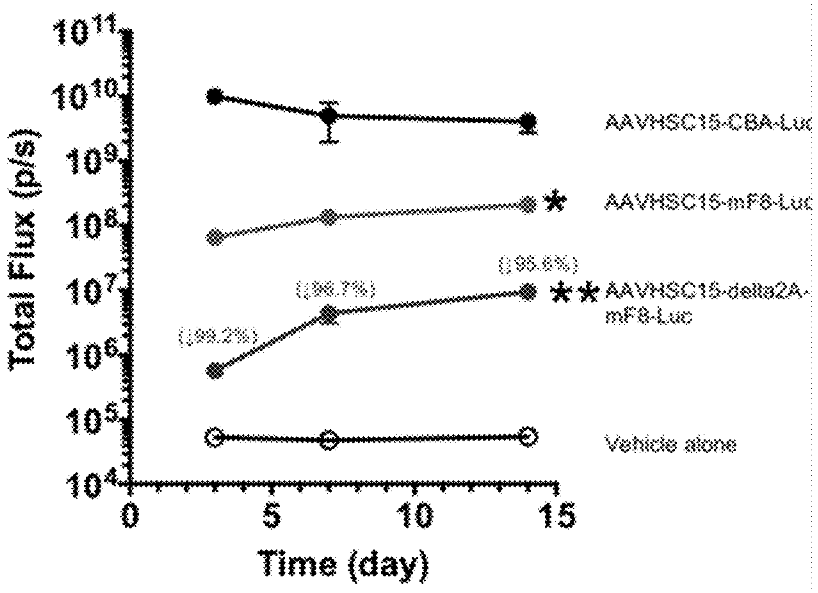
FIG. 10B is a graph showing the total flux of bioluminescence in mice administered the indicated vectors. * indicates a significance level of $p<0.0001$ compared to mice administered the mF8delta2A-luc vector; ** indicates a significance level of $p<0.0001$ compared to vehicle control.
Figure 10C:
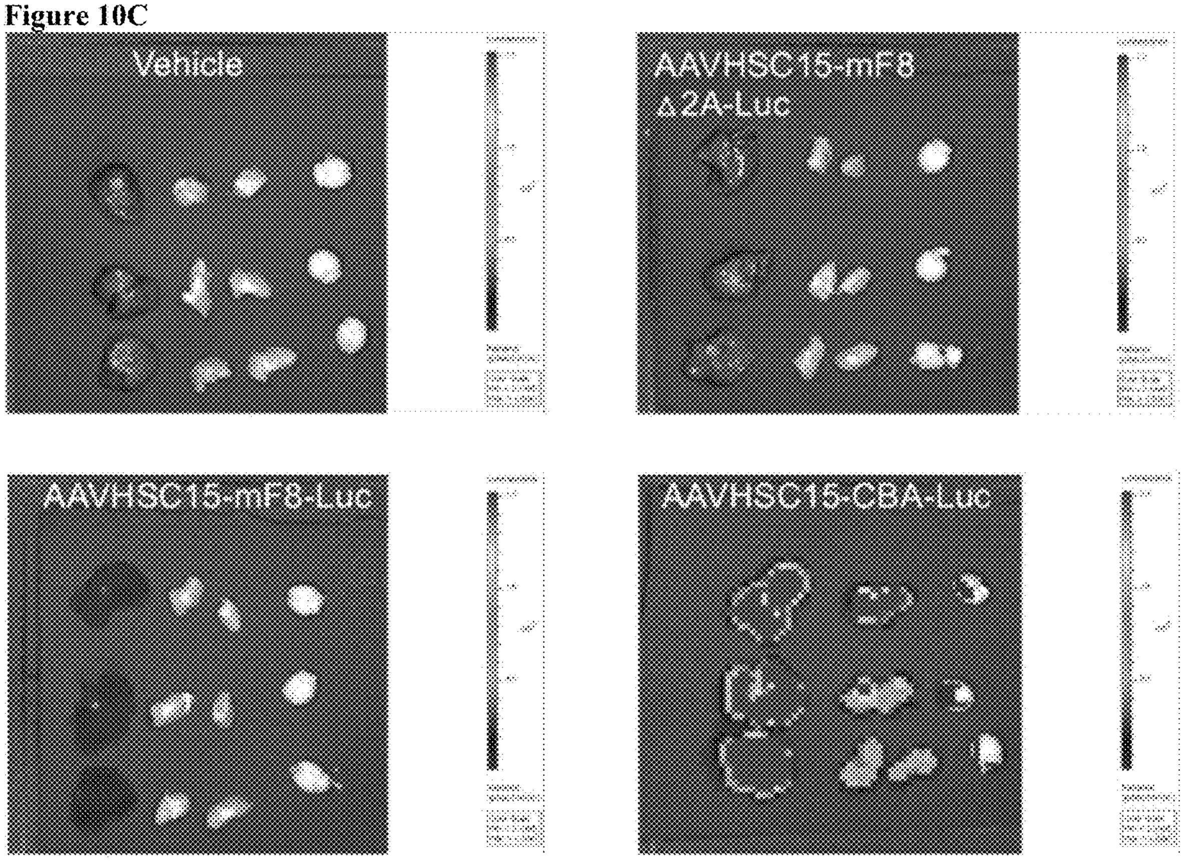
FIG. 10C is a set of photographs showing, from top to bottom, the liver, brain, and kidney obtained from mice administered the indicated vectors.
Figure 10D:
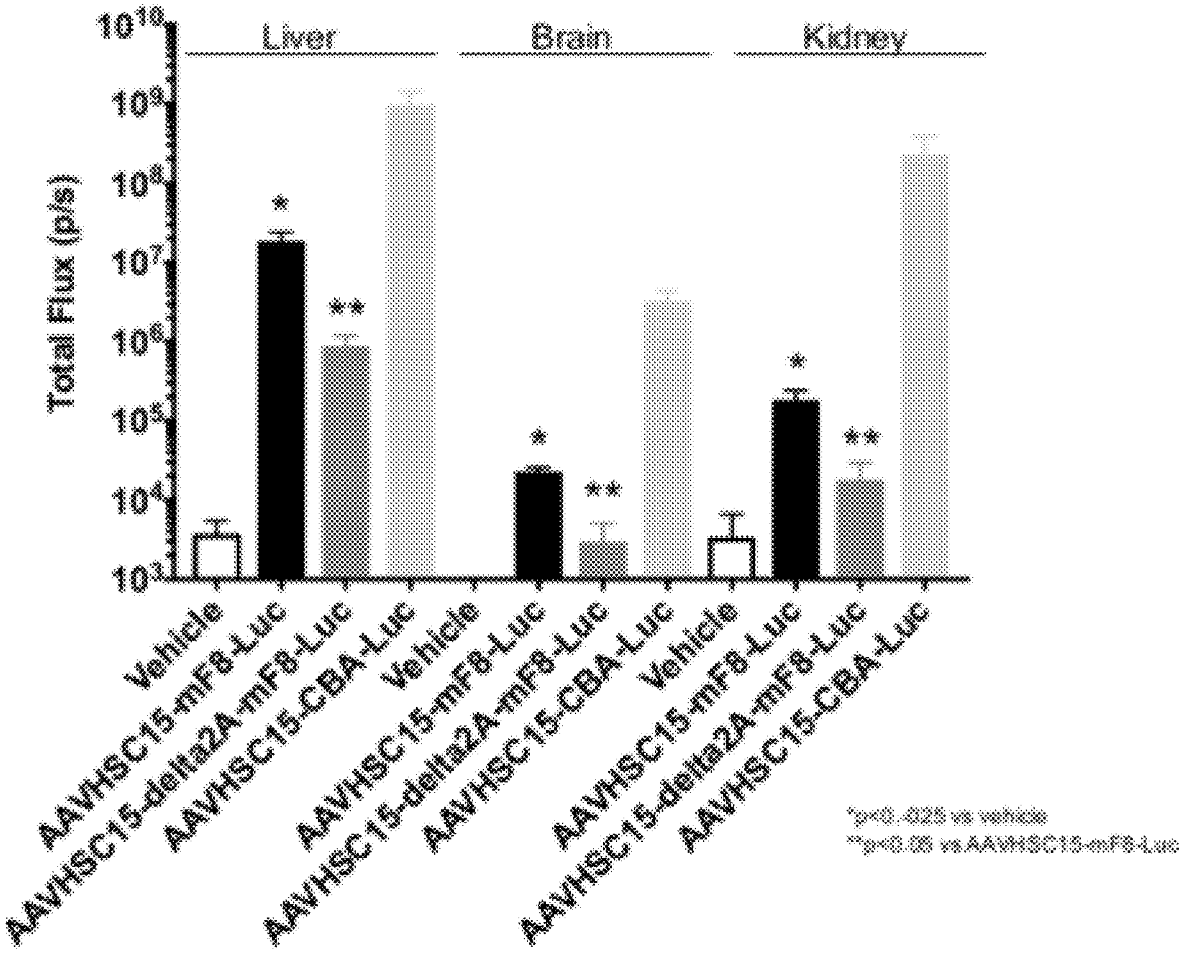
FIG. 10D is a graph showing the total flux of bioluminescence in each of these tissues obtained from mice administered the indicated vectors.
Figure 10E:
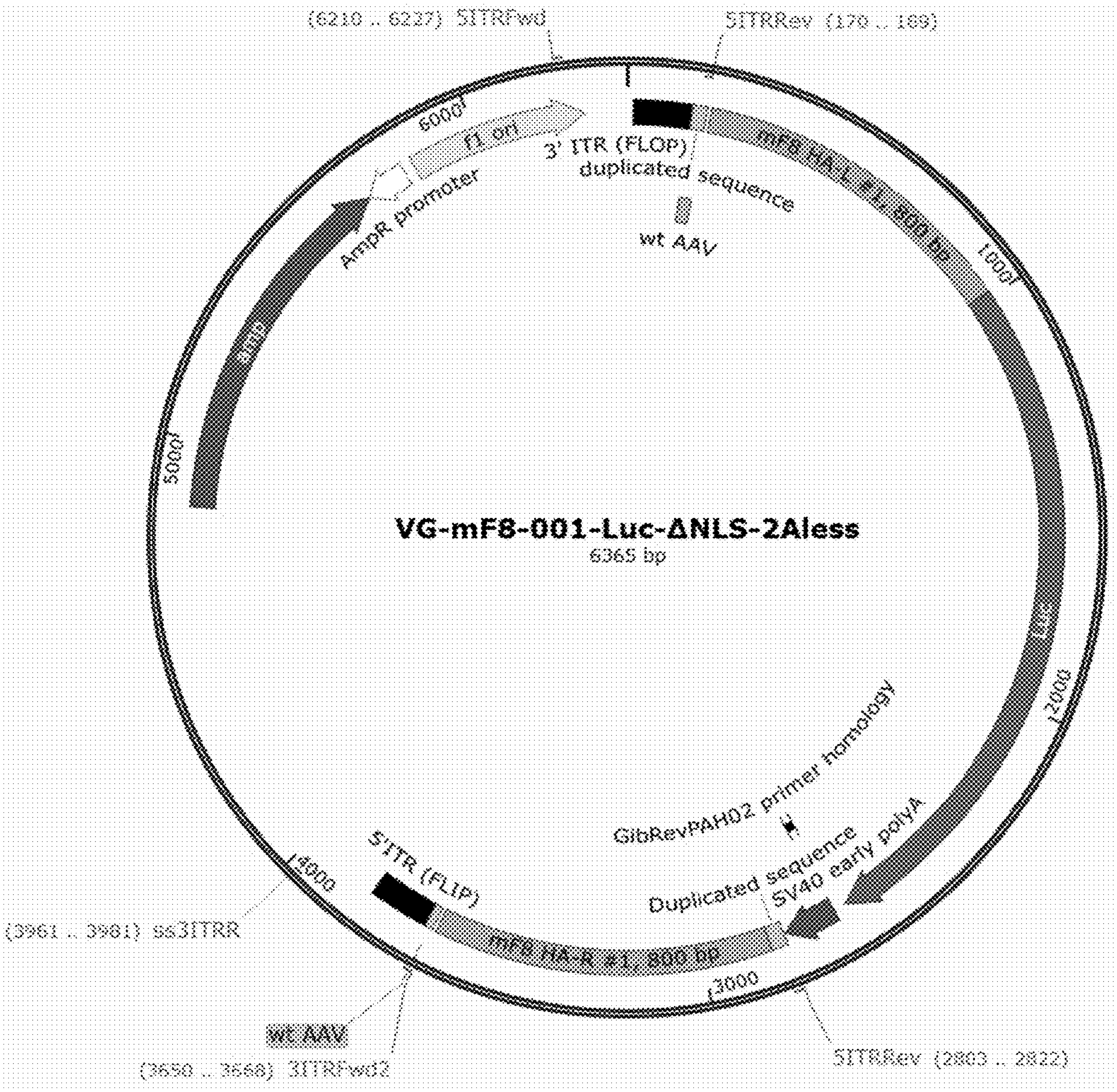
FIG. 10E is a map of the mF8delta2A-luc vector.

In contrast, removal of the splice acceptor from the VG-mF8-001-Luc vector greatly reduced luciferase expression in mice. See FIG. 10E for a map of the mF8delta2A-luc vector. Mice administered the mF8delta2A-luc vector packaged in AAVHSC15 capsids showed greatly reduced bioluminescence compared to the intact vector (FIG. 10A). When quantified, it was determined that mice administered the mF8delta2A-luc vector exhibited in a 96% loss of observable bioluminescence relative to the intact vector (FIG. 10B). As shown in FIG. 10C, bioluminescence was greatly reduced in the livers of mice administered the mF8delta2A-luc vector packaged in AAVHSC15 capsids compared to the intact vector. Reduction in bioluminescence was also observed in brain and kidney tissues (FIG. 10D).

Figure 8A:
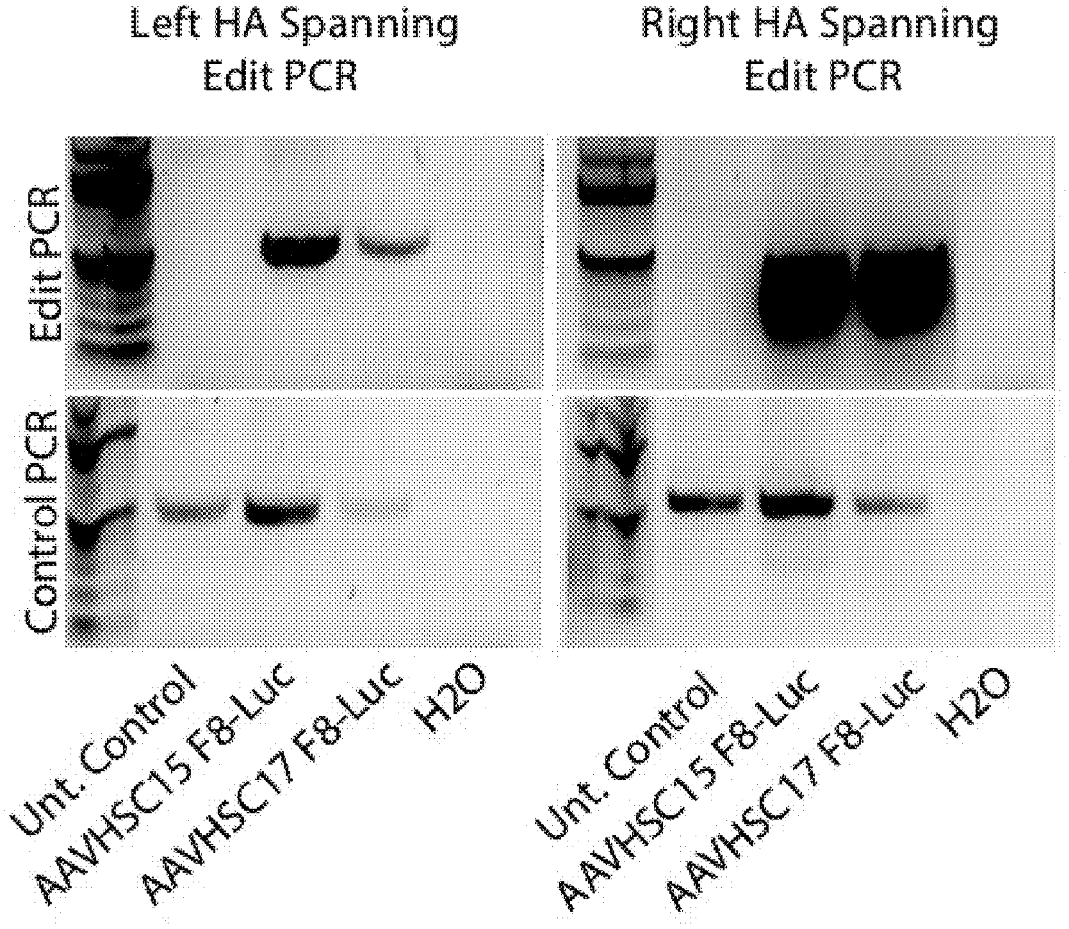
FIG. 8A is a set of gel electrophoresis graphs showing the PCR products amplified from liver samples of mice injected with the VG-mF8-001-Luc vector packaged in AAVHSC15 and AAVHSC17 capsids.
Figure 8B:
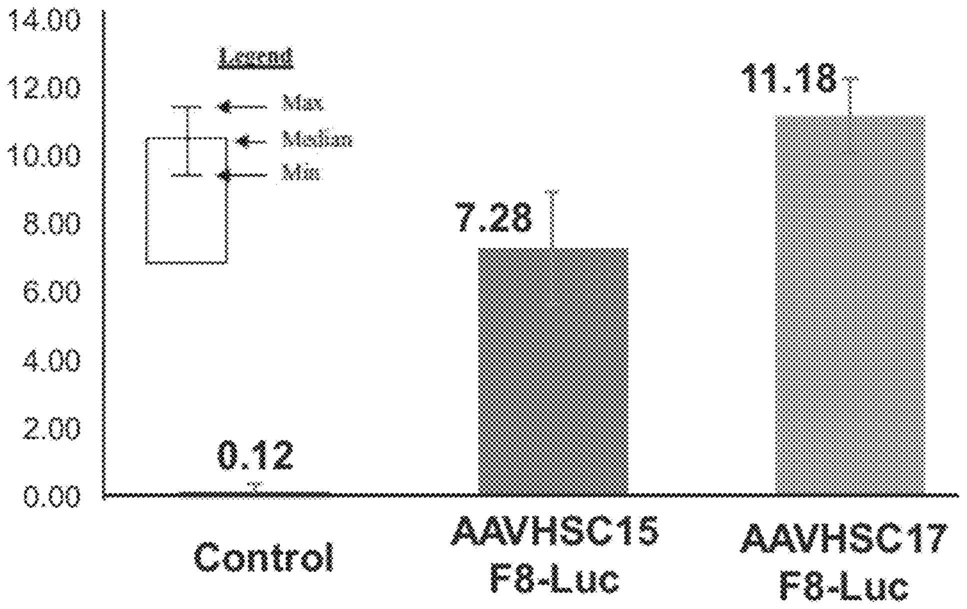
FIG. 8B is a graph showing the editing efficiency in the liver of these mice as measured by ddPCR.
Figure 8C:
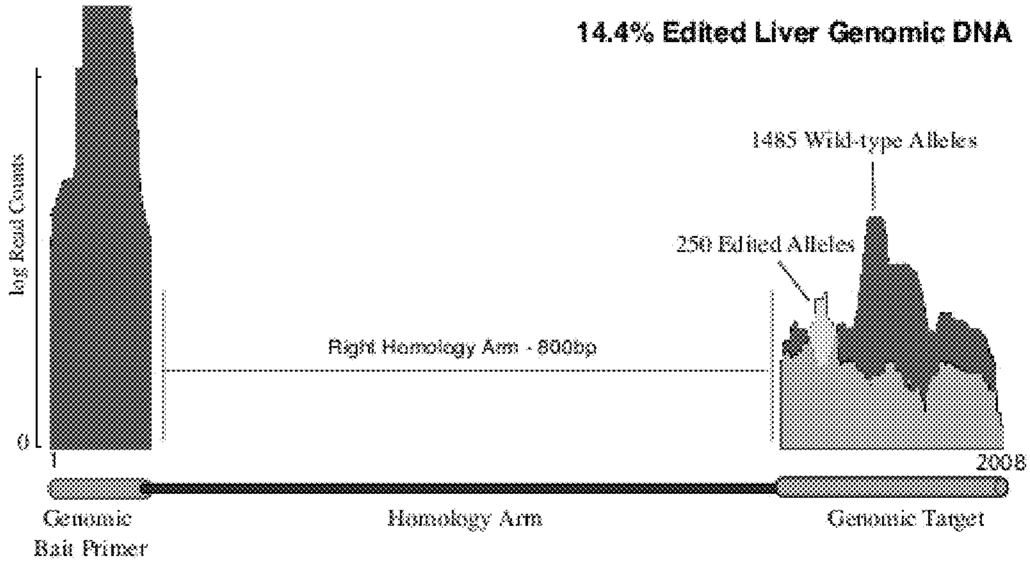
FIG. 8C is a graph showing the analysis of the next-generation sequencing results of the target locus in liver samples of mice injected with the VG-mF8-001-Luc vector packaged in AAVHSC15 capsid.
Figure 9A:
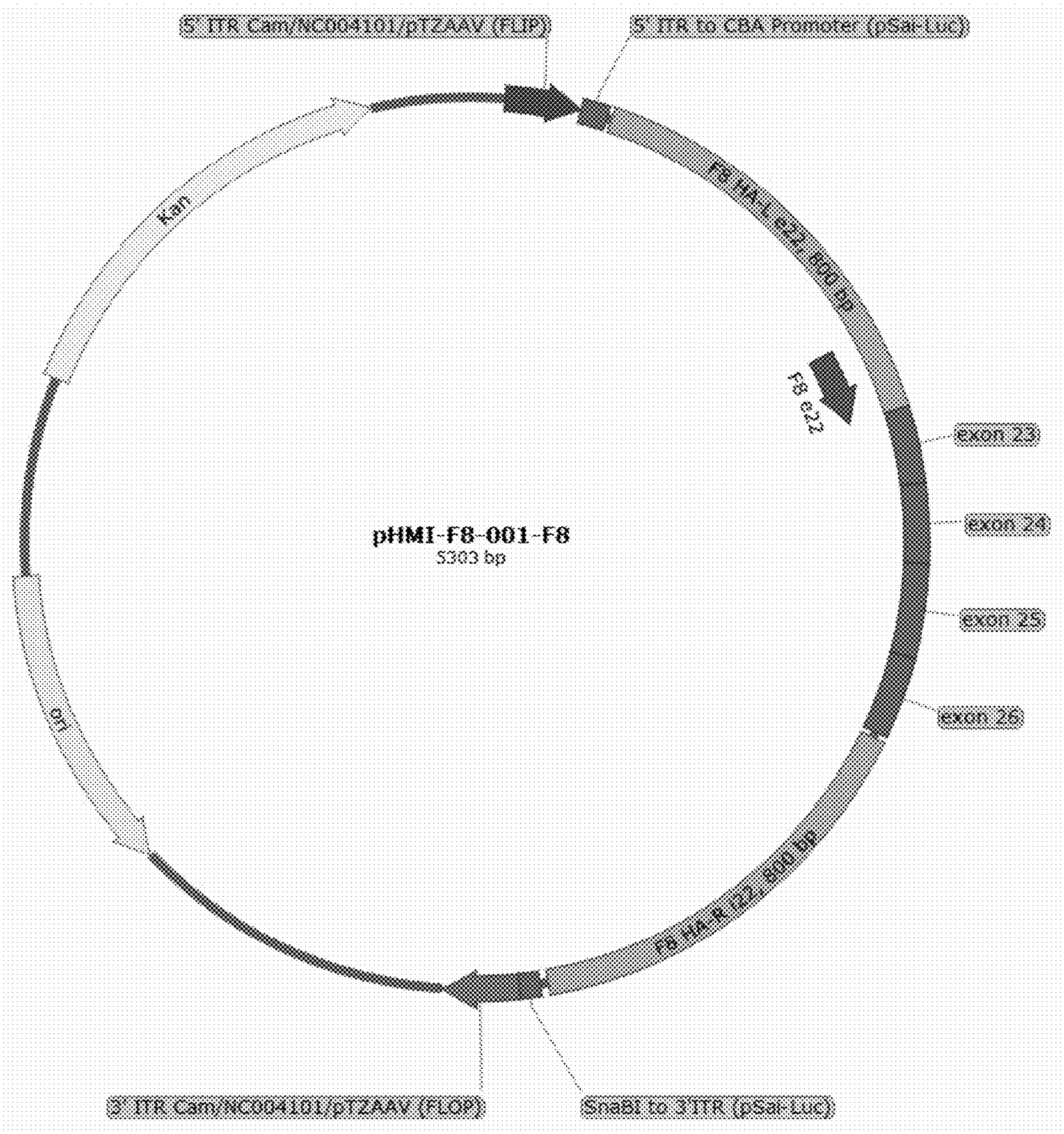
FIGS. 9A, 9B, 9C, and 9D are maps of the pHMI-F8-001-F8, pHMI-F8-002-F8, pHMI-F8-003-F8, and pHMI-F8-004-F8 vectors, respectively.
Figure 9B:
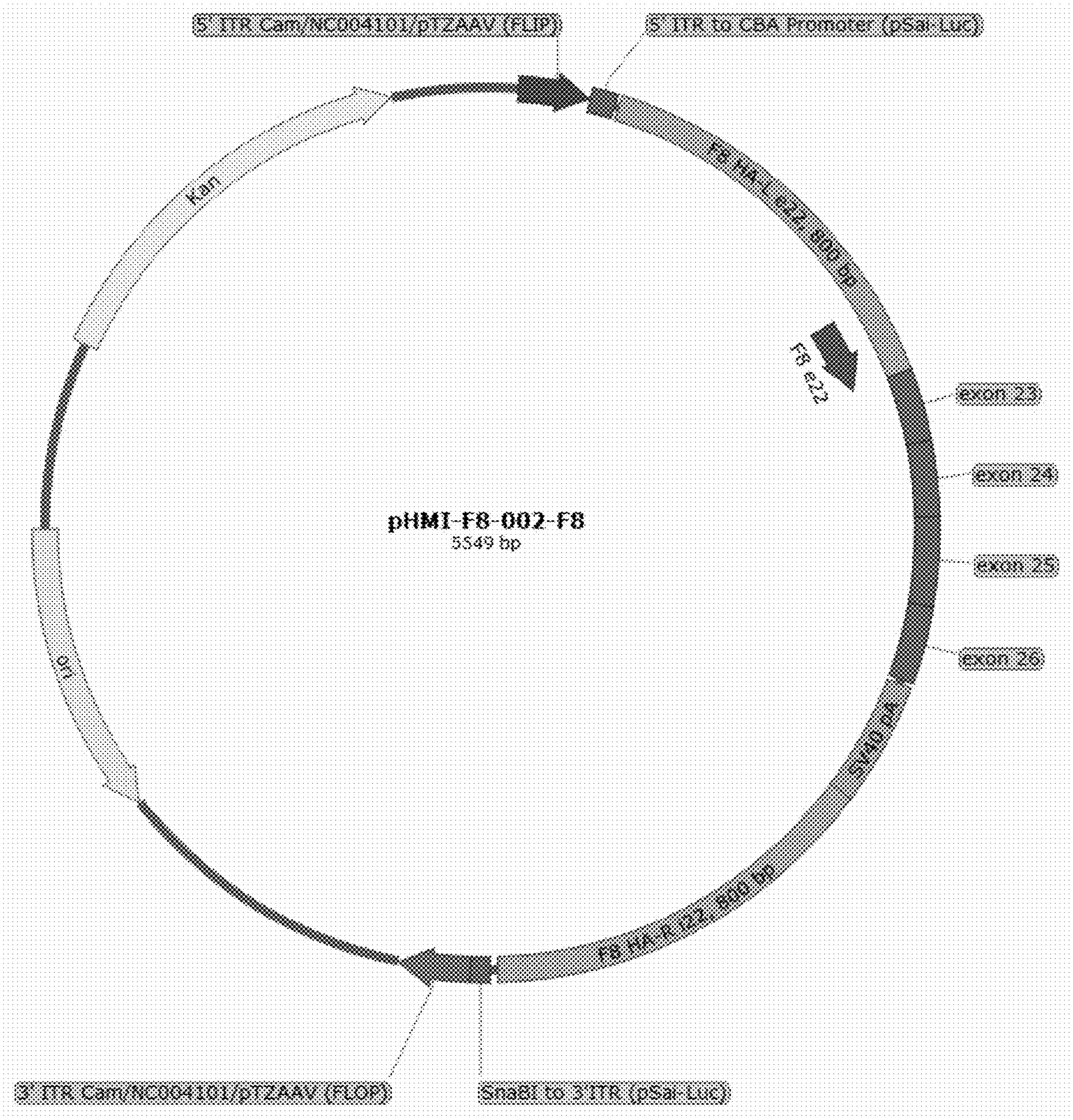
Figure 9C:
Figure 9D:
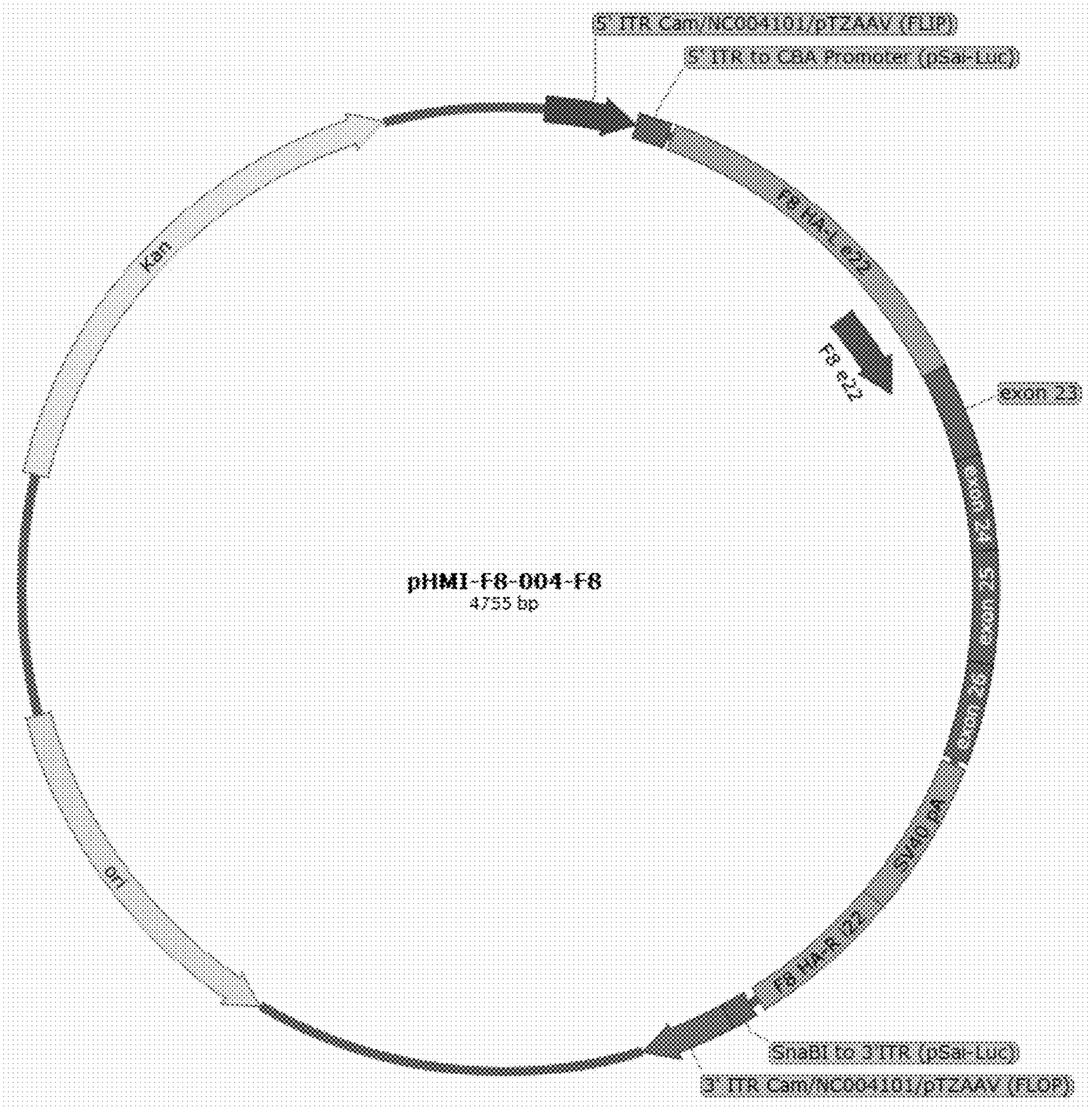

To detect editing of the F8 gene, DNA samples from the mouse liver 9 weeks post administration of the VG-mF8-001-Luc vector were analyzed by end-point PCR, droplet digital PCR, and next generation sequencing as described above. As shown in FIG. 8A, editing-specific PCR products were detected in liver samples of the mice injected with the VG-mF8-001-Luc vector packaged in AAVHSC15 and AAVHSC17. Editing efficiencies in the liver, as measured by ddPCR, were approximately 7% and 11% in the mice that received injections of the vector packaged in AAVHSC15 and AAVHSC17, respectively (FIG. 8B). Next generation sequencing detected a similar editing efficiency of 14.4% in liver samples of the mice injected with the VG-mF8-001-Luc vector packaged in AAVHSC15 (FIG. 8C).

The results above suggest that intravenous administration of an F8 correction vector may alter (e.g., restore) the expression of F8 from a liver cell with high efficiency.

FIG. 7C is a graph showing the editing efficiency in cells obtained from mice administered the VG-mF8-001-Luc vector packaged in AAVHSC15 or AAVHSC17 capsids. * indicates a significance level of $p<0.004$ compared to vehicle control. Vectors indicated with "HindIII" refer to vectors that have been treated with the HindIII restriction enzyme; these vectors act as a negative control by artificially separating the inserted payload from the target genomic DNA.  indicates a significance level of $p<0.03$ compared to the VG-mF8-001-Luc vector packaged in AAVHSC15 capsids (AAVHSC15-mF8-Luc); * indicates a significance level of $p<0.004$ compared to the VG-mF8-001-Luc vector packaged in AAVHSC17 capsids (AAVHSC17-mF8-Luc). FIG. 7D is a set of photographs showing bioluminescence images of the liver, kidney, muscle, and brain tissues (from left to right in each photograph) of mice at various time points post administration of the VG-mF8-001-Luc vector packaged in AAVHSC15 capsid (AAVHSC15-mF8-Luc). The various time points increase from left to right in the top row and continue from left to right in the bottom row of photographs. FIG. 7E is a graph showing the total flux of bioluminescence of the liver, kidney, muscle, and brain tissues of mice administered the VG-mF8-001-Luc vector packaged in AAVHSC15 capsids. * indicates a significance level of $p=0.007$ compared to vehicle control; ** indicates a significance level of $p<0.0001$ compared to other tissues. FIG. 7F is a graph showing the total flux of bioluminescence in mice administered the VG-mF8-001-Luc vector packaged in AAVHSC15 capsids up to 470 days after administration. * indicates a significance level of $p<0.0001$ compared to vehicle control.

Example 4: F8 Correction Vectors for Insertion of an F8 Coding Sequence into the F8 Gene This example provides F8 correction vectors pHMI-F8-001-F8, pHMI-F8-002-F8, pHMI-F8-003-F8, and pHMI-F8-004-F8, each containing an F8 coding sequence for insertion after the last nucleotide of exon 22 of the human F8 gene. These vectors are capable of restoring the expression of F8 from a mutant F8 gene locus having an intron 22 inversion.

The vector maps of pHMI-F8-001-F8, pHMI-F8-002-F8, pHMI-F8-003-F8, and pHMI-F8-004-F8 are shown in FIGS. 9A, 9B, 9C, and 9D, respectively. Each of these vectors comprises the following elements 5' to 3': a 5' ITR ("5' ITR Cam/NC004101/pTZAAV (FLIP)"); a 5' homology arm ("F8 HA-L e22, 800 bp" or "F8 HA-L e22"); the coding sequence of exons 23-26 of human F8 ("exon 23," "exon 24," "exon 25," and "exon 26"); an optional SV40 polyadenylation sequence ("SV40 pA" in pHMI-F8-002-F8 and pHMI-F8-004-F8 only); a 3' homology arm ("F8 HA-R i22, 800 bp" or "F8 HA-R i22"); and a 3' ITR ("3' ITR Cam/NC004101/pTZAAV (FLOP)"). The sequences of these elements are set forth in Table 7. A targeted integration restriction cassette ("TI RE cassette") comprising recognition and cleavage sites for unique restriction endonucleases may be inserted downstream from the polyadenylation sequence, facilitating detection of the desired homologous recombination.

TABLE 7

Genetic elements in F8 correction vectors

| | SEQ ID NO | | | |
|---|---|---|---|---|
| Genetic Element | pHMI-F8-001-F8 | pHMI-F8-002-F8 | pHMI-F8-003-F8 | pHMI-F8-004-F8 |
| 5' ITR element | 18 | 18 | 18 | 18 |
| 5' homology arm | 27 | 27 | 31 | 31 |
| partial coding sequence of human F8 (exons 22-26) | 26 | 26 | 26 | 26 |
| SV40 polyadenylation sequence | N/A | 37 | N/A | 37 |
| 3' homology arm | 28 | 28 | 32 | 32 |
| 3' ITR element | 19 | 19 | 19 | 19 |
| coding sequence cassette (including partial F8 coding sequence and SV40 polyadenylation sequence) | N/A | 33 | N/A | 33 |

TABLE 7-continued

Genetic elements in F8 correction vectors

| Genetic Element | SEQ ID NO pHMI-F8-001-F8 | pHMI-F8-002-F8 | pHMI-F8-003-F8 | pHMI-F8-004-F8 |
|---|---|---|---|---|
| correction genome (from 5' homology arm to 3' homology arm) | 38 | 39 | 40 | 41 |
| correction genome (from 5' ITR to 3' ITR) | 42 | 43 | 44 | 45 |

The 5' homology arm comprises the wild-type genomic sequence upstream of the insertion site, wherein the insertion site is the internucleotide bond between exon 22 and intron 22 of the F8 gene. The 3' homology arm comprises the wild-type genomic sequence downstream from the insertion site. Integration of the pHMI-F8-001-F8, pHMI-F8-002-F8, pHMI-F8-003-F8, or pHMI-F8-004-F8 vector into the human genome allows transcription of the F8 locus into a pre-mRNA comprising 5' to 3' the following elements: a portion of the F8 pre-mRNA from the endogenous 5' end to the insertion site, and the partial F8 coding sequence (exons 22-26, excluding polyadenylation sequence). Splicing of this pre-mRNA generates an mRNA comprising 5' to 3' the following elements: exon 1, intron 1, exon 2, intron 2, exon 3, intron 3, exon 4, intron 4, exon 5, intron 5, exon 6, intron 6, exon 7, intron 7, exon 8, intron 8, exon 9, intron 9, exon 10, intron 10, exon 11, intron 11, exon 12, intron 12, exon 13, intron 13, exon 14, intron 14, exon 15, intron 15, exon 16, intron 16, exon 17, intron 17, exon 18, intron 18, exon 19, intron 19, exon 20, intron 20, exon 21, intron 21, exon 22, exon 23, exon 24, exon 25, and exon 26. An endogenous polyadenylation sequence is present downstream from the mutant F8 gene having an intron 22 inversion. Thus, transcription of the edited F8 gene will be properly terminated though the pHMI-F8-001-F8 and pHMI-F8-003-F8 vectors do not comprise a polyadenylation sequence. An SV40 polyadenylation sequence is added in the pHMI-F8-002-F8 and pHMI-F8-004-F8 vectors to ensure efficient transcription termination. Integration of any one of these vectors into the human genome inserts the coding sequence of exons 23-26 of human F8, thereby restoring the expression of a wild-type F8 protein that has been impaired by mutations (e.g., intron 22 inversion) downstream from exon 22 of the F8 gene.

The vectors are packaged with a clade F AAV capsid (e.g., AAVHSC7, AAVHSC15, and AAVHSC17). The packaged virus is examined in vitro for assessment of targeted integration. B lymphoblastoid cells are cultured in RPMI-1640 medium supplemented with 15% fetal calf serum (FCS) and 2 mM L-glutamine. Cells are seeded at approximately 200,000 cells per mL and split when cells reach approximately 500,000 to 1,000,000 cells per mL. Cells are in log phase growth on the day of transduction. Cells are counted and an appropriate number of cells are plated. Typically, 10,000 cells are plated for flow cytometry analysis. Vectors are thawed on ice and sonicated on ice if necessary prior to transductions. Virus is added to each well individually and media is pipetted up and down to evenly distribute virus. Vector does not exceed 10% of the culture volume. Vector is calculated based on the titer and MOI and is calculated before plating to ensure proper plates are used.

Forty-eight hours after transduction, cells transduced with the vector are harvested using FACS Buffer (1×PBS, 2% FCS, 0.1% sodium azide). Cells are spun down at 1200 RPM for 10 minutes. FACS buffer is removed so that approximately 200 μL remains. DAPI (100 μM working stock) is added immediately before flow cytometry analysis to a final concentration of 3 μM.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

We claim:

1. A method for correcting a mutation in an F8 gene in a cell, the method comprising transducing the cell with a replication-defective adeno-associated virus (AAV) comprising:

a) an AAV capsid comprising an AAV Clade F capsid protein; and b) a correction genome comprising from 5' to 3':

(i) a 5' AAV ITR nucleotide sequence;

(ii) a 5' homology arm nucleotide sequence of up to 2000 nucleotides in length, comprising a nucleotide sequence that is at least 99% identical to SEQ ID NO: 27;

(iii) an editing element for editing a target locus in the F8 gene, comprising an F8 nucleotide sequence that encodes an amino acid sequence consisting of the amino acid sequence encoded by SEQ ID NO: 26 operably linked to a polyadenylation sequence;

(iv) a 3' homology arm nucleotide sequence of up to 2000 nucleotides in length, comprising a nucleotide sequence that is at least 99% identical to SEQ ID NO: 28; and (v) a 3' AAV ITR nucleotide sequence, wherein the cell is transduced without co-transducing or co-administering an exogenous nuclease or a nucleotide sequence that encodes an exogenous nuclease.

2. The method of claim 1, wherein the cell is a hepatocyte or an endothelial cell, optionally wherein the endothelial cell is a hepatic sinusoidal endothelial cell, and optionally wherein the cell is in a mammalian subject and the AAV is administered to the subject in an amount effective to transduce the cell in the subject.

3. A method for treating a subject having a disease or disorder associated with an F8 gene mutation, the method comprising administering to the subject an effective amount of a replication-defective AAV comprising:

a) an AAV capsid comprising an AAV Clade F capsid protein; and b) a correction genome comprising from 5' to 3':

(i) a 5' AAV ITR nucleotide sequence;

(ii) a 5' homology arm nucleotide sequence of up to 2000 nucleotides in length, comprising a nucleotide sequence that is at least 99% identical to SEQ ID NO: 27;

(iii) an editing element for editing a target locus in the F8 gene, comprising an F8 nucleotide sequence that encodes an amino acid sequence consisting of the amino acid sequence encoded by SEQ ID NO: 26 operably linked to a polyadenylation sequence;

(iv) a 3' homology arm nucleotide sequence of up to 2000 nucleotides in length, comprising a nucleotide sequence that is at least 99% identical to SEQ ID NO: 28; and (v) a 3' AAV ITR nucleotide sequence, wherein an exogenous nuclease or a nucleotide sequence that encodes an exogenous nuclease is not co-administered to the subject, optionally wherein the disease or disorder is hemophilia A and optionally wherein the subject is a human subject.

4. The method of claim 1, wherein the F8 nucleotide sequence is silently altered.

5. The method of claim 1, wherein the target locus is the internucleotide bond between nucleotide 126,476 and nucleotide 126,477 of the F8 gene.

6. The method of claim 1, wherein the target locus is the internucleotide bond between nucleotide 126,476 and nucleotide 126,477 of the F8 gene.

7. The method of claim 1, wherein the polyadenylation sequence is an exogenous polyadenylation sequence.

8. The method of claim 1, wherein the polyadenylation sequence is an SV40 polyadenylation sequence.

9. The method of claim 1, wherein the polyadenylation sequence comprises the nucleotide sequence set forth in SEQ ID NO: 23.

10. The method of claim 1, wherein the 5' AAV ITR nucleotide sequence has at least 95% sequence identity to SEQ ID NO: 18 or 46, and/or the 3' AAV ITR nucleotide sequence has at least 95% sequence identity to SEQ ID NO: 19, 61, or 63.

11. The method of claim 1, wherein the 5' AAV ITR nucleotide sequence has at least 95% sequence identity to SEQ ID NO: 20, and/or the 3' AAV ITR nucleotide sequence has at least 95% sequence identity to SEQ ID NO: 21.

12. The method of claim 1, wherein the correction genome comprises a nucleotide sequence selected from the group consisting of SEQ ID NOs: 39, 41, 43, and 45.

13. The method of claim 1, wherein the correction genome consists of a nucleotide sequence selected from the group consisting of SEQ ID NOs: 39, 41, 43, and 45.

14. The method of claim 1, wherein the integration efficiency of the editing element into the target locus is at least 2% when the AAV is contacted in vitro in the absence of an exogenous nuclease with a population of B lymphoblastoid cells under standard AAV transduction conditions.

15. The methods The method of claim 1, wherein the allelic frequency of integration of the editing element into the target locus is at least 1% when the AAV is contacted in vitro in the absence of an exogenous nuclease with a population of B lymphoblastoid cells under standard AAV transduction conditions.

16. The method of claim 1, wherein the AAV Clade F capsid protein comprises an amino acid sequence having at least 95% sequence identity with the amino acid sequence of amino acids 203-736 of SEQ ID NO: 1, 2, 3, 4, 6, 7, 10, 11, 12, 13, 15, 16, or 17, optionally wherein: the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G, optionally wherein:

(a) the amino acid in the capsid protein corresponding to amino acid 626 of SEQ ID NO: 2 is G, and the amino acid in the capsid protein corresponding to amino acid 718 of SEQ ID NO: 2 is G;

(b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;

(c) the amino acid in the capsid protein corresponding to amino acid 505 of SEQ ID NO: 2 is R, and the amino acid in the capsid protein corresponding to amino acid 687 of SEQ ID NO: 2 is R;

(d) the amino acid in the capsid protein corresponding to amino acid 346 of SEQ ID NO: 2 is A, and the amino acid in the capsid protein corresponding to amino acid 505 of SEQ ID NO: 2 is R; or (e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C, optionally wherein the capsid protein comprises the amino acid sequence of amino acids 203-736 of SEQ ID NO: 1, 2, 3, 4, 6, 7, 10, 11, 12, 13, 15, 16, or 17.

17. The method of claim 1, wherein the AAV Clade F capsid protein comprises an amino acid sequence having at least 95% sequence identity with the amino acid sequence of amino acids 138-736 of SEQ ID NO: 1, 2, 3, 4, 5, 6, 7, 9, 10, 11, 12, 13, 15, 16, or 17, optionally wherein: the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G, optionally wherein:

(a) the amino acid in the capsid protein corresponding to amino acid 626 of SEQ ID NO: 2 is G, and the amino acid in the capsid protein corresponding to amino acid 718 of SEQ ID NO: 2 is G;

(b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;

(c) the amino acid in the capsid protein corresponding to amino acid 505 of SEQ ID NO: 2 is R, and the amino acid in the capsid protein corresponding to amino acid 687 of SEQ ID NO: 2 is R;

(d) the amino acid in the capsid protein corresponding to amino acid 346 of SEQ ID NO: 2 is A, and the amino acid in the capsid protein corresponding to amino acid 505 of SEQ ID NO: 2 is R; or (e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C, optionally wherein the capsid protein comprises the amino acid sequence of amino acids 138-736 of SEQ ID NO: 1, 2, 3, 4, 5, 6, 7, 9, 10, 11, 12, 13, 15, 16, or 17.

18. The method of claim 1, wherein the AAV Clade F capsid protein comprises an amino acid sequence having at least 95% sequence identity with the amino acid sequence of amino acids 1-736 of SEQ ID NO: 1, 2, 3, 4, 5, 6, 7, 8, 9, 10, 11, 12, 13, 15, 16, or 17, optionally wherein: the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G, optionally wherein:

(a) the amino acid in the capsid protein corresponding to amino acid 2 of SEQ ID NO: 2 is T, and the amino acid in the capsid protein corresponding to amino acid 312 of SEQ ID NO: 2 is Q;

(b) the amino acid in the capsid protein corresponding to amino acid 65 of SEQ ID NO: 2 is I, and the amino acid in the capsid protein corresponding to amino acid 626 of SEQ ID NO: 2 is Y;

(c) the amino acid in the capsid protein corresponding to amino acid 77 of SEQ ID NO: 2 is R, and the amino acid in the capsid protein corresponding to amino acid 690 of SEQ ID NO: 2 is K;

(d) the amino acid in the capsid protein corresponding to amino acid 119 of SEQ ID NO: 2 is L, and the amino acid in the capsid protein corresponding to amino acid 468 of SEQ ID NO: 2 is S;

(e) the amino acid in the capsid protein corresponding to amino acid 626 of SEQ ID NO: 2 is G, and the amino acid in the capsid protein corresponding to amino acid 718 of SEQ ID NO: 2 is G;

(f) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;

(g) the amino acid in the capsid protein corresponding to amino acid 505 of SEQ ID NO: 2 is R, and the amino acid in the capsid protein corresponding to amino acid 687 of SEQ ID NO: 2 is R;

(h) the amino acid in the capsid protein corresponding to amino acid 346 of SEQ ID NO: 2 is A, and the amino acid in the capsid protein corresponding to amino acid 505 of SEQ ID NO: 2 is R; or (i) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C, optionally wherein the capsid protein comprises the amino acid sequence of amino acids 1-736 of SEQ ID NO: 1, 2, 3, 4, 5, 6, 7, 8, 9, 10, 11, 12, 13, 15, 16, or 17.

* * * * *

SEQUENCE LISTING

```
<160> NUMBER OF SEQ ID NOS: 63

<210> SEQ ID NO 1
<211> LENGTH: 736
<212> TYPE: PRT
<213> ORGANISM: Artificial Sequence
<220> FEATURE:
<223> OTHER INFORMATION: adeno-associated AAV9

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60
```

-continued

```
Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
```

-continued

```
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 2
<211> LENGTH: 736
<212> TYPE: PRT
<213> ORGANISM: Artificial Sequence
<220> FEATURE:
<223> OTHER INFORMATION: novel AAV isolate

<400> SEQUENCE: 2

Met Thr Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
```

-continued

```
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Gln Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540
```

```
Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 3
<211> LENGTH: 736
<212> TYPE: PRT
<213> ORGANISM: Artificial Sequence
<220> FEATURE:
<223> OTHER INFORMATION: novel AAV isolate

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175
```

-continued

```
Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590
```

```
Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Gly Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Gly Gly Val
705                 710                 715                 720

Tyr Ser Glu Pro Arg Pro Ile Gly Thr Arg Tyr Leu Thr Arg Asn Leu
                725                 730                 735


<210> SEQ ID NO 4
<211> LENGTH: 736
<212> TYPE: PRT
<213> ORGANISM: Artificial Sequence
<220> FEATURE:
<223> OTHER INFORMATION: novel AAV isolate

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Ile Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220
```

-continued

```
Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Tyr Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
```

```
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 5
<211> LENGTH: 736
<212> TYPE: PRT
<213> ORGANISM: Artificial Sequence
<220> FEATURE:
<223> OTHER INFORMATION: novel AAV isolate

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Asp
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
```

-continued

```
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700
```

```
Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 6
<211> LENGTH: 736
<212> TYPE: PRT
<213> ORGANISM: Artificial Sequence
<220> FEATURE:
<223> OTHER INFORMATION: novel AAV isolate

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Leu Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335
```

-continued

```
Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Ser Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 7
<211> LENGTH: 736
```

-continued

<212> TYPE: PRT
<213> ORGANISM: Artificial Sequence
<220> FEATURE:
<223> OTHER INFORMATION: novel AAV isolate

<400> SEQUENCE: 7

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380
```

```
Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Arg Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 8
<211> LENGTH: 736
<212> TYPE: PRT
<213> ORGANISM: Artificial Sequence
<220> FEATURE:
<223> OTHER INFORMATION: novel AAV isolate

<400> SEQUENCE: 8

```
Met Ala Ala Asp Gly Tyr Leu Pro Asp Trp Leu Glu Asp Asn Leu Ser
1               5                   10                  15
```

-continued

```
Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Val Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
```

```
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 9
<211> LENGTH: 736
<212> TYPE: PRT
<213> ORGANISM: Artificial Sequence
<220> FEATURE:
<223> OTHER INFORMATION: novel AAV isolate

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
```

-continued

```
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Arg Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495
```

```
Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 10
<211> LENGTH: 736
<212> TYPE: PRT
<213> ORGANISM: Artificial Sequence
<220> FEATURE:
<223> OTHER INFORMATION: novel AAV isolate

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125
```

```
Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Cys Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540
```

-continued

```
Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 11
<211> LENGTH: 736
<212> TYPE: PRT
<213> ORGANISM: Artificial Sequence
<220> FEATURE:
<223> OTHER INFORMATION: novel AAV isolate

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Arg Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175
```

-continued

```
Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
```

```
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Lys Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 12
<211> LENGTH: 736
<212> TYPE: PRT
<213> ORGANISM: Artificial Sequence
<220> FEATURE:
<223> OTHER INFORMATION: novel AAV isolate

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
```

-continued

```
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro His Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Asn
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655
```

Asp Pro Pro Thr Ala Phe Asn Lys Asp Lys Leu Asn Ser Phe Ile Thr
660 665 670

Gln Tyr Ser Thr Gly Gln Val Ser Met Glu Ile Glu Trp Glu Leu Gln
675 680 685

Lys Glu Asn Ser Lys Arg Trp Asn Pro Glu Ile Gln Tyr Thr Ser Asn
690 695 700

Tyr Tyr Lys Ser Asn Asn Val Glu Phe Ala Val Asn Thr Glu Gly Val
705 710 715 720

Tyr Ser Glu Pro Arg Pro Ile Gly Thr Arg Tyr Leu Thr Arg Asn Leu
725 730 735

<210> SEQ ID NO 13
<211> LENGTH: 736
<212> TYPE: PRT
<213> ORGANISM: Artificial Sequence
<220> FEATURE:
<223> OTHER INFORMATION: novel AAV isolate

<400> SEQUENCE: 13

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Ala Arg Gly Leu Val Leu Pro
35 40 45

Gly Tyr Lys Tyr Leu Gly Pro Gly Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Glu Gln Ser Pro Gln Glu Pro Asp Ser Ser Ala Gly Ile Gly
145 150 155 160

Lys Ser Gly Ala Gln Pro Ala Lys Lys Arg Leu Asn Phe Gly Gln Thr
165 170 175

Gly Asp Thr Glu Ser Val Pro Asp Pro Gln Pro Ile Gly Glu Pro Pro
180 185 190

Ala Ala Pro Ser Gly Val Gly Ser Leu Thr Met Ala Ser Gly Gly Gly
195 200 205

Ala Pro Val Ala Asp Asn Asn Glu Gly Ala Asp Gly Val Gly Ser Ser
210 215 220

Ser Gly Asn Trp His Cys Asp Ser Gln Trp Leu Gly Asp Arg Val Ile
225 230 235 240

Thr Thr Ser Thr Arg Thr Trp Ala Leu Pro Thr Tyr Asn Asn His Leu
245 250 255

Tyr Lys Gln Ile Ser Asn Ser Thr Ser Gly Gly Ser Ser Asn Asp Asn
260 265 270

Ala Tyr Phe Gly Tyr Ser Thr Pro Trp Gly Tyr Phe Asp Phe Asn Arg
275 280 285

-continued

```
Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700
```

```
Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 14
<211> LENGTH: 736
<212> TYPE: PRT
<213> ORGANISM: Artificial Sequence
<220> FEATURE:
<223> OTHER INFORMATION: novel AAV isolate

<400> SEQUENCE: 14

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335
```

-continued

```
Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 15
<211> LENGTH: 736
<212> TYPE: PRT

<213> ORGANISM: Artificial Sequence
<220> FEATURE:
<223> OTHER INFORMATION: novel AAV isolate

<400> SEQUENCE: 15

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
```

```
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Arg Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 16
<211> LENGTH: 736
<212> TYPE: PRT
<213> ORGANISM: Artificial Sequence
<220> FEATURE:
<223> OTHER INFORMATION: novel AAV isolate

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
```

-continued

```
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Ala Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445
```

```
Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 17
<211> LENGTH: 736
<212> TYPE: PRT
<213> ORGANISM: Artificial Sequence
<220> FEATURE:
<223> OTHER INFORMATION: novel AAV isolate

<400> SEQUENCE: 17

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80
```

-continued

```
Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495
```

```
Asn Asn Ser Glu Ile Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Cys Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

```
<210> SEQ ID NO 18
<211> LENGTH: 145
<212> TYPE: DNA
<213> ORGANISM: Artificial Sequence
<220> FEATURE:
<223> OTHER INFORMATION: AAV2 5' ITR

<400> SEQUENCE: 18

ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcct                                          145


<210> SEQ ID NO 19
<211> LENGTH: 145
<212> TYPE: DNA
<213> ORGANISM: Artificial Sequence
<220> FEATURE:
<223> OTHER INFORMATION: AAV2 3' ITR

<400> SEQUENCE: 19

aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag agagggagtg gccaa                                          145


<210> SEQ ID NO 20
```

<211> LENGTH: 167
<212> TYPE: DNA
<213> ORGANISM: Artificial Sequence
<220> FEATURE:
<223> OTHER INFORMATION: AAV5 5' ITR

<400> SEQUENCE: 20
ctctcccccc tgtcgcgttc gctcgctcgc tggctcgttt ggggggtgg cagctcaaag 60 agctgccaga cgacggccct ctggccgtcg cccccccaaa cgagccagcg agcgagcgaa 120
cgcgacaggg gggagagtgc cacactctca agcaaggggg ttttgta 167

<210> SEQ ID NO 21
<211> LENGTH: 167
<212> TYPE: DNA
<213> ORGANISM: Artificial Sequence
<220> FEATURE:
<223> OTHER INFORMATION: AAV5 3' ITR

<400> SEQUENCE: 21
tacaaaacct ccttgcttga gagtgtggca ctctcccccc tgtcgcgttc gctcgctcgc 60
tggctcgttt ggggggtgg cagctcaaag agctgccaga cgacggccct ctggccgtcg 120
cccccccaaa cgagccagcg agcgagcgaa cgcgacaggg gggagag 167

<210> SEQ ID NO 22
<211> LENGTH: 621
<212> TYPE: PRT
<213> ORGANISM: Artificial Sequence
<220> FEATURE:
<223> OTHER INFORMATION: AAV2 Rep

<400> SEQUENCE: 22

Met Pro Gly Phe Tyr Glu Ile Val Ile Lys Val Pro Ser Asp Leu Asp
1 5 10 15

Glu His Leu Pro Gly Ile Ser Asp Ser Phe Val Asn Trp Val Ala Glu
20 25 30

Lys Glu Trp Glu Leu Pro Pro Asp Ser Asp Met Asp Leu Asn Leu Ile
35 40 45

Glu Gln Ala Pro Leu Thr Val Ala Glu Lys Leu Gln Arg Asp Phe Leu
50 55 60

Thr Glu Trp Arg Arg Val Ser Lys Ala Pro Glu Ala Leu Phe Phe Val
65 70 75 80

Gln Phe Glu Lys Gly Glu Ser Tyr Phe His Met His Val Leu Val Glu
85 90 95

Thr Thr Gly Val Lys Ser Met Val Leu Gly Arg Phe Leu Ser Gln Ile
100 105 110

Arg Glu Lys Leu Ile Gln Arg Ile Tyr Arg Gly Ile Glu Pro Thr Leu
115 120 125

Pro Asn Trp Phe Ala Val Thr Lys Thr Arg Asn Gly Ala Gly Gly Gly
130 135 140

Asn Lys Val Val Asp Glu Cys Tyr Ile Pro Asn Tyr Leu Leu Pro Lys
145 150 155 160

Thr Gln Pro Glu Leu Gln Trp Ala Trp Thr Asn Met Glu Gln Tyr Leu
165 170 175

Ser Ala Cys Leu Asn Leu Thr Glu Arg Lys Arg Leu Val Ala Gln His
180 185 190

Leu Thr His Val Ser Gln Thr Gln Glu Gln Asn Lys Glu Asn Gln Asn
195 200 205

-continued

```
Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
    530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
    610                 615                 620
```

-continued

<210> SEQ ID NO 23
<211> LENGTH: 198
<212> TYPE: DNA
<213> ORGANISM: Artificial Sequence
<220> FEATURE:
<223> OTHER INFORMATION: SV40 polyadenylation sequence

<400> SEQUENCE: 23
gatccagaca tgataagata cattgatgag tttggacaaa ccacaactag aatgcagtga 60
aaaaaatgct ttatttgtga aatttgtgat gctattgctt tatttgtaac cattataagc 120
tgcaataaac aagttaacaa caacaattgc attcatttta tgtttcaggt tcagggggag 180
gtgtgggagg ttttttaa 198

<210> SEQ ID NO 24
<211> LENGTH: 26
<212> TYPE: DNA
<213> ORGANISM: Artificial Sequence
<220> FEATURE:
<223> OTHER INFORMATION: splice acceptor

<400> SEQUENCE: 24
ctgacctctt ctcttcctcc cacagg 26

<210> SEQ ID NO 25
<211> LENGTH: 209
<212> TYPE: PRT
<213> ORGANISM: Homo sapiens

<400> SEQUENCE: 25

Met Val Phe Phe Gly Asn Val Asp Ser Ser Gly Ile Lys His Asn Ile
1 5 10 15

Phe Asn Pro Pro Ile Ile Ala Arg Tyr Ile Arg Leu His Pro Thr His
20 25 30

Tyr Ser Ile Arg Ser Thr Leu Arg Met Glu Leu Met Gly Cys Asp Leu
35 40 45

Asn Ser Cys Ser Met Pro Leu Gly Met Glu Ser Lys Ala Ile Ser Asp
50 55 60

Ala Gln Ile Thr Ala Ser Ser Tyr Phe Thr Asn Met Phe Ala Thr Trp
65 70 75 80

Ser Pro Ser Lys Ala Arg Leu His Leu Gln Gly Arg Ser Asn Ala Trp
85 90 95

Arg Pro Gln Val Asn Asn Pro Lys Glu Trp Leu Gln Val Asp Phe Gln
100 105 110

Lys Thr Met Lys Val Thr Gly Val Thr Thr Gln Gly Val Lys Ser Leu
115 120 125

Leu Thr Ser Met Tyr Val Lys Glu Phe Leu Ile Ser Ser Ser Gln Asp
130 135 140

Gly His Gln Trp Thr Leu Phe Phe Gln Asn Gly Lys Val Lys Val Phe
145 150 155 160

Gln Gly Asn Gln Asp Ser Phe Thr Pro Val Val Asn Ser Leu Asp Pro
165 170 175

Pro Leu Leu Thr Arg Tyr Leu Arg Ile His Pro Gln Ser Trp Val His
180 185 190

Gln Ile Ala Leu Arg Met Glu Val Leu Gly Cys Glu Ala Gln Asp Leu
195 200 205

Tyr

<210> SEQ ID NO 26
<211> LENGTH: 627
<212> TYPE: DNA
<213> ORGANISM: Homo sapiens

<400> SEQUENCE: 26
gtcttctttg gcaatgtgga ttcatctggg ataaaacaca atatttttaa ccctccaatt 60
attgctcgat acatccgttt gcacccaact cattatagca ttcgcagcac tcttcgcatg 120
gagttgatgg gctgtgattt aaatagttgc agcatgccat tgggaatgga gagtaaagca 180
atatcagatg cacagattac tgcttcatcc tactttacca atatgtttgc cacctggtct 240
ccttcaaaag ctcgacttca cctccaaggg aggagtaatg cctggagacc tcaggtgaat 300
aatccaaaag agtggctgca agtggacttc cagaagacaa tgaaagtcac aggagtaact 360
actcagggag taaaatctct gcttaccagc atgtatgtga aggagttcct catctccagc 420
agtcaagatg gccatcagtg gactctcttt tttcagaatg gcaaagtaaa ggtttttcag 480
ggaaatcaag actccttcac acctgtggtg aactctctag acccaccgtt actgactcgc 540
taccttcgaa ttcaccccca gagttgggtg caccagattg ccctgaggat ggaggttctg 600
ggctgcgagg cacaggacct ctactga 627

<210> SEQ ID NO 27
<211> LENGTH: 800
<212> TYPE: DNA
<213> ORGANISM: Homo sapiens

<400> SEQUENCE: 27
agtctaataa ggaaagcaga aaagcaaagc aaccttataa tatggtgcaa taatttgcta 60
taatgaagtt atatacaaag tgaagtagaa gcatagaaga agcagcacta aatttgtctg 120
ggtgagtcag agaaggctaa ccaggaaaaa tagtttctga actaacactt gaaggaggtg 180
tagcagttca tcactgacag tgatgttggg gtgggtctgg tttcaggaga ggggaggaaa 240
ttggctttgg tctgaggctg aggtgtgggc aaagcattag cttatgtggg tccattagct 300
tatgtgagtc cacaaaaggt gtgtgtgtgt ttgtgtgtat gtgtgtgtgt gtgtgtgtgt 360
gtgtgtgtgt acgaaatggg ggctcaatga tttggtagtg gtttggtttg tcaagaagca 420
ggctgggaac tcaataagca tctttccatt catttctact gtgtatccca cagcttcaca 480
cacacatgca catttcaaca ttggtgactg cttcacttgc acacctaagg taatgatgga 540
cacacctgta gcaatgtaga ttcttcctaa gctaataatt agtttcagga ggtagcacat 600
acatttaaaa ataggttaaa ataaagtgtt attttaattg gtaggtggat ctgttggcac 660
caatgattat tcacggcatc aagacccagg gtgcccgtca gaagttctcc agcctctaca 720
tctctcagtt tatcatcatg tatagtcttg atgggaagaa gtggcagact tatcgaggaa 780
attccactgg aaccttaatg 800

<210> SEQ ID NO 28
<211> LENGTH: 800
<212> TYPE: DNA
<213> ORGANISM: Homo sapiens

<400> SEQUENCE: 28
gtatgtaatt agtcatttaa agggaatgcc tgaatacttt aaagaatttt ggcagatttc 60
agatattgga caaacactct tagcttccac aaacttaatt ccaaaaaata atttttcact 120
tatgagcaat agagttatta cggacatatc agcaaaaatg tagtagtgtc aaggctcata 180

-continued

```
gatgatagaa atgaagagat gctgtattga tagaaatatg tgattcagga ctgtgtggat    240

tgatgattgt gagcttgctt atggatatcc taggtttgag gttatagtag gacaatcagg    300

ttgaaatgtc cagcaggcag taggtgaaag acaagtttag ggggcaaaac catggatgga    360

gatgaagatt catgacttcc acataaaagg atgggtgaaa ctttgggaat tgatgaattc    420

tctagaggtg agctcaagac ccttaaaggc ttaaaacctc agcgttattg tctactcttc    480

cctcattttt atgcccacaa atctggtcaa tcctttattt gcaatgcctc tcacatctct    540

ttcttctgtt tccatttata ccgctgttgc cacagcccag ggtcccatca cctcacactt    600

gatctattgt attacattcc taactagtct tcccccgttt ctaatctgtt ctccgataaa    660

agctgcacat cattttcagg ataatcatca gtcgcctgcc taaaactttt caatgtcttc    720

ccattgtctt tagaataaag ttcaaagtct tcaaatgacc ccaagcaaga taacttttgt    780

ttgccccttt agatccattt                                                800
```

<210> SEQ ID NO 29
<211> LENGTH: 800
<212> TYPE: DNA
<213> ORGANISM: Homo sapiens

<400> SEQUENCE: 29

```
agcagcacta aatttgtctg ggtgagtcag agaaggctaa ccaggaaaaa tagtttctga     60

actaacactt gaaggaggtg tagcagttca tcactgacag tgatgttggg gtgggtctgg    120

tttcaggaga ggggaggaaa ttggctttgg tctgaggctg aggtgtgggc aaagcattag    180

cttatgtggg tccattagct tatgtgagtc cacaaaaggt gtgtgtgtgt ttgtgtgtat    240

gtgtgtgtgt gtgtgtgtgt gtgtgtgtgt acgaaatggg ggctcaatga tttggtagtg    300

gtttggtttg tcaagaagca ggctgggaac tcaataagca tctttccatt catttctact    360

gtgtatccca cagcttcaca cacacatgca catttcaaca ttggtgactg cttcacttgc    420

acacctaagg taatgatgga cacacctgta gcaatgtaga ttcttcctaa gctaataatt    480

agtttcagga ggtagcacat acatttaaaa ataggttaaa ataaagtgtt attttaattg    540

gtaggtggat ctgttggcac caatgattat tcacggcatc aagacccagg gtgcccgtca    600

gaagttctcc agcctctaca tctctcagtt tatcatcatg tatagtcttg atgggaagaa    660

gtggcagact tatcgaggaa attccactgg aaccttaatg gtatgtaatt agtcatttaa    720

agggaatgcc tgaatacttt aaagaatttt ggcagatttc agatattgga caaacactct    780

tagcttccac aaacttaatt                                                800
```

<210> SEQ ID NO 30
<211> LENGTH: 800
<212> TYPE: DNA
<213> ORGANISM: Homo sapiens

<400> SEQUENCE: 30

```
ccaaaaaata atttttcact tatgagcaat agagttatta cggacatatc agcaaaaatg     60

tagtagtgtc aaggctcata gatgatagaa atgaagagat gctgtattga tagaaatatg    120

tgattcagga ctgtgtggat tgatgattgt gagcttgctt atggatatcc taggtttgag    180

gttatagtag gacaatcagg ttgaaatgtc cagcaggcag taggtgaaag acaagtttag    240

ggggcaaaac catggatgga gatgaagatt catgacttcc acataaaagg atgggtgaaa    300

ctttgggaat tgatgaattc tctagaggtg agctcaagac ccttaaaggc ttaaaacctc    360

agcgttattg tctactcttc cctcattttt atgcccacaa atctggtcaa tcctttattt    420
```

gcaatgcctc tcacatctct ttcttctgtt tccatttata ccgctgttgc cacagcccag 480
ggtcccatca cctcacactt gatctattgt attacattcc taactagtct tcccccgttt 540
ctaatctgtt ctccgataaa agctgcacat cattttcagg ataatcatca gtcgcctgcc 600
taaaactttt caatgtcttc ccattgtctt tagaataaag ttcaaagtct tcaaatgacc 660
ccaagcaaga taacttttgt ttgccccttt agatccattt tcctgcttct ctaccctgct 720
tcttgttctg tgaggtgagc ttgtatagaa tacatcaaca ggttaccttg tcctccagct 780
tttggttgga tttcaccaac 800

<210> SEQ ID NO 31
<211> LENGTH: 565
<212> TYPE: DNA
<213> ORGANISM: Homo sapiens

<400> SEQUENCE: 31
ggaaattggc tttggtctga ggctgaggtg tgggcaaagc attagcttat gtgggtccat 60
tagcttatgt gagtccacaa aaggtgtgtg tgtgtttgtg tgtatgtgtg tgtgtgtgtg 120
tgtgtgtgtg tgtgtacgaa atgggggctc aatgatttgg tagtggtttg gtttgtcaag 180
aagcaggctg ggaactcaat aagcatcttt ccattcattt ctactgtgta tcccacagct 240
tcacacacac atgcacattt caacattggt gactgcttca cttgcacacc taaggtaatg 300
atggacacac ctgtagcaat gtagattctt cctaagctaa taattagttt caggaggtag 360
cacatacatt taaaaatagg ttaaaataaa gtgttatttt aattggtagg tggatctgtt 420
ggcaccaatg attattcacg gcatcaagac ccagggtgcc cgtcagaagt tctccagcct 480
ctacatctct cagtttatca tcatgtatag tcttgatggg aagaagtggc agacttatcg 540
aggaaattcc actggaacct taatg 565

<210> SEQ ID NO 32
<211> LENGTH: 241
<212> TYPE: DNA
<213> ORGANISM: Homo sapiens

<400> SEQUENCE: 32
gtatgtaatt agtcatttaa agggaatgcc tgaatacttt aaagaatttt ggcagatttc 60
agatattgga caaacactct tagcttccac aaacttaatt ccaaaaaata atttttcact 120
tatgagcaat agagttatta cggacatatc agcaaaaatg tagtagtgtc aaggctcata 180
gatgatagaa atgaagagat gctgtattga tagaaatatg tgattcagga ctgtgtggat 240
t 241

<210> SEQ ID NO 33
<211> LENGTH: 1447
<212> TYPE: DNA
<213> ORGANISM: Artificial Sequence
<220> FEATURE:
<223> OTHER INFORMATION: pHMI-hF8-004-F8 coding sequence cassette
(including FVIII partial coding sequence and SV40 polyA)

<400> SEQUENCE: 33
ggaaattggc tttggtctga ggctgaggtg tgggcaaagc attagcttat gtgggtccat 60
tagcttatgt gagtccacaa aaggtgtgtg tgtgtttgtg tgtatgtgtg tgtgtgtgtg 120
tgtgtgtgtg tgtgtacgaa atgggggctc aatgatttgg tagtggtttg gtttgtcaag 180
aagcaggctg ggaactcaat aagcatcttt ccattcattt ctactgtgta tcccacagct 240

```
tcacacacac atgcacattt caacattggt gactgcttca cttgcacacc taaggtaatg    300
atggacacac ctgtagcaat gtagattctt cctaagctaa taattagttt caggaggtag    360
cacatacatt taaaaatagg ttaaaataaa gtgttatttt aattggtagg tggatctgtt    420
ggcaccaatg attattcacg gcatcaagac ccagggtgcc cgtcagaagt tctccagcct    480
ctacatctct cagtttatca tcatgtatag tcttgatggg aagaagtggc agacttatcg    540
aggaaattcc actggaacct taatggtctt ctttggcaat gtggattcat ctgggataaa    600
acacaatatt tttaaccctc caattattgc tcgatacatc cgtttgcacc caactcatta    660
tagcattcgc agcactcttc gcatggagtt gatgggctgt gatttaaata gttgcagcat    720
gccattggga atggagagta aagcaatatc agatgcacag attactgctt catcctactt    780
taccaatatg tttgccacct ggtctccttc aaaagctcga cttcacctcc aagggaggag    840
taatgcctgg agacctcagg tgaataatcc aaaagagtgg ctgcaagtgg acttccagaa    900
gacaatgaaa gtcacaggag taactactca gggagtaaaa tctctgctta ccagcatgta    960
tgtgaaggag ttcctcatct ccagcagtca agatggccat cagtggactc tctttttca    1020
gaatggcaaa gtaaaggttt ttcagggaaa tcaagactcc ttcacacctg tggtgaactc   1080
tctagaccca ccgttactga ctcgctacct tcgaattcac ccccagagtt gggtgcacca   1140
gattgccctg aggatggagg ttctgggctg cgaggcacag gacctctact gaaagcttta   1200
ccaaggcctc tcgagcctct agaactatag tgagtcgtat tacgtagatc cagacatgat   1260
aagatacatt gatgagtttg gacaaaccac aactagaatg cagtgaaaaa aatgctttat   1320
ttgtgaaatt tgtgatgcta ttgctttatt tgtaaccatt ataagctgca ataaacaagt   1380
taacaacaac aattgcattc attttatgtt tcaggttcag ggggaggtgt gggaggtttt   1440
ttaagct                                                             1447
```

<210> SEQ ID NO 34
<211> LENGTH: 806
<212> TYPE: DNA
<213> ORGANISM: Homo sapiens

<400> SEQUENCE: 34

```
ggaaattggc tttggtctga ggctgaggtg tgggcaaagc attagcttat gtgggtccat     60
tagcttatgt gagtccacaa aaggtgtgtg tgtgtttgtg tgtatgtgtg tgtgtgtgtg    120
tgtgtgtgtg tgtgtacgaa atgggggctc aatgatttgg tagtggtttg gtttgtcaag    180
aagcaggctg ggaactcaat aagcatcttt ccattcattt ctactgtgta tcccacagct    240
tcacacacac atgcacattt caacattggt gactgcttca cttgcacacc taaggtaatg    300
atggacacac ctgtagcaat gtagattctt cctaagctaa taattagttt caggaggtag    360
cacatacatt taaaaatagg ttaaaataaa gtgttatttt aattggtagg tggatctgtt    420
ggcaccaatg attattcacg gcatcaagac ccagggtgcc cgtcagaagt tctccagcct    480
ctacatctct cagtttatca tcatgtatag tcttgatggg aagaagtggc agacttatcg    540
aggaaattcc actggaacct taatggtatg taattagtca tttaaaggga atgcctgaat    600
actttaaaga attttggcag atttcagata ttggacaaac actcttagct tccacaaact    660
taattccaaa aaataatttt tcacttatga gcaatagagt tattacggac atatcagcaa    720
aaatgtagta gtgtcaaggc tcatagatga tagaaatgaa gagatgctgt attgatagaa    780
atatgtgatt caggactgtg tggatt                                         806
```

<210> SEQ ID NO 35
<211> LENGTH: 246
<212> TYPE: DNA
<213> ORGANISM: Artificial Sequence
<220> FEATURE:
<223> OTHER INFORMATION: SV40 polyadenylation sequence

<400> SEQUENCE: 35
caaggcctct cgagcctcta gaactatagt gagtcgtatt acgtagatcc agacatgata 60
agatacattg atgagtttgg acaaaccaca actagaatgc agtgaaaaaa atgctttatt 120
tgtgaaattt gtgatgctat tgctttattt gtaaccatta taagctgcaa taaacaagtt 180
aacaacaaca attgcattca ttttatgttt caggttcagg gggaggtgtg ggaggttttt 240
taagct 246

<210> SEQ ID NO 36
<211> LENGTH: 198
<212> TYPE: DNA
<213> ORGANISM: Artificial Sequence
<220> FEATURE:
<223> OTHER INFORMATION: SV40 polyadenylation sequence

<400> SEQUENCE: 36
ttaaaaaacc tcccacacct ccccctgaac ctgaaacata aaatgaatgc aattgttgtt 60
gttaacttgt ttattgcagc ttataatggt tacaaataaa gcaatagcat cacaaatttc 120
acaaataaag catttttttc actgcattct agttgtggtt tgtccaaact catcaatgta 180
tcttatcatg tctggatc 198

<210> SEQ ID NO 37
<211> LENGTH: 246
<212> TYPE: DNA
<213> ORGANISM: Artificial Sequence
<220> FEATURE:
<223> OTHER INFORMATION: SV40 polyadenylation sequence

<400> SEQUENCE: 37
agcttaaaaa acctcccaca cctccccctg aacctgaaac ataaaatgaa tgcaattgtt 60
gttgttaact tgtttattgc agcttataat ggttacaaat aaagcaatag catcacaaat 120
ttcacaaata aagcattttt ttcactgcat tctagttgtg gtttgtccaa actcatcaat 180
gtatcttatc atgtctggat ctacgtaata cgactcacta tagttctaga ggctcgagag 240
gccttg 246

<210> SEQ ID NO 38
<211> LENGTH: 2236
<212> TYPE: DNA
<213> ORGANISM: Artificial Sequence
<220> FEATURE:
<223> OTHER INFORMATION: pHMI-hF8-001-F8 correction genome

<400> SEQUENCE: 38
agtctaataa ggaaagcaga aaagcaaagc aaccttataa tatggtgcaa taatttgcta 60
taatgaagtt atatacaaag tgaagtagaa gcatagaaga agcagcacta aatttgtctg 120
ggtgagtcag agaaggctaa ccaggaaaaa tagtttctga actaacactt gaaggaggtg 180
tagcagttca tcactgacag tgatgttggg gtgggtctgg tttcaggaga ggggaggaaa 240
ttggctttgg tctgaggctg aggtgtgggc aaagcattag cttatgtggg tccattagct 300
tatgtgagtc cacaaaaggt gtgtgtgtgt ttgtgtgtat gtgtgtgtgt gtgtgtgtgt 360
gtgtgtgtgt acgaaatggg ggctcaatga tttggtagtg gtttggtttg tcaagaagca 420
ggctgggaac tcaataagca tctttccatt catttctact gtgtatccca cagcttcaca 480
cacacatgca catttcaaca ttggtgactg cttcacttgc acacctaagg taatgatgga 540
cacacctgta gcaatgtaga ttcttcctaa gctaataatt agtttcagga ggtagcacat 600
acatttaaaa ataggttaaa ataaagtgtt attttaattg gtaggtggat ctgttggcac 660
caatgattat tcacggcatc aagacccagg gtgcccgtca gaagttctcc agcctctaca 720
tctctcagtt tatcatcatg tatagtcttg atgggaagaa gtggcagact tatcgaggaa 780
attccactgg aaccttaatg gtcttctttg gcaatgtgga ttcatctggg ataaaacaca 840
atatttttaa ccctccaatt attgctcgat acatccgttt gcacccaact cattatagca 900
ttcgcagcac tcttcgcatg gagttgatgg gctgtgattt aaatagttgc agcatgccat 960
tgggaatgga gagtaaagca atatcagatg cacagattac tgcttcatcc tactttacca 1020
atatgtttgc cacctggtct ccttcaaaag ctcgacttca cctccaaggg aggagtaatg 1080
cctggagacc tcaggtgaat aatccaaaag agtggctgca agtggacttc cagaagacaa 1140
tgaaagtcac aggagtaact actcagggag taaaatctct gcttaccagc atgtatgtga 1200
aggagttcct catctccagc agtcaagatg gccatcagtg gactctcttt tttcagaatg 1260
gcaaagtaaa ggtttttcag ggaaatcaag actccttcac acctgtggtg aactctctag 1320
acccaccgtt actgactcgc taccttcgaa ttcacccccca gagttgggtg caccagattg 1380
ccctgaggat ggaggttctg ggctgcgagg cacaggacct ctactgaaag ctttacgtat 1440
gtaattagtc atttaaaggg aatgcctgaa tactttaaag aattttggca gatttcagat 1500
attggacaaa cactcttagc ttccacaaac ttaattccaa aaaataattt ttcacttatg 1560
agcaatagag ttattacgga catatcagca aaaatgtagt agtgtcaagg ctcatagatg 1620
atagaaatga agagatgctg tattgataga aatatgtgat tcaggactgt gtggattgat 1680
gattgtgagc ttgcttatgg atatcctagg tttgaggtta tagtaggaca atcaggttga 1740
aatgtccagc aggcagtagg tgaaagacaa gtttaggggg caaaaccatg gatggagatg 1800
aagattcatg acttccacat aaaaggatgg gtgaaacttt gggaattgat gaattctcta 1860
gaggtgagct caagaccctt aaaggcttaa aacctcagcg ttattgtcta ctcttccctc 1920
atttttatgc ccacaaatct ggtcaatcct ttatttgcaa tgcctctcac atctctttct 1980
tctgtttcca tttataccgc tgttgccaca gcccagggtc ccatcacctc acacttgatc 2040
tattgtatta cattcctaac tagtcttccc ccgtttctaa tctgttctcc gataaaagct 2100
gcacatcatt ttcaggataa tcatcagtcg cctgcctaaa acttttcaat gtcttcccat 2160
tgtctttaga ataaagttca aagtcttcaa atgaccccaa gcaagataac ttttgtttgc 2220
ccctttagat ccattt 2236

<210> SEQ ID NO 39
<211> LENGTH: 2482
<212> TYPE: DNA
<213> ORGANISM: Artificial Sequence
<220> FEATURE:
<223> OTHER INFORMATION: pHMI-hF8-002-F8 correction genome

<400> SEQUENCE: 39
agtctaataa ggaaagcaga aaagcaaagc aaccttataa tatggtgcaa taatttgcta 60
taatgaagtt atatacaaag tgaagtagaa gcatagaaga agcagcacta aatttgtctg 120

-continued

```
ggtgagtcag agaaggctaa ccaggaaaaa tagtttctga actaacactt gaaggaggtg    180
tagcagttca tcactgacag tgatgttggg gtgggtctgg tttcaggaga ggggaggaaa    240
ttggctttgg tctgaggctg aggtgtgggc aaagcattag cttatgtggg tccattagct    300
tatgtgagtc cacaaaaggt gtgtgtgtgt ttgtgtgtat gtgtgtgtgt gtgtgtgtgt    360
gtgtgtgtgt acgaaatggg ggctcaatga tttggtagtg gtttggtttg tcaagaagca    420
ggctgggaac tcaataagca tctttccatt catttctact gtgtatccca cagcttcaca    480
cacacatgca catttcaaca ttggtgactg cttcacttgc acacctaagg taatgatgga    540
cacacctgta gcaatgtaga ttcttcctaa gctaataatt agtttcagga ggtagcacat    600
acatttaaaa ataggttaaa ataaagtgtt attttaattg gtaggtggat ctgttggcac    660
caatgattat tcacggcatc aagacccagg gtgcccgtca gaagttctcc agcctctaca    720
tctctcagtt tatcatcatg tatagtcttg atgggaagaa gtggcagact tatcgaggaa    780
attccactgg aaccttaatg gtcttctttg gcaatgtgga ttcatctggg ataaaacaca    840
atatttttaa ccctccaatt attgctcgat acatccgttt gcacccaact cattatagca    900
ttcgcagcac tcttcgcatg gagttgatgg gctgtgattt aaatagttgc agcatgccat    960
tgggaatgga gagtaaagca atatcagatg cacagattac tgcttcatcc tactttacca   1020
atatgtttgc cacctggtct ccttcaaaag ctcgacttca cctccaaggg aggagtaatg   1080
cctggagacc tcaggtgaat aatccaaaag agtggctgca agtggacttc cagaagacaa   1140
tgaaagtcac aggagtaact actcagggag taaaatctct gcttaccagc atgtatgtga   1200
aggagttcct catctccagc agtcaagatg gccatcagtg gactctcttt tttcagaatg   1260
gcaaagtaaa ggtttttcag ggaaatcaag actccttcac acctgtggtg aactctctag   1320
acccaccgtt actgactcgc taccttcgaa ttcacccccca gagttgggtg caccagattg   1380
ccctgaggat ggaggttctg ggctgcgagg cacaggacct ctactgaaag ctttaccaag   1440
gcctctcgag cctctagaac tatagtgagt cgtattacgt agatccagac atgataagat   1500
acattgatga gtttggacaa accacaacta gaatgcagtg aaaaaaatgc tttatttgtg   1560
aaatttgtga tgctattgct ttatttgtaa ccattataag ctgcaataaa caagttaaca   1620
acaacaattg cattcatttt atgtttcagg ttcaggggga ggtgtgggag gtttttttaag   1680
ctgtatgtaa ttagtcattt aaagggaatg cctgaatact ttaaagaatt ttggcagatt   1740
tcagatattg gacaaacact cttagcttcc acaaacttaa ttccaaaaaa taatttttca   1800
cttatgagca atagagttat tacggacata tcagcaaaaa tgtagtagtg tcaaggctca   1860
tagatgatag aaatgaagag atgctgtatt gatagaaata tgtgattcag gactgtgtgg   1920
attgatgatt gtgagcttgc ttatggatat cctaggtttg aggttatagt aggacaatca   1980
ggttgaaatg tccagcaggc agtaggtgaa agacaagttt agggggcaaa accatggatg   2040
gagatgaaga ttcatgactt ccacataaaa ggatgggtga aactttggga attgatgaat   2100
tctctagagg tgagctcaag acccttaaag gcttaaaacc tcagcgttat tgtctactct   2160
tccctcattt ttatgcccac aaatctggtc aatcctttat ttgcaatgcc tctcacatct   2220
ctttcttctg tttccattta taccgctgtt gccacagccc agggtcccat cacctcacac   2280
ttgatctatt gtattacatt cctaactagt cttcccccgt ttctaatctg ttctccgata   2340
aaagctgcac atcattttca ggataatcat cagtcgcctg cctaaaactt ttcaatgtct   2400
tcccattgtc tttagaataa agttcaaagt cttcaaatga ccccaagcaa gataactttt   2460
gtttgcccct ttagatccat tt                                            2482
```

<210> SEQ ID NO 40
<211> LENGTH: 1442
<212> TYPE: DNA
<213> ORGANISM: Artificial Sequence
<220> FEATURE:
<223> OTHER INFORMATION: pHMI-hF8-003-F8 correction genome

<400> SEQUENCE: 40
ggaaattggc tttggtctga ggctgaggtg tgggcaaagc attagcttat gtgggtccat 60
tagcttatgt gagtccacaa aaggtgtgtg tgtgtttgtg tgtatgtgtg tgtgtgtgtg 120
tgtgtgtgtg tgtgtacgaa atgggggctc aatgatttgg tagtggtttg gtttgtcaag 180
aagcaggctg ggaactcaat aagcatcttt ccattcattt ctactgtgta tcccacagct 240
tcacacacac atgcacattt caacattggt gactgcttca cttgcacacc taaggtaatg 300
atggacacac ctgtagcaat gtagattctt cctaagctaa taattagttt caggaggtag 360
cacatacatt taaaaatagg ttaaaataaa gtgttatttt aattggtagg tggatctgtt 420
ggcaccaatg attattcacg gcatcaagac ccagggtgcc cgtcagaagt tctccagcct 480
ctacatctct cagtttatca tcatgtatag tcttgatggg aagaagtggc agacttatcg 540
aggaaattcc actggaacct taatggtctt ctttggcaat gtggattcat ctgggataaa 600
acacaatatt tttaaccctc caattattgc tcgatacatc cgtttgcacc caactcatta 660
tagcattcgc agcactcttc gcatggagtt gatgggctgt gatttaaata gttgcagcat 720
gccattggga atggagagta aagcaatatc agatgcacag attactgctt catcctactt 780
taccaatatg tttgccacct ggtctccttc aaaagctcga cttcacctcc aagggaggag 840
taatgcctgg agacctcagg tgaataatcc aaaagagtgg ctgcaagtgg acttccagaa 900
gacaatgaaa gtcacaggag taactactca gggagtaaaa tctctgctta ccagcatgta 960
tgtgaaggag ttcctcatct ccagcagtca agatggccat cagtggactc tctttttca 1020 gaatggcaaa gtaaaggttt ttcagggaaa tcaagactcc ttcacacctg tggtgaactc 1080
tctagaccca ccgttactga ctcgctacct tcgaattcac ccccagagtt gggtgcacca 1140
gattgccctg aggatggagg ttctgggctg cgaggcacag gacctctact gaaagcttta 1200
cgtatgtaat tagtcattta aagggaatgc ctgaatactt taaagaattt tggcagattt 1260
cagatattgg acaaacactc ttagcttcca caaacttaat tccaaaaaat aatttttcac 1320
ttatgagcaa tagagttatt acggacatat cagcaaaaat gtagtagtgt caaggctcat 1380
agatgataga aatgaagaga tgctgtattg atagaaatat gtgattcagg actgtgtgga 1440
tt 1442

<210> SEQ ID NO 41
<211> LENGTH: 1688
<212> TYPE: DNA
<213> ORGANISM: Artificial Sequence
<220> FEATURE:
<223> OTHER INFORMATION: pHMI-hF8-004-F8 correction genome

<400> SEQUENCE: 41
ggaaattggc tttggtctga ggctgaggtg tgggcaaagc attagcttat gtgggtccat 60
tagcttatgt gagtccacaa aaggtgtgtg tgtgtttgtg tgtatgtgtg tgtgtgtgtg 120
tgtgtgtgtg tgtgtacgaa atgggggctc aatgatttgg tagtggtttg gtttgtcaag 180
aagcaggctg ggaactcaat aagcatcttt ccattcattt ctactgtgta tcccacagct 240

-continued

```
tcacacacac atgcacattt caacattggt gactgcttca cttgcacacc taaggtaatg    300

atggacacac ctgtagcaat gtagattctt cctaagctaa taattagttt caggaggtag    360

cacatacatt taaaaatagg ttaaaataaa gtgttatttt aattggtagg tggatctgtt    420

ggcaccaatg attattcacg gcatcaagac ccagggtgcc cgtcagaagt tctccagcct    480

ctacatctct cagtttatca tcatgtatag tcttgatggg aagaagtggc agacttatcg    540

aggaaattcc actggaacct taatggtctt ctttggcaat gtggattcat ctgggataaa    600

acacaatatt tttaaccctc caattattgc tcgatacatc cgtttgcacc caactcatta    660

tagcattcgc agcactcttc gcatggagtt gatgggctgt gatttaaata gttgcagcat    720

gccattggga atggagagta aagcaatatc agatgcacag attactgctt catcctactt    780

taccaatatg tttgccacct ggtctccttc aaaagctcga cttcacctcc aagggaggag    840

taatgcctgg agacctcagg tgaataatcc aaaagagtgg ctgcaagtgg acttccagaa    900

gacaatgaaa gtcacaggag taactactca gggagtaaaa tctctgctta ccagcatgta    960

tgtgaaggag ttcctcatct ccagcagtca agatggccat cagtggactc tcttttttca   1020

gaatggcaaa gtaaaggttt ttcagggaaa tcaagactcc ttcacacctg tggtgaactc   1080

tctagaccca ccgttactga ctcgctacct tcgaattcac ccccagagtt gggtgcacca   1140

gattgccctg aggatggagg ttctgggctg cgaggcacag gacctctact gaaagcttta   1200

ccaaggcctc tcgagcctct agaactatag tgagtcgtat tacgtagatc cagacatgat   1260

aagatacatt gatgagtttg gacaaaccac aactagaatg cagtgaaaaa aatgctttat   1320

ttgtgaaatt tgtgatgcta ttgctttatt tgtaaccatt ataagctgca ataaacaagt   1380

taacaacaac aattgcattc attttatgtt tcaggttcag ggggaggtgt gggaggtttt   1440

ttaagctgta tgtaattagt catttaaagg gaatgcctga atactttaaa gaattttggc   1500

agatttcaga tattggacaa acactcttag cttccacaaa cttaattcca aaaaataatt   1560

tttcacttat gagcaataga gttattacgg acatatcagc aaaaatgtag tagtgtcaag   1620

gctcatagat gatagaaatg aagagatgct gtattgatag aaatatgtga ttcaggactg   1680

tgtggatt                                                            1688
```

<210> SEQ ID NO 42
<211> LENGTH: 2640
<212> TYPE: DNA
<213> ORGANISM: Artificial Sequence
<220> FEATURE:
<223> OTHER INFORMATION: pHMI-hF8-001-F8 correction genome including ITRs

<400> SEQUENCE: 42

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctggagg ggtggagtcg tgacgtgaat tacgtcatag    180

ggttagggag gtcctgcata tggcagtcta ataaggaaag cagaaaagca aagcaacctt    240

ataatatggt gcaataattt gctataatga agttatatac aaagtgaagt agaagcatag    300

aagaagcagc actaaatttg tctgggtgag tcagagaagg ctaaccagga aaaatagttt    360

ctgaactaac acttgaagga ggtgtagcag ttcatcactg acagtgatgt tggggtgggt    420

ctggtttcag gagaggggag gaaattggct ttggtctgag gctgaggtgt gggcaaagca    480

ttagcttatg tgggtccatt agcttatgtg agtccacaaa aggtgtgtgt gtgtttgtgt    540
```

-continued

```
gtatgtgtgt gtgtgtgtgt gtgtgtgtgt gtgtacgaaa tgggggctca atgatttggt    600
agtggtttgg tttgtcaaga agcaggctgg gaactcaata agcatctttc cattcatttc    660
tactgtgtat cccacagctt cacacacaca tgcacatttc aacattggtg actgcttcac    720
ttgcacacct aaggtaatga tggacacacc tgtagcaatg tagattcttc ctaagctaat    780
aattagtttc aggaggtagc acatacattt aaaaataggt taaaataaag tgttatttta    840
attggtaggt ggatctgttg gcaccaatga ttattcacgg catcaagacc cagggtgccc    900
gtcagaagtt ctccagcctc tacatctctc agtttatcat catgtatagt cttgatggga    960
agaagtggca gacttatcga ggaaattcca ctggaacctt aatggtcttc tttggcaatg   1020
tggattcatc tgggataaaa cacaatattt ttaaccctcc aattattgct cgatacatcc   1080
gtttgcaccc aactcattat agcattcgca gcactcttcg catggagttg atgggctgtg   1140
atttaaatag ttgcagcatg ccattgggaa tggagagtaa agcaatatca gatgcacaga   1200
ttactgcttc atcctacttt accaatatgt ttgccacctg gtctccttca aaagctcgac   1260
ttcacctcca agggaggagt aatgcctgga gacctcaggt gaataatcca aaagagtggc   1320
tgcaagtgga cttccagaag acaatgaaag tcacaggagt aactactcag ggagtaaaat   1380
ctctgcttac cagcatgtat gtgaaggagt tcctcatctc cagcagtcaa gatggccatc   1440
agtggactct ctttttttcag aatggcaaag taaaggtttt tcagggaaat caagactcct   1500
tcacacctgt ggtgaactct ctagacccac cgttactgac tcgctacctt cgaattcacc   1560
cccagagttg ggtgcaccag attgccctga ggatggaggt tctgggctgc gaggcacagg   1620
acctctactg aaagctttac gtatgtaatt agtcatttaa agggaatgcc tgaatacttt   1680
aaagaatttt ggcagatttc agatattgga caaacactct tagcttccac aaacttaatt   1740
ccaaaaaata atttttcact tatgagcaat agagttatta cggacatatc agcaaaaatg   1800
tagtagtgtc aaggctcata gatgatagaa atgaagagat gctgtattga tagaaatatg   1860
tgattcagga ctgtgtggat tgatgattgt gagcttgctt atggatatcc taggtttgag   1920
gttatagtag gacaatcagg ttgaaatgtc cagcaggcag taggtgaaag acaagtttag   1980
ggggcaaaac catggatgga gatgaagatt catgacttcc acataaaagg atgggtgaaa   2040
ctttgggaat tgatgaattc tctagaggtg agctcaagac ccttaaaggc ttaaaacctc   2100
agcgttattg tctactcttc cctcattttt atgcccacaa atctggtcaa tcctttattt   2160
gcaatgcctc tcacatctct ttcttctgtt tccatttata ccgctgttgc cacagcccag   2220
ggtcccatca cctcacactt gatctattgt attacattcc taactagtct tcccccgttt   2280
ctaatctgtt ctccgataaa agctgcacat cattttcagg ataatcatca gtcgcctgcc   2340
taaaactttt caatgtcttc ccattgtctt tagaataaag ttcaaagtct tcaaatgacc   2400
ccaagcaaga taacttttgt ttgccccttt agatccattt aaatgcaggt ctagatacgt   2460
agataagtag catggcgggt taatcattaa ctacaaggaa cccctagtga tggagttggc   2520
cactccctct ctgcgcgctc gctcgctcac tgaggccggg cgaccaaagg tcgcccgacg   2580
cccgggcttt gcccgggcgg cctcagtgag cgagcgagcg cgcagagagg gagtggccaa   2640
```

<210> SEQ ID NO 43
<211> LENGTH: 2886
<212> TYPE: DNA
<213> ORGANISM: Artificial Sequence
<220> FEATURE:
<223> OTHER INFORMATION: pHMI-hF8-002-F8 correction genome including
      ITRs

<400> SEQUENCE: 43

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctggagg ggtggagtcg tgacgtgaat tacgtcatag    180
ggttagggag gtcctgcata tggcagtcta ataaggaaag cagaaaagca aagcaacctt    240
ataatatggt gcaataattt gctataatga agttatatac aaagtgaagt agaagcatag    300
aagaagcagc actaaatttg tctgggtgag tcagagaagg ctaaccagga aaaatagttt    360
ctgaactaac acttgaagga ggtgtagcag ttcatcactg acagtgatgt tggggtgggt    420
ctggtttcag gagaggggag gaaattggct ttggtctgag gctgaggtgt gggcaaagca    480
ttagcttatg tgggtccatt agcttatgtg agtccacaaa aggtgtgtgt gtgtttgtgt    540
gtatgtgtgt gtgtgtgtgt gtgtgtgtgt gtgtacgaaa tgggggctca atgatttggt    600
agtggtttgg tttgtcaaga agcaggctgg gaactcaata agcatctttc cattcatttc    660
tactgtgtat cccacagctt cacacacaca tgcacatttc aacattggtg actgcttcac    720
ttgcacacct aaggtaatga tggacacacc tgtagcaatg tagattcttc ctaagctaat    780
aattagtttc aggaggtagc acatacattt aaaaataggt taaaataaag tgttatttta    840
attggtaggt ggatctgttg gcaccaatga ttattcacgg catcaagacc cagggtgccc    900
gtcagaagtt ctccagcctc tacatctctc agtttatcat catgtatagt cttgatggga    960
agaagtggca gacttatcga ggaaattcca ctggaacctt aatggtcttc tttggcaatg   1020
tggattcatc tgggataaaa cacaatattt ttaaccctcc aattattgct cgatacatcc   1080
gtttgcaccc aactcattat agcattcgca gcactcttcg catggagttg atgggctgtg   1140
atttaaatag ttgcagcatg ccattgggaa tggagagtaa agcaatatca gatgcacaga   1200
ttactgcttc atcctacttt accaatatgt ttgccacctg gtctccttca aaagctcgac   1260
ttcacctcca agggaggagt aatgcctgga gacctcaggt gaataatcca aaagagtggc   1320
tgcaagtgga cttccagaag acaatgaaag tcacaggagt aactactcag ggagtaaaat   1380
ctctgcttac cagcatgtat gtgaaggagt tcctcatctc cagcagtcaa gatggccatc   1440
agtggactct ctttttcag aatggcaaag taaaggtttt tcagggaaat caagactcct    1500
tcacacctgt ggtgaactct ctagacccac cgttactgac tcgctacctt cgaattcacc   1560
cccagagttg ggtgcaccag attgccctga ggatggaggt tctgggctgc gaggcacagg   1620
acctctactg aaagctttac caaggcctct cgagcctcta gaactatagt gagtcgtatt   1680
acgtagatcc agacatgata agatacattg atgagtttgg acaaaccaca actagaatgc   1740
agtgaaaaaa atgctttatt tgtgaaattt gtgatgctat tgctttattt gtaaccatta   1800
taagctgcaa taaacaagtt aacaacaaca attgcattca ttttatgttt caggttcagg   1860
gggaggtgtg ggaggttttt taagctgtat gtaattagtc atttaaaggg aatgcctgaa   1920
tactttaaag aattttggca gatttcagat attggacaaa cactcttagc ttccacaaac   1980
ttaattccaa aaaataattt ttcacttatg agcaatagag ttattacgga catatcagca   2040
aaaatgtagt agtgtcaagg ctcatagatg atagaaatga agagatgctg tattgataga   2100
aatatgtgat tcaggactgt gtggattgat gattgtgagc ttgcttatgg atatcctagg   2160
tttgaggtta tagtaggaca atcaggttga aatgtccagc aggcagtagg tgaaagacaa   2220
gtttaggggg caaaaccatg gatggagatg aagattcatg acttccacat aaaaggatgg   2280
gtgaaacttt gggaattgat gaattctcta gaggtgagct caagaccctt aaaggcttaa   2340
```

aacctcagcg ttattgtcta ctcttccctc atttttatgc ccacaaatct ggtcaatcct 2400
ttatttgcaa tgcctctcac atctctttct tctgtttcca tttataccgc tgttgccaca 2460
gcccagggtc ccatcacctc acacttgatc tattgtatta cattcctaac tagtcttccc 2520
ccgtttctaa tctgttctcc gataaaagct gcacatcatt ttcaggataa tcatcagtcg 2580
cctgcctaaa acttttcaat gtcttcccat tgtctttaga ataaagttca aagtcttcaa 2640
atgaccccaa gcaagataac ttttgtttgc ccctttagat ccatttaaat gcaggtctag 2700
atacgtagat aagtagcatg gcgggttaat cattaactac aaggaacccc tagtgatgga 2760
gttggccact ccctctctgc gcgctcgctc gctcactgag gccgggcgac caaaggtcgc 2820
ccgacgcccg ggctttgccc gggcggcctc agtgagcgag cgagcgcgca gagagggagt 2880
ggccaa 2886

<210> SEQ ID NO 44
<211> LENGTH: 1846
<212> TYPE: DNA
<213> ORGANISM: Artificial Sequence
<220> FEATURE:
<223> OTHER INFORMATION: pHMI-hF8-003-F8 correction genome including ITRs

<400> SEQUENCE: 44
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctggagg ggtggagtcg tgacgtgaat tacgtcatag 180
ggttagggag gtcctgcata tggcggaaat tggctttggt ctgaggctga ggtgtgggca 240
aagcattagc ttatgtgggt ccattagctt atgtgagtcc acaaaaggtg tgtgtgtgtt 300
tgtgtgtatg tgtgtgtgtg tgtgtgtgtg tgtgtgtgta cgaaatgggg gctcaatgat 360
ttggtagtgg tttggtttgt caagaagcag gctgggaact caataagcat ctttccattc 420
atttctactg tgtatcccac agcttcacac acacatgcac atttcaacat tggtgactgc 480
ttcacttgca cacctaaggt aatgatggac acacctgtag caatgtagat tcttcctaag 540
ctaataatta gtttcaggag gtagcacata catttaaaaa taggttaaaa taaagtgtta 600
ttttaattgg taggtggatc tgttggcacc aatgattatt cacggcatca agacccaggg 660
tgcccgtcag aagttctcca gcctctacat ctctcagttt atcatcatgt atagtcttga 720
tgggaagaag tggcagactt atcgaggaaa ttccactgga accttaatgg tcttctttgg 780
caatgtggat tcatctggga taaaacacaa tatttttaac cctccaatta ttgctcgata 840
catccgtttg cacccaactc attatagcat tcgcagcact cttcgcatgg agttgatggg 900
ctgtgattta aatagttgca gcatgccatt gggaatggag agtaaagcaa tatcagatgc 960
acagattact gcttcatcct actttaccaa tatgtttgcc acctggtctc cttcaaaagc 1020
tcgacttcac ctccaaggga ggagtaatgc ctggagacct caggtgaata atccaaaaga 1080
gtggctgcaa gtggacttcc agaagacaat gaaagtcaca ggagtaacta ctcagggagt 1140
aaaatctctg cttaccagca tgtatgtgaa ggagttcctc atctccagca gtcaagatgg 1200
ccatcagtgg actctctttt ttcagaatgg caaagtaaag gtttttcagg gaaatcaaga 1260
ctccttcaca cctgtggtga actctctaga cccaccgtta ctgactcgct accttcgaat 1320
tcacccccag agttgggtgc accagattgc cctgaggatg gaggttctgg gctgcgaggc 1380
acaggacctc tactgaaagc tttacgtatg taattagtca tttaaaggga atgcctgaat 1440
actttaaaga attttggcag atttcagata ttggacaaac actcttagct tccacaaact 1500
taattccaaa aaataatttt tcacttatga gcaatagagt tattacggac atatcagcaa 1560
aaatgtagta gtgtcaaggc tcatagatga tagaaatgaa gagatgctgt attgatagaa 1620
atatgtgatt caggactgtg tggattaaat gcaggtctag atacgtagat aagtagcatg 1680
gcgggttaat cattaactac aaggaacccc tagtgatgga gttggccact ccctctctgc 1740
gcgctcgctc gctcactgag gccgggcgac caaaggtcgc ccgacgcccg ggctttgccc 1800
gggcggcctc agtgagcgag cgagcgcgca gagagggagt ggccaa 1846

<210> SEQ ID NO 45
<211> LENGTH: 2092
<212> TYPE: DNA
<213> ORGANISM: Artificial Sequence
<220> FEATURE:
<223> OTHER INFORMATION: pHMI-hF8-004-F8 correction genome including ITRs

<400> SEQUENCE: 45
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctggagg ggtggagtcg tgacgtgaat tacgtcatag 180
ggttagggag gtcctgcata tggcggaaat tggctttggt ctgaggctga ggtgtgggca 240
aagcattagc ttatgtgggt ccattagctt atgtgagtcc acaaaaggtg tgtgtgtgtt 300
tgtgtgtatg tgtgtgtgtg tgtgtgtgtg tgtgtgtgta cgaaatgggg gctcaatgat 360
ttggtagtgg tttggtttgt caagaagcag gctgggaact caataagcat ctttccattc 420
atttctactg tgtatcccac agcttcacac acacatgcac atttcaacat tggtgactgc 480
ttcacttgca cacctaaggt aatgatggac acacctgtag caatgtagat tcttcctaag 540
ctaataatta gtttcaggag gtagcacata catttaaaaa taggttaaaa taaagtgtta 600
ttttaattgg taggtggatc tgttggcacc aatgattatt cacggcatca agacccaggg 660
tgcccgtcag aagttctcca gcctctacat ctctcagttt atcatcatgt atagtcttga 720
tgggaagaag tggcagactt atcgaggaaa ttccactgga accttaatgg tcttctttgg 780
caatgtggat tcatctggga taaaacacaa tatttttaac cctccaatta ttgctcgata 840
catccgtttg cacccaactc attatagcat tcgcagcact cttcgcatgg agttgatggg 900
ctgtgattta aatagttgca gcatgccatt gggaatggag agtaaagcaa tatcagatgc 960
acagattact gcttcatcct actttaccaa tatgtttgcc acctggtctc cttcaaaagc 1020
tcgacttcac ctccaaggga ggagtaatgc ctggagacct caggtgaata atccaaaaga 1080
gtggctgcaa gtggacttcc agaagacaat gaaagtcaca ggagtaacta ctcagggagt 1140
aaaatctctg cttaccagca tgtatgtgaa ggagttcctc atctccagca gtcaagatgg 1200
ccatcagtgg actctctttt ttcagaatgg caaagtaaag gtttttcagg gaaatcaaga 1260
ctccttcaca cctgtggtga actctctaga cccaccgtta ctgactcgct accttcgaat 1320
tcacccccag agttgggtgc accagattgc cctgaggatg gaggttctgg gctgcgaggc 1380
acaggacctc tactgaaagc tttaccaagg cctctcgagc ctctagaact atagtgagtc 1440
gtattacgta gatccagaca tgataagata cattgatgag tttggacaaa ccacaactag 1500
aatgcagtga aaaaaatgct ttatttgtga aatttgtgat gctattgctt tatttgtaac 1560
cattataagc tgcaataaac aagttaacaa caacaattgc attcatttta tgtttcaggt 1620
tcagggggag gtgtgggagg ttttttaagc tgtatgtaat tagtcattta aagggaatgc 1680
ctgaatactt taaagaattt tggcagattt cagatattgg acaaacactc ttagcttcca 1740
caaacttaat tccaaaaaat aatttttcac ttatgagcaa tagagttatt acggacatat 1800
cagcaaaaat gtagtagtgt caaggctcat agatgataga aatgaagaga tgctgtattg 1860
atagaaatat gtgattcagg actgtgtgga ttaaatgcag gtctagatac gtagataagt 1920
agcatggcgg gttaatcatt aactacaagg aacccctagt gatggagttg gccactccct 1980
ctctgcgcgc tcgctcgctc actgaggccg ggcgaccaaa ggtcgcccga cgcccgggct 2040
ttgcccgggc ggcctcagtg agcgagcgag cgcgcagaga gggagtggcc aa 2092

<210> SEQ ID NO 46
<211> LENGTH: 106
<212> TYPE: DNA
<213> ORGANISM: Artificial Sequence
<220> FEATURE:
<223> OTHER INFORMATION: truncated AAV2 5' ITR

<400> SEQUENCE: 46
ctgcgcgctc gctcgctcac tgaggccgcc cgggcaaagc ccgggcgtcg ggcgaccttt 60
ggtcgcccgg cctcagtgag cgagcgagcg cgcagagagg gagtgg 106

<210> SEQ ID NO 47
<211> LENGTH: 25
<212> TYPE: DNA
<213> ORGANISM: Mus musculus

<400> SEQUENCE: 47
agtccatcca tgagatggaa acaaa 25

<210> SEQ ID NO 48
<211> LENGTH: 24
<212> TYPE: DNA
<213> ORGANISM: Mus musculus

<400> SEQUENCE: 48
acaagccaat tcttgaagta acag 24

<210> SEQ ID NO 49
<211> LENGTH: 26
<212> TYPE: DNA
<213> ORGANISM: Mus musculus

<400> SEQUENCE: 49
tcctctatat gatttgaact gtctcc 26

<210> SEQ ID NO 50
<211> LENGTH: 24
<212> TYPE: DNA
<213> ORGANISM: Artificial Sequence
<220> FEATURE:
<223> OTHER INFORMATION: SA2A_Vector_Set2 probe

<400> SEQUENCE: 50
ttctaacatg cggtgacgtg gagg 24

<210> SEQ ID NO 51
<211> LENGTH: 17
<212> TYPE: DNA
<213> ORGANISM: Artificial Sequence
<220> FEATURE:

<223> OTHER INFORMATION: SA2A_Vector_Set2 primer 1

<400> SEQUENCE: 51
cctagggccg ggattct 17

<210> SEQ ID NO 52
<211> LENGTH: 20
<212> TYPE: DNA
<213> ORGANISM: Artificial Sequence
<220> FEATURE:
<223> OTHER INFORMATION: SA2A_Vector_Set2 primer 2

<400> SEQUENCE: 52
cctcttctct tcctcccaca 20

<210> SEQ ID NO 53
<211> LENGTH: 20
<212> TYPE: DNA
<213> ORGANISM: Mus musculus

<400> SEQUENCE: 53
ggaagagctg gcactcagaa 20

<210> SEQ ID NO 54
<211> LENGTH: 25
<212> TYPE: DNA
<213> ORGANISM: Artificial Sequence
<220> FEATURE:
<223> OTHER INFORMATION: F8_LeftA_R

<400> SEQUENCE: 54
cttaatattc ttggcatcct ccatg 25

<210> SEQ ID NO 55
<211> LENGTH: 21
<212> TYPE: DNA
<213> ORGANISM: Mus musculus

<400> SEQUENCE: 55
gctccagaat acacggttgt g 21

<210> SEQ ID NO 56
<211> LENGTH: 23
<212> TYPE: DNA
<213> ORGANISM: Mus musculus

<400> SEQUENCE: 56
ccattgactg tgtgcatttt agg 23

<210> SEQ ID NO 57
<211> LENGTH: 20
<212> TYPE: DNA
<213> ORGANISM: Artificial Sequence
<220> FEATURE:
<223> OTHER INFORMATION: F8_RightA_F

<400> SEQUENCE: 57
atgaagcttg acggtggttc 20

<210> SEQ ID NO 58
<211> LENGTH: 22
<212> TYPE: DNA
<213> ORGANISM: Mus musculus

<400> SEQUENCE: 58

```
tacgtagata agtagcatgg cg                                            22


<210> SEQ ID NO 59
<211> LENGTH: 24
<212> TYPE: DNA
<213> ORGANISM: Mus musculus

<400> SEQUENCE: 59

atgataccca tttccctaga ttcc                                          24


<210> SEQ ID NO 60
<211> LENGTH: 21
<212> TYPE: DNA
<213> ORGANISM: Mus musculus

<400> SEQUENCE: 60

ggcaccactc ctgaaataca c                                             21


<210> SEQ ID NO 61
<211> LENGTH: 143
<212> TYPE: DNA
<213> ORGANISM: Artificial Sequence
<220> FEATURE:
<223> OTHER INFORMATION: 3' ITR

<400> SEQUENCE: 61

aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag agagggagtg gcc                                           143


<210> SEQ ID NO 62
<211> LENGTH: 37
<212> TYPE: DNA
<213> ORGANISM: Artificial Sequence
<220> FEATURE:
<223> OTHER INFORMATION: additional 37 bp for 3' ITR

<400> SEQUENCE: 62

gtagataagt agcatggcgg gttaatcatt aactaca                            37


<210> SEQ ID NO 63
<211> LENGTH: 180
<212> TYPE: DNA
<213> ORGANISM: Artificial Sequence
<220> FEATURE:
<223> OTHER INFORMATION: 3' ITR with additional 37 bp sequence

<400> SEQUENCE: 63

gtagataagt agcatggcgg gttaatcatt aactacaagg aacccctagt gatggagttg     60

gccactccct ctctgcgcgc tcgctcgctc actgaggccg ggcgaccaaa ggtcgcccga    120

cgcccgggct ttgcccgggc ggcctcagtg agcgagcgag cgcgcagaga gggagtggcc    180
```